(12) United States Patent
Facchetti et al.

(10) Patent No.: US 7,902,363 B2
(45) Date of Patent: Mar. 8, 2011

(54) DIIMIDE-BASED SEMICONDUCTOR MATERIALS AND METHODS OF PREPARING AND USING THE SAME

(75) Inventors: Antonio Facchetti, Chicago, IL (US); Tobin J. Marks, Evanston, IL (US); He Yan, Skokie, IL (US)

(73) Assignee: Polyera Corporation, Skokie, IL (US)

( * ) Notice: Subject to any disclaimer, the term of this patent is extended or adjusted under 35 U.S.C. 154(b) by 672 days.

(21) Appl. No.: 11/986,019

(22) Filed: Nov. 19, 2007

(65) Prior Publication Data
US 2008/0185577 A1 Aug. 7, 2008

Related U.S. Application Data

(60) Provisional application No. 60/859,761, filed on Nov. 17, 2006.

(51) Int. Cl.
*C07D 471/08* (2006.01)
*H01L 51/50* (2006.01)

(52) U.S. Cl. .......................................... 546/37; 313/504
(58) Field of Classification Search .................... 546/37; 313/504
See application file for complete search history.

(56) References Cited

U.S. PATENT DOCUMENTS

| | | |
|---|---|---|
| 2,087,133 A | 7/1937 | Vollmann |
| 4,378,302 A | 3/1983 | Aftergut et al. |
| 4,611,385 A | 9/1986 | Forrest et al. .................... 29/574 |
| 4,846,892 A | 7/1989 | Henning et al. |
| 5,405,962 A | 4/1995 | Muellen et al. |
| 5,472,494 A | 12/1995 | Hetzenegger et al. |
| 5,539,100 A | 7/1996 | Wasielewski et al. |
| 5,677,417 A | 10/1997 | Muellen et al. |
| 5,808,073 A | 9/1998 | Böhm et al. |
| 5,908,583 A | 6/1999 | Havinga et al. |
| 5,986,099 A | 11/1999 | Müllen et al. |
| 6,063,181 A | 5/2000 | Bohm et al. |
| 6,084,099 A | 7/2000 | Hackmann et al. |
| 6,099,636 A | 8/2000 | Henning et al. |
| 6,124,458 A | 9/2000 | Müellen et al. |
| 6,143,905 A | 11/2000 | Bohm et al. |
| 6,165,661 A | 12/2000 | Hsiao et al. |
| 6,184,378 B1 | 2/2001 | Bohm et al. |
| 6,252,245 B1 | 6/2001 | Katz et al. |
| 6,287,738 B1 | 9/2001 | Duff et al. |
| 6,326,494 B1 | 12/2001 | Bohm et al. |
| 6,348,595 B1 | 2/2002 | Hendi |
| 6,486,319 B1 | 11/2002 | Böhm et al. |
| 6,533,857 B1 | 3/2003 | Schmid et al. |
| 6,551,717 B2 | 4/2003 | Katz et al. ..................... 428/447 |
| 6,585,914 B2 | 7/2003 | Marks et al. |
| 6,608,323 B2 | 8/2003 | Marks et al. |
| 6,656,651 B1 | 12/2003 | Bender et al. |
| 6,727,318 B1 | 4/2004 | Mathauer et al. |
| 6,784,301 B2 | 8/2004 | Hackmann et al. |
| 6,806,368 B2 | 10/2004 | Wurthner et al. |
| 6,878,825 B2 | 4/2005 | Krieger et al. |
| 6,890,377 B2 | 5/2005 | Böhm et al. |
| 6,916,928 B2 | 7/2005 | Becker et al. |
| 6,986,811 B2 | 1/2006 | Könemann et al. |
| 7,083,675 B2 | 8/2006 | Mizuguchi et al. |
| 7,105,046 B2 | 9/2006 | Mizuguchi et al. |
| 7,105,674 B2 | 9/2006 | Hackmann et al. |
| 7,326,956 B2 | 2/2008 | Shukla et al. .................... 257/40 |
| 7,422,777 B2 | 9/2008 | Shukla et al. ................... 428/1.1 |
| 7,671,202 B2 * | 3/2010 | Marks et al. ..................... 546/37 |
| 2003/0181721 A1 | 9/2003 | Wurthner et al. |
| 2003/0219625 A1 | 11/2003 | Wolk et al. |
| 2004/0013959 A1 | 1/2004 | Bender et al. |
| 2004/0023061 A1 | 2/2004 | Kathirgamanathan et al. |
| 2005/0075453 A1 | 4/2005 | Mathauer et al. |
| 2005/0092982 A1 | 5/2005 | Mullen et al. |
| 2005/0106415 A1 | 5/2005 | Jarikov et al. |
| 2005/0131220 A1 | 6/2005 | Dung et al. |
| 2005/0171252 A1 | 8/2005 | Schambony et al. |
| 2005/0176970 A1 | 8/2005 | Marks et al. ..................... 549/41 |
| 2005/0222416 A1 | 10/2005 | Bohm et al. |
| 2005/0238974 A1 | 10/2005 | Sekiya et al. |
| 2005/0251930 A1 | 11/2005 | Erk et al. |
| 2006/0058330 A1 | 3/2006 | Krieger et al. |
| 2006/0075585 A1 | 4/2006 | Krieger et al. |
| 2006/0131564 A1 | 6/2006 | Shukla et al. |
| 2006/0134823 A1 | 6/2006 | Shukla et al. .................... 438/99 |
| 2006/0141287 A1 | 6/2006 | Klubek et al. |
| 2006/0210898 A1 | 9/2006 | Jubran |
| 2006/0229385 A1 | 10/2006 | Boehm |
| 2006/0237712 A1 | 10/2006 | Shukla et al. .................... 257/40 |
| 2007/0026332 A1 | 2/2007 | Ferrar et al. |

(Continued)

FOREIGN PATENT DOCUMENTS

DE 2951349 A1 7/1981

(Continued)

OTHER PUBLICATIONS

Ahrens et al., "Cyanated Perylene-3,4-dicarboximides and Perylene-3,4:9,10-bis(dicarboximide):Facile Chromophoric Oxidants for Organic Photonics and Electronics," *Chem. Mater.*, 15:2684-2686 (2003).

Baier et al., "Intermolecular energy transfer after vibrational excitation of a perylene dye in solution, in polymer binder, and in a side-chain copolymer,", *J. Chem. Phys.*, 114: 6739-6743 (2001).

Buncel et al., "Synthesis and characterization of [3,3]- and [3,4]-perinophane," *Tetrahedron Letters*, 42: 3559-3562 (2001).

Database Caplus [Online] Chemical Abstracts Service, Columbus, Ohio, US; May 12, 1984, XP002493285 retrieved from STN Database accession No. 1984:34294 abstract.

Database WPI Thomson Scientific, London, GB; AN 1983-750663 XP002493286 and JP 58 124790 A (Matsushita Electric Ind. Co. Ltd.) Jul. 25, 1983 abstract.

Facchetti et al., "Building Blocks for n-Type Organic Electronics. Regiochemically Modulated Inversion of Majority Carrier Sign in Perfluoroarene-Modified Polythiophene Conductors,"*Angew. Chem. Int. Ed.*, 2003: 42, 3900-3903.

(Continued)

*Primary Examiner* — Charanjit S Aulakh
(74) *Attorney, Agent, or Firm* — K&L Gates LLP

(57) ABSTRACT

Diimide-based semiconductor materials are provided with processes for preparing the same. Composites and electronic devices including the diimide-based semiconductor materials also are provided.

20 Claims, 8 Drawing Sheets

U.S. PATENT DOCUMENTS

| | | | |
|---|---|---|---|
| 2007/0096084 A1 | 5/2007 | Shukla et al. | 257/40 |
| 2007/0116895 A1 | 5/2007 | Shukla et al. | 428/1.1 |
| 2008/0021220 A1 | 1/2008 | Marks et al. | 546/68 |
| 2008/0135833 A1 | 6/2008 | Shukla et al. | 257/40 |
| 2008/0161569 A1 | 7/2008 | Dung et al. | |
| 2008/0167435 A1 | 7/2008 | Marks et al. | 526/259 |
| 2008/0177073 A1 | 7/2008 | Facchetti et al. | 546/34 |
| 2008/0185555 A1 | 8/2008 | Facchetti et al. | 252/182.3 |
| 2008/0249309 A1 | 10/2008 | Facchetti et al. | |

FOREIGN PATENT DOCUMENTS

| | | |
|---|---|---|
| DE | 3434059 A1 | 3/1985 |
| DE | 3620332 A1 | 12/1987 |
| DE | 3703131 | 8/1988 |
| DE | 4018830 | 12/1991 |
| DE | 4338784 | 5/1995 |
| DE | 4440242 | 5/1996 |
| DE | 19501737 A1 | 7/1996 |
| DE | 19547210 A1 | 6/1997 |
| DE | 19622673 A1 | 12/1997 |
| DE | 19651712 A1 | 6/1998 |
| DE | 19709008 A1 | 9/1998 |
| DE | 10038672 A1 | 5/2002 |
| DE | 10148172 A1 | 4/2003 |
| EP | 0031065 | 10/1983 |
| EP | 0 217 256 | 4/1987 |
| EP | 0 422 535 | 4/1991 |
| EP | 0 826 740 | 3/1998 |
| EP | 0 861 878 | 9/1998 |
| EP | 0 896 964 | 2/1999 |
| EP | 0 990 951 | 4/2000 |
| EP | 1 172 700 | 1/2002 |
| EP | 1 671 674 | 6/2006 |
| FR | 1 526 496 | 5/1968 |
| FR | 2 237 922 | 2/1975 |
| JP | 05-025174 | 2/1993 |
| JP | 05-027459 | 2/1993 |
| JP | 11-119455 | 4/1999 |
| JP | 2002-302674 | 10/2002 |
| JP | 2003-327587 | 11/2003 |
| JP | 2004-093801 | 3/2004 |
| JP | 2004-093802 | 3/2004 |
| JP | 2004-152815 | 5/2004 |
| JP | 2005-154409 | 6/2005 |
| JP | 2005-189765 | 7/2005 |
| JP | 2005-209887 | 8/2005 |
| JP | 2006-028027 | 2/2006 |
| WO | 90/01480 | 2/1990 |
| WO | 96/22332 | 7/1996 |
| WO | 97/22607 | 6/1997 |
| WO | 97/22608 | 6/1997 |
| WO | 97/26301 | 7/1997 |
| WO | 98/32799 | 7/1998 |
| WO | 98/32802 | 7/1998 |
| WO | 98/49164 | 11/1998 |
| WO | 00/69829 | 11/2000 |
| WO | 02/14414 | 2/2002 |
| WO | 03/091345 | 11/2003 |
| WO | 03/104232 | 12/2003 |
| WO | 2004/029028 | 4/2004 |
| WO | 2005/047265 | 5/2005 |
| WO | 2005/070894 | 8/2005 |
| WO | 2005/070895 | 8/2005 |
| WO | 2005/078023 | 8/2005 |
| WO | 2005/092901 | 10/2005 |
| WO | 2006/021307 | 3/2006 |
| WO | 2006/037539 | 4/2006 |
| WO | 2006/050860 | 5/2006 |
| WO | 2006/093965 | 9/2006 |
| WO | 2006/115714 | 11/2006 |
| WO | 2007/074137 | 7/2007 |
| WO | 2007/093643 | 8/2007 |
| WO | 2008/091670 | 7/2008 |

OTHER PUBLICATIONS

Facchetti et al., "n-Type Building Blocks for Organic Electronics: a Homologous Family of Fluorocarbon-substituted Thiophene Oligomers with High Carrier Mobility," *Adv. Mater.*, 2003: 15, 33-38.

Facchetti et al., "Tuning the Semiconducting Properties of Sexithiophene by a,w-Substitution—α,ω-Diperfluorohexylsexithiophene: the First n-Type Sexithiophene for Thin-film Transistors," *Angew. Chem. Int. Ed.*, 2000: 39, 4547-4551.

Giaimo et al., "Excited-State Symmetry Breaking in Cofacial and Linear Dimers of a Green Perylenediimide Chlorophyll Analogue Leading to Ultrafast Charge Separation," *J. Am. Chem. Soc.*, 124: 8530-8531 (2002).

Holman et al., "Studying and Switching Electron Transfer: From the Ensemble to the Single Molecule," *J. Am. Chem. Soc.*, 126: 16126-16133 (2004).

Huttner et al., "N-type organic field effect transistors from perylene bisimide block copolymers and homopolymers," *Appl. Phys. Lett.*, 92: 093302 (2008).

Jones et al., "High-Mobility Air-Stable n-Type Semiconductors with Processing Versatility: Dicyanoperylene-3,4:9,10-bis(dicarboximides)," *Agnew., Chem. Int. Ed.*, 43:6363-6366 (2004).

Jones et al., "Tuning Orbital Energetics in Arylene Diimide Semiconductors. Materials Design for Ambient Stability of n-Type Charge Transport," *J. Am. Chem. Soc.*, 2007: 129, 15259-15278.

Kwan et al., "Electrochemistry of Langmuir-Blodgett and Self-Assembled Films Built from Oligoimides," *Langmuir*, 8:3003-3007 (1992).

Langhals et al., "Tangentially Coupled π Systems and their Through-Space Interaction—Trichromophoric Perylene Dyes," *J. Prakt. Chem.*, 338: 654-659 (1996).

Langhals et al., "Chiral Bifluorophoric Perylene Dyes with Unusually High CD Effects—A Simple Model for the Photosynthesis Reaction Center," *Leibigs Ann./Recueil.*, 1151-1153 (1997).

Lindner et al., "Nanostructures of N-type organic semiconductor in a p-type matrix via self-assembly of block copolymers," *Macromolecules*, 37:8832-8835 (2004).

Lukas et al., "Femtosecond Optical Switching of Electron Transport Direction in Branched Donor-Acceptor Arrays," *J. Phys. Chem. B*, 104: 931-940 (2000).

Lukas et al., "Biomimetic Electron Transfer Using Low Energy Excited States: A Green Perylene-Based Analogue of Chloroophyll a," *J. Phys. Chem. B*, 106: 1299-1306 (2002).

Martyushina et al., "Searches for Nondepolarizing Short-Action Myorelaxants," *Pharm. Chem.*, 1982: 16 (7), 801-806 (English translation).

Muller et al., "Facile synthetic approach to novel core-extended perylene carboximide dyes," *Chem. Commun.*, (2005) 4045-4046.

Petit et al., "Synthesis of macromolecular substances comprising dye derivatives as monomeric units. III. Synthesis and study of monomeric dihydroxy dyes," *Bulletin de la Societe Chimique de France*, 7-8:1591-1596 (1974).

Rodriguez-Llorente et al., "Infrared and Raman spectra of thin solid films of 1,2-bis(propylimido perylene)ethane," *Spectrochimica Acta. Part A*, 55: 969-978 (1999).

Rodriguez-Llorente et al., "Vibrational spectra and thin solid films of a bi(propylperylenediimide)," *J. Mater. Chem.*, 8(10): 2175-2179 (1998).

Rodriguez-Llorente et al., "Spectroscopic characterization of thin solid films of a bis(chlorobenzylimidoperyleneimido)octane derivative," *J. Mater. Chem.*, 8(3): 629-632 (1998).

Shimizu et al., "Convergent Functional Groups. 15. Synthetic and Structural Studies of Large and Rigid Molecular Clefts," *J. Am. Chem. Soc.*, 116:5145-5149 (1994).

Singh et al., "Soluble derivatives of perylene and naphthalene diimide for n-channel organic field-effect transistors," *Organic Electronics*, 7:480-489 (2006).

Tauber et al., "Electron Hopping in π-Stacked Covalent and Self-Assembled Perylene Diimides Observed by ENDOR Spectroscopy," *JACS Comm.*, 128: 1782-1783 (2006).

Thalacker et al., "Hydrogen bond directed self-assembly of core-substituted naphthalene bisimides with melamines in solution and at the graphite interface," *Org. Biomol. Chem.*, 3:414-422 (2005).

Tsoi et al., "Distributed Bilayer Photovoltaics Based on Nematic Liquid Crystal Polymer Networks," *Chem. Mater.*, 19:5475-5484 (2007).

Chen et al., "Oligothiophene-Functionalized Perylene Bisimide System: Synthesis, Characterization, and Electrochemical Polymerization Properties," *Chem. Mater.*, 17:2208-2215 (2005).

Jones et al., "Cyanonaphthalene Diimide Semiconductors for Air-Stable, Flexible, and Optically Transparent n-Channel Field-Effect Transistors," *Chem. Mater.*, 19(11):2703-2705 (2007).

Lindner et al., "Charge Separation at Self-Assembled Nanostructured Bulk Interface in Block Copolymers," *Angew. Chem. Int. Ed.*, 45:3364-3368 (2006).

Morris et al., "Synthesis of Extended Linear Aromatics Using Tandem Diels-Alder Aromatization Reactions," *J. Org. Chem.*, 59:6484-6486 (1994).

Rohr et al., "Liquid crystalline coronene derivatives," *J. Mater. Chem.*, 11:1789-1799 (2001).

* cited by examiner

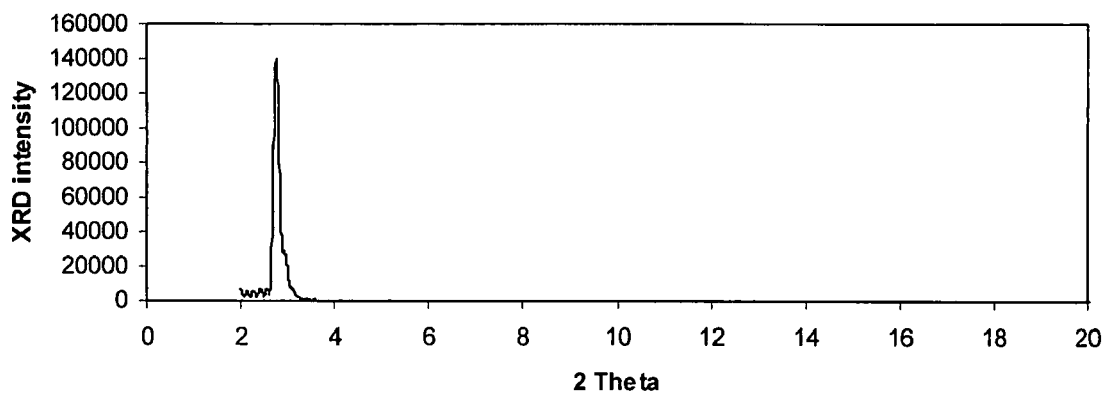
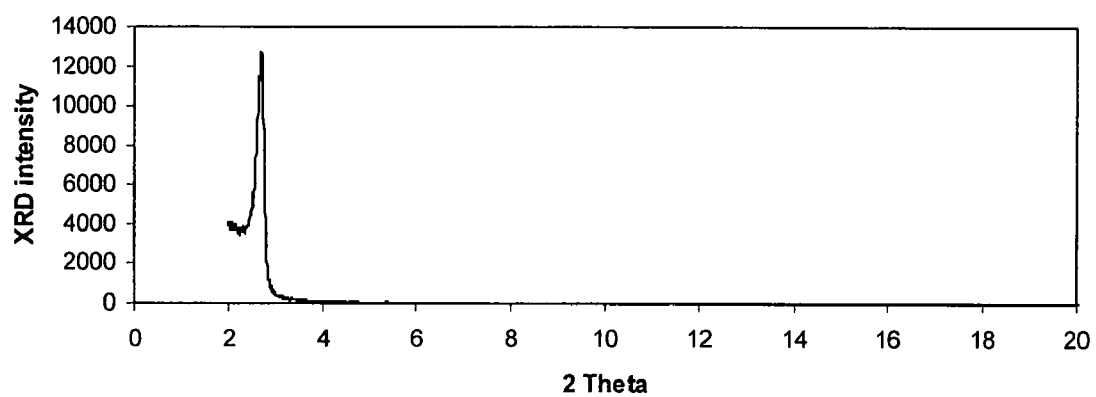
Figures 15A (top) and 15B (bottom)

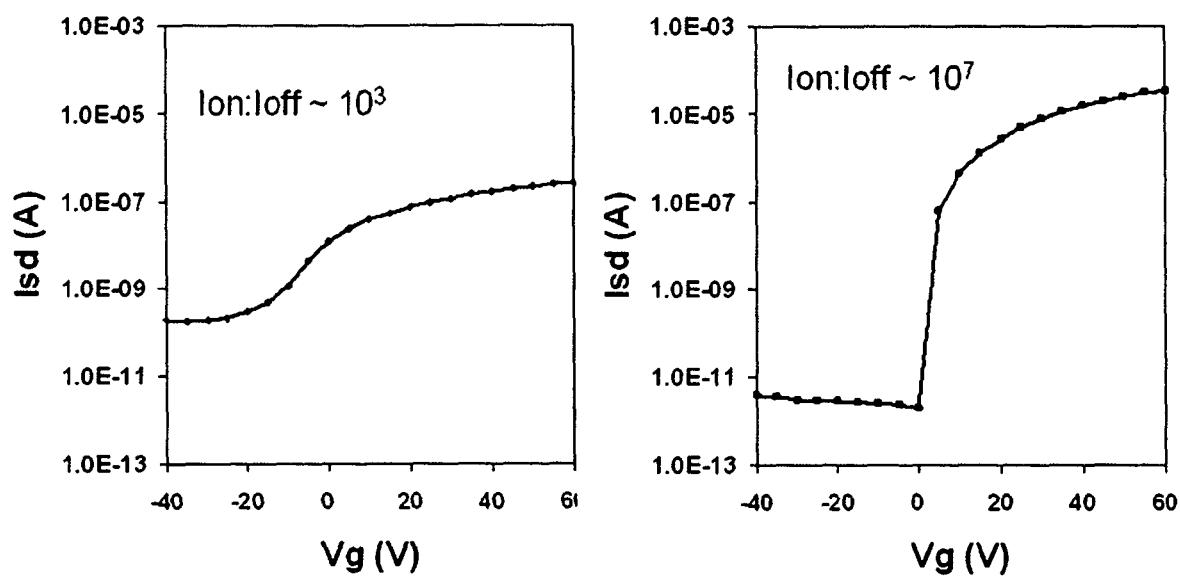
Figures 16A (left) and 16B (right)

DIIMIDE-BASED SEMICONDUCTOR MATERIALS AND METHODS OF PREPARING AND USING THE SAME

CROSS REFERENCE TO RELATED APPLICATION

This application claims priority to and the benefit of U.S. Provisional Patent Application Ser. No. 60/859,761, filed on Nov. 17, 2006.

INTRODUCTION

The electronic structure of most organic semiconductors consists of delocalized π orbitals within a molecular/polymeric σ framework that mainly constitutes sp² hybridized carbon atoms and to some extent, heteroatoms such as sulfur, selenium, nitrogen, and oxygen. The primary mechanism for charge transport in organic solids is based on efficient molecular/polymer chain stacking which results in π-π orbital interaction, allowing the charge carriers injected at the electrical contacts to migrate from molecule to molecule (chain to chain).

In the case of organic semiconductors designed for n-type (where electrons are the majority charge carriers) transistor applications, additional requirements need to be taken into consideration. These additional requirements include material compatibility in terms of LUMO (lowest unoccupied molecular orbital—equivalent to conduction band for inorganic semiconductors) energy, proper energy match with the source/drain electrodes, as well as optimized film morphology and microstructure to maximize conductivity in the transistor ON state.

To date, optimized organic materials are mainly p-type (where holes are the majority charge carriers) semiconductors due to their enhanced environmental stability. In contrast, n-type organic materials are limited to a handful of small molecules and polymers. Among the limited number of promising n-type semiconductors, most of them suffer from serious drawbacks including poor stability in air and poor solubility in common organic solvents, which limit the type of manufacturing processes (e.g., printing deposition) that can be used with these n-type semiconducting compounds.

Accordingly, there is a desire in the art for new air-stable and solution-processable n-type organic semiconductor compounds, compositions, and materials that can be integrated in various device designs including, but not limited to, complementary circuits, organic light emitting diodes (OLEDs), organic photovoltaics, capacitors, and sensors.

SUMMARY

In light of the foregoing, the present teachings provide organic semiconductor compounds and materials and associated devices that can address various deficiencies and shortcomings of the prior art, including those outlined above.

More specifically, the present teachings provide organic semiconductor compounds and materials that are based on N-functionalized diimides. It has been found that these compounds can afford useful electrical properties while offering a range of properties that can be suitable for solution-phase processing.

In one aspect, the present teachings provide compounds having the formula:

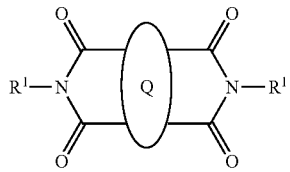

where Q and R¹ are as defined herein.

The present teachings also provide various compositions, articles of manufacture, structures, and devices that include the compounds disclosed herein.

The foregoing and other features and advantages of the present teachings will be more fully understood from the following figures, description, and claims.

BRIEF DESCRIPTION OF THE DRAWINGS

It should be understood that the drawings described below are for illustration purposes only and are not intended to limit the scope of the present teachings in any way.

FIG. 15A is a WAXRD Θ/2Θ scan for a vapor-phase deposited film of a compound of the present teachings (PDIPhPh-CN$_2$).

FIG. 15B is a WAXRD Θ/2Θ scan for a solution-phase deposited film of a compound of the present teachings (PDIPhPh-CN$_2$).

FIG. 16A is a representative transfer plot measured in air for a spin-coated film from chloroform of a compound of the present teachings (PDI8-CN$_2$).

FIG. 16B is a representative transfer plot measured in air for a spin-coated film from chloroform of a compound of the present teachings (PDI2EH-CN$_2$).

DETAILED DESCRIPTION

Figure 1:
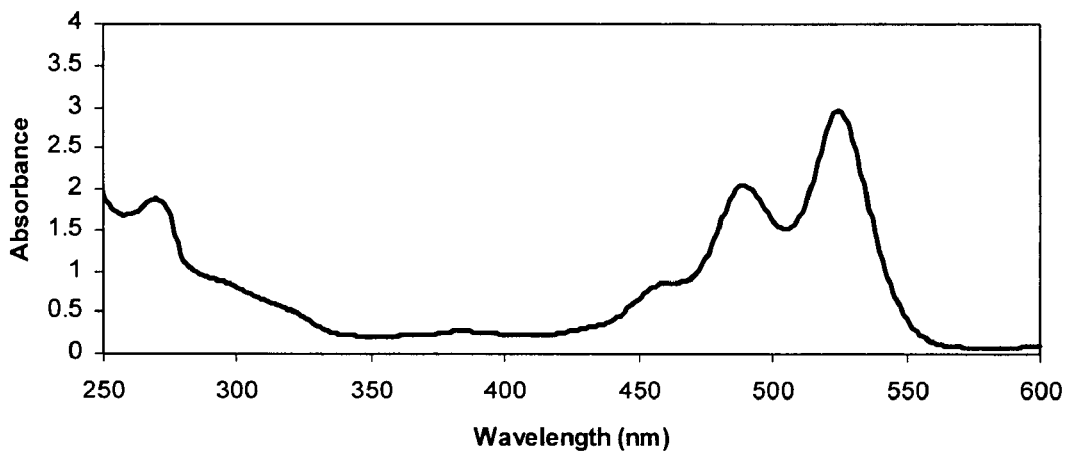
FIG. 1 is an ultraviolet-visible (UV-vis) absorption spectrum of a compound of the present teachings (PDIPh12-$CN_2$) in chloroform.

The present teachings relate to compounds, for example, organic semiconducting compounds, methods for preparing the same, as well as to compositions, materials, articles of manufacture, structures, and devices that include such compounds.

The present teachings provide vapor-deposited and solution-processable, e.g., spin-coatable and printable, organic semiconductor materials (including compounds and compositions) that exhibit useful electrical properties that can be used to fabricate various organic electronic articles, structures and devices. The organic semiconductor materials disclosed herein can be useful as n-type semiconductor materials (where the charge carriers are substantially electrons) and can be used, among other applications, to build complementary circuits with a p-type semiconductor (where the charge carriers are substantially holes) that is either inorganic or organic.

In particular, the present teachings provide various diimides where the nitrogen atoms are substituted with functional groups that can enhance the solubility of the compound as a whole. These compounds typically have at least some solubility in one or more common solvents and can be stable in ambient conditions. Without wishing to be bound to any particular theory, it is believed that suitable functionalization at the nitrogen atom also can enhance microstructural ordering within the films which promotes charge mobility. In certain embodiments, functionalization of the imide nitrogens of compounds of the present teachings with a 2-alkyl substituted alkyl group results in compositions that when spin-coated afford an unexpected increase in the electron mobility and current $I_{on}:I_{off}$ ratio of the resulting devices. The present teachings also provide compositions, articles of manufacture, structures, and devices that include one or more of these compounds.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

The use of the terms "include," "includes," "including," "have," "has," or "having" should be generally understood as open-ended and non-limiting unless specifically stated otherwise.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "solution-processable" refers to compounds, materials, or compositions that can be used in various solution-phase processes including spin-coating, printing (e.g., inkjet printing, screen printing, gravure, flexography), spray coating, electrospray coating, drop casting, dip coating, and blade coating.

As used herein, "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can include, without limitation, rylenes having the formula:

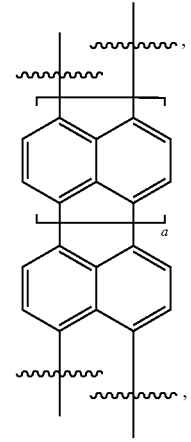

where a can be an integer in the range of 0-3; and linear acenes having the formula:

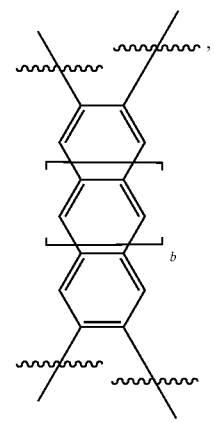

where b can be an integer in the range of 0-4.

As used herein, "imide" refers to a —C(O)—NH—C(O)— group, where the nitrogen atom can be substituted as disclosed herein.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, isobutyl, sec-butyl, tert-butyl), pentyl groups (e.g., n-pentyl, isopentyl, neopentyl), and the like. In various embodiments, an alkyl group can have 1 to 20 carbon atoms, i.e., a $C_{1-20}$ alkyl group. In some embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In some embodiments, alkyl groups can be substituted with up to four independently selected $R^b$ groups, where $R^b$ is as disclosed herein.

As used herein, "2-alkyl substituted alkyl" refers to an alkyl group substituted at its 2-position with an alkyl group. For example, when a 2-alkyl substituted alkyl group is present on an imide nitrogen, for example, as $R^1$ in formulae depicted herein, the second carbon atom removed from the imide nitrogen is substituted with an alkyl group. A 2-substituted alkyl group can have 3 to 20 carbon atoms, i.e., be a $C_{3-20}$ alkyl group. In some embodiments, the 2-substituted alkyl group can have 3 to 10 carbon atoms (i.e., a $C_{3-10}$ alkyl group) or 3 to 8 carbon atoms (i.e., a $C_{3-8}$ alkyl group). A substituent alkyl group can have 1 to 20 carbon atoms, i.e., be a $C_{1-20}$ alkyl group. In some embodiments, the substituent alkyl group can have 1 to 10 carbon atoms (i.e., a $C_{1-10}$ alkyl group), 1 to 8 carbon atoms (i.e., a $C_{1-8}$ alkyl group), or 1 to 6 carbon atoms (i.e., a $C_{1-6}$ alkyl group), and in the latter example can be referred to as a "lower alkyl group." Of course each of the specific examples of alkyl groups are contemplated as being individually recited in the various specific combinations of the 2-substituted alkyl group and the substituent alkyl group. For example, the 2-substituted alkyl group can be n-propyl, n-butyl, a pentyl group, a hexyl group, a heptyl group, an octyl group, a nonyl group, or a decyl group. The substituent alkyl group in combination with each of these 2-substituted alkyl groups can be methyl, ethyl, propyl (e.g., n-propyl and isopropyl), butyl groups (e.g., n-butyl, isobutyl, sec-butyl, tert-butyl), pentyl groups (e.g., n-pentyl, isopentyl, neopentyl), hexyl groups, heptyl groups, octyl groups, nonyl groups, decyl groups, and the like. In particular embodiments, the 2-alkyl substituted alkyl group can be 2-methylhexyl, 2-ethylhexyl, 2-propylhexyl, 2-butylhexyl, 2-pentylhexyl, or 2-hexylhexyl. It should be understood that 2-alkyl substituted alkyl groups can be di- or tri-substituted provided that substitution occurs at the third carbon atom or higher.

As used herein, "3-alkyl substituted alkyl" refers to an alkyl group substituted at its 3-position with an alkyl group. For example, when a 3-alkyl substituted alkyl group is present on an imide nitrogen, for example, as $R^1$ in formulae depicted herein, the third carbon atom removed from the imide nitrogen is substituted with an alkyl group. The various embodiments of 3-alkyl substituted alkyl groups are similar to those described above for the 2-alkyl substituted alkyl groups but for the different carbon atom where the substitution occurs. It should be understood that 3-alkyl substituted alkyl groups can be di- or tri-substituted provided that substitution occurs at the fourth carbon atom or higher.

As used herein, "alkoxy" refers to —O-alkyl group. An alkoxy group can have 1 to 20 carbon atoms, for example, 1 to 10 carbon atoms (i.e., a $C_{1-10}$ alkoxy group). Examples of alkoxy groups include, but are not limited to, methoxy, ethoxy, propoxy (e.g., n-propoxy and isopropoxy), t-butoxy groups, and the like.

As used herein, "alkylthio" refers to an —S-alkyl group. Examples of alkylthio groups include, but are not limited to, methylthio, ethylthio, propylthio (e.g., n-propylthio and isopropylthio), t-butylthio groups, and the like.

As used herein, "haloalkyl" refers to an alkyl group having one or more halogen substituents. Examples of haloalkyl groups include, but are not limited to, $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-20}$ haloalkyl group can have the formula $-C_nX_{2n+1}$ or $-C_nH_{2n+1-t}X_t$, wherein X is F, Cl, Br, or I, n is an integer in the range of 1 to 20, and t is an integer in the range of 0 to 41, provided that t is less than or equal to 2n+1.

As used herein, "arylalkyl" refers to an -alkyl-aryl group, wherein the arylalkyl group is covalently linked to the defined chemical structure via the alkyl group. An arylalkyl group is within the definition of an -L-$C_{6-14}$ aryl group, -L'-$C_{6-14}$ aryl group, or a —Y—$C_{6-14}$ aryl group, where L, L' and Y are independently divalent $C_{1-20}$ alkyl groups. An example of an arylalkyl group is a benzyl group (—$CH_2$—$C_6H_5$). The aryl group of the arylalkyl group can be optionally substituted as disclosed herein. For example, in some embodiments, -L-$Ar^1$—$R^2$ and -L'-$Ar^2$—$R^3$ can be independently a —$C_{1-20}$ alkyl-$C_{6-14}$ aryl group, where $R^2$ and $R^3$ are H and the $C_{6-14}$ aryl group can be optionally substituted with 1-4 $R^d$ groups, and $R^d$ is as defined herein. Such optionally substituted arylalkyl groups can be represented by the formula:

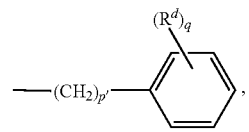

where p' is an integer in the range of 1 to 20, q is an integer in the range of 0 to 4, and $R^d$ is as defined herein.

As used herein, "alkenyl" refers to a straight-chain or branched alkyl group having one or more carbon-carbon double bonds. Examples of alkenyl groups include, but are not limited to, ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 20 carbon atoms, i.e., a $C_{2-20}$ alkenyl group. In some embodiments, alkenyl groups can be substituted with up to four independently selected $R^b$ groups, where $R^b$ is as disclosed herein.

As used herein, "alkynyl" refers to a straight-chain or branched alkyl group having one or more triple carbon-carbon bonds. Examples of alkynyl groups include, but are not limited to, ethynyl, propynyl, butynyl, pentynyl, and the like. The one or more triple carbon-carbon bonds can be internal (such as in 2-butyne) or terminal (such as in 1-butyne). In various embodiments, an alkynyl group can have 2 to 20 carbon atoms, i.e., a $C_{2-20}$ alkynyl group. In some embodiments, alkynyl groups can be substituted with up to four independently selected $R^b$ groups, where $R^b$ is as disclosed herein.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In various embodiments, a cycloalkyl group can have 3 to 14 carbon atoms, including 3 to 10 carbon atoms (i.e., a $C_{3-10}$ cycloalkyl group). In some embodiments, cycloalkyl groups can be substituted with up to four independently selected $R^b$ groups, where $R^b$ is as disclosed herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, N, S and Se, and optionally contains one or more double or triple bonds. In various embodiments, a cycloheteroalkyl group can have 3 to 20 ring atoms, including 3 to 14 ring atoms (i.e., a 3-14 membered cycloheteroalkyl group). One or more N or S atoms in a cycloheteroalkyl ring may be oxidized (e.g., morpholine N-oxide, thiomorpholine S-oxide, thiomorpholine S,S-dioxide). In some embodiments, nitrogen atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted with up to four independently selected $R^b$ groups, where $R^b$ is as disclosed herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 14 carbon atoms in its ring system, which can include multiple fused rings. In some embodiments, a polycyclic aryl group can have from 7 to 14 carbon atoms. Any suitable ring position of the aryl group can be covalently linked to the defined chemical structure. Examples of aryl groups having only aromatic carbocyclic ring(s) include, but are not limited to, phenyl, 1-naphthyl (bicyclic), 2-naphthyl (bicyclic), anthracenyl (tricyclic), phenanthrenyl (tricyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include, but are not limited to, benzodioxanyl, benzodioxolyl, chromanyl, indolinyl groups, and the like. In some embodiments, aryl groups can be substituted with up to four groups independently selected from $R^a$ or $R^d$ groups as disclosed herein. In certain embodiments, an aryl group is substituted with another aryl group and can be referred to as a biaryl group. Each of the aryl groups in the biaryl group can be substituted with up to four $R^d$ groups as disclosed herein.

As used herein, "heteroaryl" refers to an aromatic monocyclic ring system containing at least 1 ring heteroatom selected from oxygen (O), nitrogen (N), sulfur (S), and selenium (Se), or a polycyclic ring system where at least one of the rings present in the ring system is aromatic and contains at least 1 ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, from 5 to 14 ring atoms and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5-membered monocyclic and 5-6 bicyclic ring systems shown below:

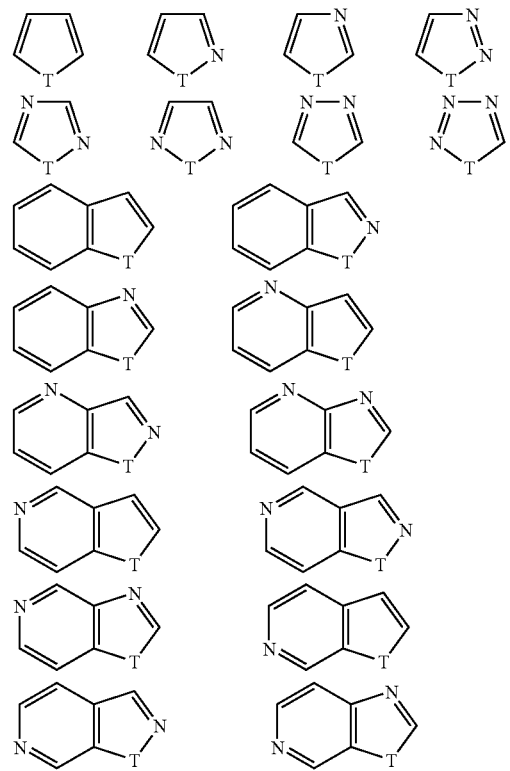

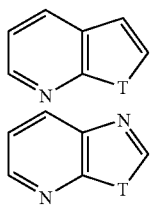 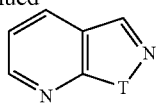

where T is O, S, NH, N-alkyl, N-aryl, or N-(arylalkyl) (e.g., N-benzyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted with up to four $R^a$ or $R^d$ groups as disclosed herein.

Compounds of the present teachings can include a "divalent group" defined herein as a linking group capable of forming a covalent bond with two other moieties. For example, compounds of the present teachings can include a divalent $C_{1-20}$ alkyl group, such as, for example, a methylene group.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19 and 20.

Compounds described herein can contain an asymmetric atom (also referred as a chiral center), and some of the compounds can contain one or more asymmetric atoms or centers, which can thus give rise to optical isomers (enantiomers) and diastereomers. The present teachings include such optical isomers (enantiomers) and diastereomers (geometric isomers), as well as the racemic and resolved, enantiomerically pure (+) and (−) stereoisomers, as well as other mixtures of the (+) and (−) stereoisomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis and trans isomers of compounds containing alkenyl moieties (e.g., alkenes and imines).

It also should be understood that the compounds of the present teachings encompass all possible regioisomers in pure form and mixtures thereof. It may be possible to separate such isomers, for example, using standard separation procedures known to those skilled in the art, for example, column chromatography, thin-layer chromatography, simulated moving-bed chromatography, and high-performance liquid chromatography. However, mixtures of regioisomers can be used similar to the uses of a specific compound of the present teachings as described herein and/or known by a skilled artisan. That is, it specifically is contemplated that the rylene compounds of the present teachings and their uses include each of the regioisomers of the rylene compounds in their pure form and mixtures thereof. For example, compounds, compositions, and devices of the present teachings can include any rylene compound in its pure form or mixtures of regio- or other isomers thereof, where the rylene compounds can be substituted with 1, 2, 3, 4, 5, 6, 7, 8, 9, 10, 11, or 12 substituents.

More specifically, the rylene compounds can include compounds having the moiety:

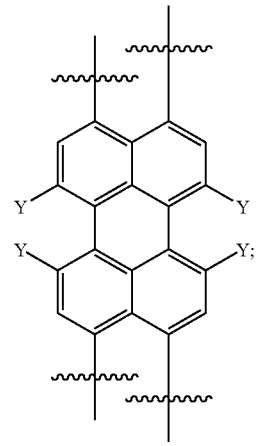

where Y, at each occurrence, can be H or $R^a$, where $R^a$ is as defined herein. In various embodiments, two of the Y groups can be H and the other two Y groups independently can be $R^a$. Accordingly, in the embodiments where two of Y groups are H and the other two are $R^a$, compounds of the present teachings can have regioisomers having the formulae:

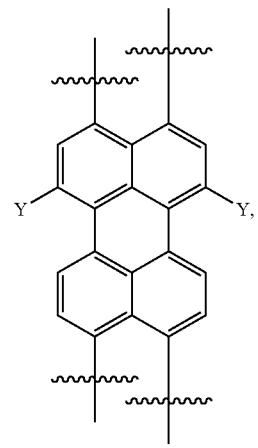

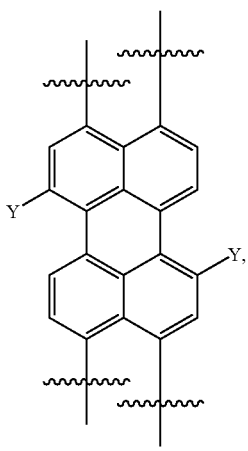
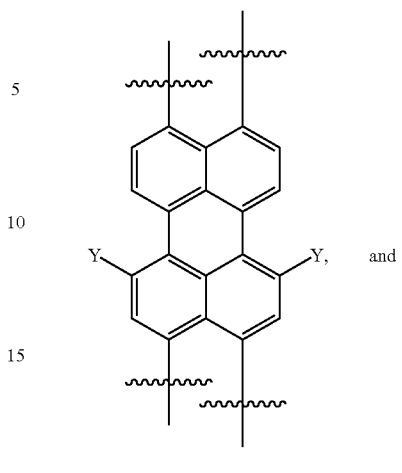
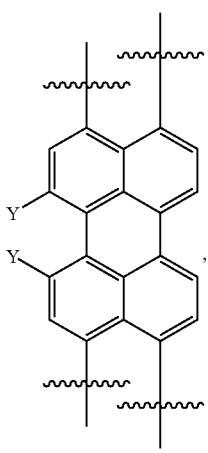
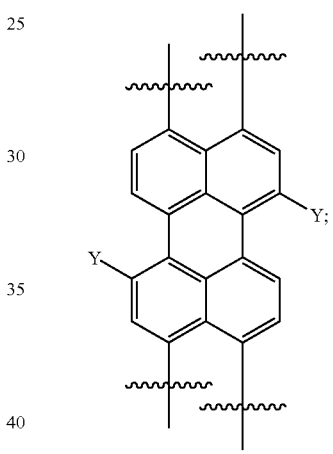
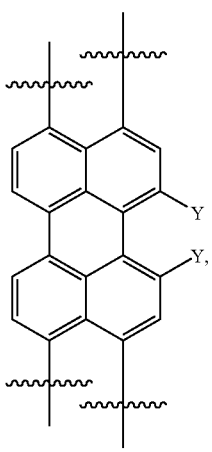
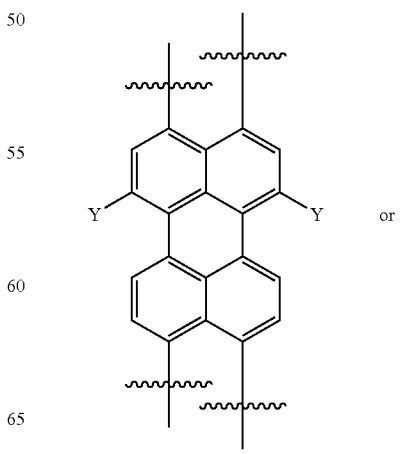
where Y, at each occurrence, can be $R^a$, where $R^a$ is as defined herein. In certain embodiments, compounds of the present teachings can include compounds having the formula:

-continued

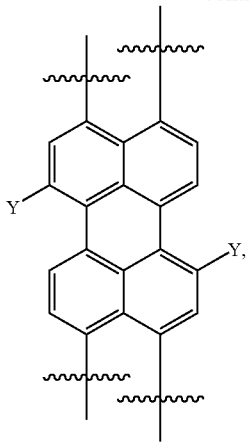

and mixtures thereof, where Y independently can be $R^a$ and $R^a$ is as defined herein, for example, a halogen such as Br or a CN group.

As used herein, a "p-type semiconducting material" or a "p-type semiconductor" refers to a semiconducting material having holes as the majority current carriers. In some embodiments, when a p-type semiconducting material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, an "n-type semiconducting material" or an "n-type semiconductor" refers to a semiconducting material having electrons as the majority current carriers. In some embodiments, when an n-type semiconducting material is deposited on a substrate, it can provide an electron mobility in excess of about $10^{-5}$ cm$^2$/Vs. In the case of field-effect devices, an n-type semiconductor can also exhibit a current on/off ratio of greater than about 10.

Throughout the specification, structures may or may not be presented with chemical names. Where any question arises as to nomenclature, the structure prevails.

One aspect of the present teachings provides a compound having the formula:

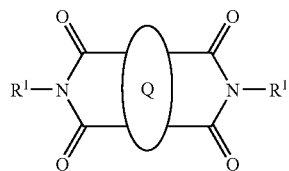

wherein:
Q is a fused ring moiety optionally substituted with 1-4 $R^a$ groups;
  wherein:
    $R^a$, at each occurrence, is independently a) a halogen, b) —CN, c) —NO$_2$, d) oxo, e) —OH, f) a C$_{1-20}$ alkyl group, g) a C$_{2-20}$ alkenyl group, h) a C$_{2-20}$ alkynyl group, i) a C$_{1-20}$ alkoxy group, j) a C$_{1-20}$ alkylthio group, k) a C$_{1-20}$ haloalkyl group, l) —Y-a C$_{3-10}$ cycloalkyl group, m) —Y-a C$_{6-14}$ aryl group, n) a —Y-3-12 membered cycloheteroalkyl group, or o) a —Y-5-14 membered heteroaryl group, wherein each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group is optionally substituted with 1-4 $R^b$ groups;
    $R^b$, at each occurrence, is independently a) a halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —N(C$_{1-20}$ alkyl)-Y—C$_{6-14}$ aryl, j) —N(—Y—C$_{6-14}$ aryl)$_2$, k) —S(O)$_m$H, l) —S(O)$_m$—C$_{1-20}$ alkyl, m) —S(O)$_2$OH, n) —S(O)$_m$—OC$_{1-20}$ alkyl, o) —S(O)$_m$—O—Y—C$_{6-14}$ aryl, p) —CHO, q) —C(O)—C$_{1-20}$ alkyl, r) —C(O)—Y—C$_{6-14}$ aryl, s) —C(O)OH, t) —C(O)—OC$_{1-20}$ alkyl, u) —C(O)—O—Y—C$_{6-14}$ aryl, v) —C(O)NH$_2$, w) —C(O)NH—C$_{1-20}$ alkyl, x) —C(O)N(C$_{1-20}$ alkyl)$_2$, y) —C(O)NH—Y—C$_{6-14}$ aryl, z) —C(O)N(C$_{1-20}$ alkyl)-Y—C$_{6-14}$ aryl, aa) —C(O)N(—Y—C$_{6-14}$ aryl)$_2$, ab) —C(S)NH$_2$, ac) —C(S)NH—C$_{1-20}$ alkyl, ad) —C(S)N(C$_{1-20}$ alkyl)$_2$, ae) —C(S)N(—Y—C$_{6-14}$ aryl)$_2$, af) c(S)N(C$_{1-20}$ alkyl)-Y—C$_{6-14}$ aryl, ag) —C(S)NH—Y—C$_{6-14}$ aryl, ah) —S(O)$_m$NH$_2$, ai) —S(O)$_m$NH(C$_{1-20}$ alkyl), aj) —S(O)$_m$N(C$_{1-20}$ alkyl)$_2$, ak) —S(O)$_m$NH(—Y—C$_{6-14}$ aryl), al) —S(O)$_m$N(C$_{1-20}$ alkyl)-Y—C$_{6-14}$ aryl, am) —S(O)$_m$N(—Y—C$_{6-14}$ aryl)$_2$, an) —SiH$_3$, ao) —SiH(C$_{1-20}$ alkyl)$_2$, ap) —SiH$_2$(C$_{1-20}$ alkyl), ar) —Si(C$_{1-20}$ alkyl)$_3$, as) a C$_{1-20}$ alkyl group, at) a C$_{2-20}$ alkenyl group, au) a C$_{2-20}$ alkynyl group, av) a C$_{1-20}$ alkoxy group, aw) a C$_{1-20}$ alkylthio group, ax) a C$_{1-20}$ haloalkyl group, ay) a —Y—C$_{3-10}$ cycloalkyl group, az) a —Y—C$_{6-14}$ aryl group, ba) a —Y-3-12 membered cycloheteroalkyl group, or bb) a —Y-5-14 membered heteroaryl group;
    Y, at each occurrence, is independently a divalent C$_{1-6}$ alkyl group, a divalent C$_{1-6}$ haloalkyl group, or a covalent bond; and
    m is 0, 1, or 2; and
$R^1$, at each occurrence, is independently a branched C$_{3-20}$ alkyl group, a branched C$_{3-20}$ alkenyl group, a branched C$_{3-20}$ haloalkyl group, -L-Ar$^1$—R$^2$, or -L-Ar$^1$—Ar$^1$—R$^2$;
  wherein:
    L, at each occurrence, is —Y—O—Y—, —Y—S—Y—, —Y—S(O)—Y—, —Y—C(O)—Y—, —Y—O—C(O)—Y—, —Y—NR$^c$C(O)—Y—, —Y—C(O)NR$^c$—Y—, —Y—NR$^c$—Y—, —Y—[SiR$_2^c$]—Y—, a divalent C$_{1-20}$ alkyl group, a divalent C$_{1-20}$ haloalkyl group, or a covalent bond;
  wherein:
    $R^c$, at each occurrence, is H, a C$_{1-6}$ alkyl group, or a —Y—C$_{6-14}$ aryl group;
    Ar$^1$, at each occurrence, is independently a C$_{6-14}$ aryl group or a 5-14 membered heteroaryl group, each optionally substituted with 1-4 $R^d$ groups;
  wherein:
    $R^d$, at each occurrence, is independently selected from a halogen, —CN, a C$_{1-6}$ alkyl group, a C$_{1-6}$ alkoxy group, and a C$_{1-6}$ haloalkyl group; and
    $R^2$, at each occurrence, is H, a halogen, a C$_{1-20}$ alkyl group, a C$_{2-20}$ alkenyl group, a C$_{1-20}$ haloalkyl group, a C$_{1-20}$ alkoxy group, -L'-Ar$^2$—R$^3$, or -L'-Ar$^2$—Ar$^2$—R$^3$;
  wherein:
    L' is —Y—O—Y—, —Y—S—Y—, —Y—S(O)—Y—, —Y—C(O)—Y—, —Y—O—C(O)—Y—, —Y—NR$^c$C(O)—Y—, —Y—C(O)NR$^c$—Y—, —Y—NR$^c$—Y—, —Y—[SiRC$_2$]—Y—, a divalent C$_{1-20}$ alkyl group, a divalent C$_{1-20}$ haloalkyl group, or a covalent bond;
    Ar$^2$, at each occurrence, is independently a C$_{6-14}$ aryl group or a 5-14 membered heteroaryl group, each optionally substituted with 1-4 $R^d$ groups; and $R^3$, at each occurrence, is H, a halogen, a $C_{1-20}$ alkyl group, a $C_{2-20}$ alkenyl group, a $C_{1-20}$ haloalkyl group, or a $C_{1-20}$ alkoxy group.

In some embodiments, Q can be:

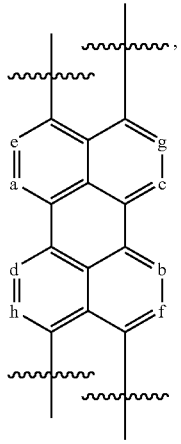
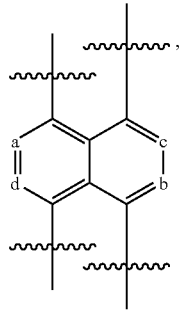

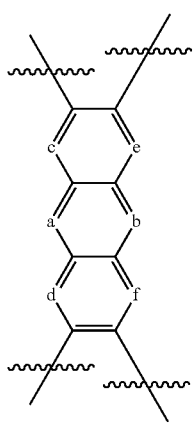    or

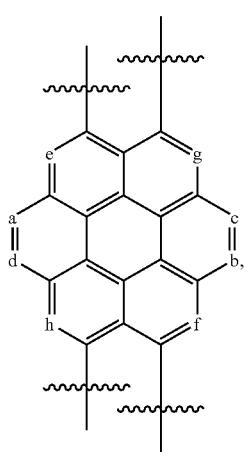

where a, b, c, d, e, f, g and h are independently CH, $CR^a$, SiH, $SiR^a$, N or P; and $R^a$ is as defined herein. For example, a, b, c, d, e, f, g and h can be independently CH, C(Br), or C(CN).

In particular embodiments, a compound of the present teachings can have the formula:

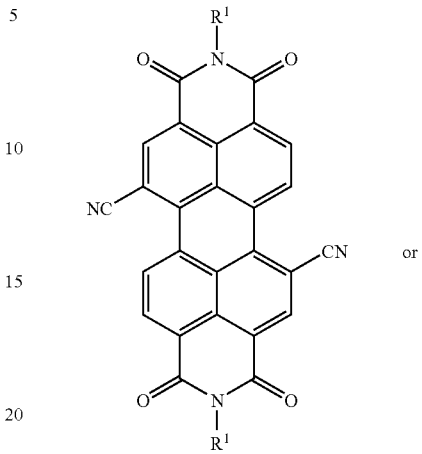

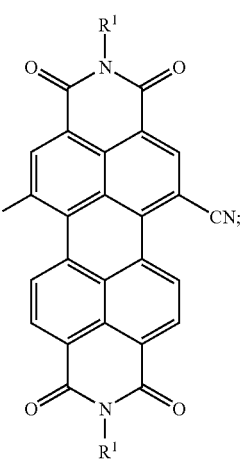

where $R^1$ is as defined herein. For example, in certain embodiments, each $R^1$ independently can be a 3-alkyl substituted alkyl group or a 3-alkyl substituted alkenyl group such as the 3,7-dialkyl substituted alkyl group and the 3,7-dialkyl substituted alkenyl group, respectively, depicted below:

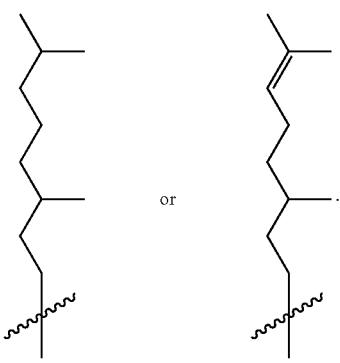

In particular embodiments of the immediately above compounds, each $R^1$ independently can be a 2-alkyl substituted alkyl group. For example, each $R^1$ independently can be a 2-$C_{1-20}$ alkyl group($C_{3-20}$ alkyl group), a 2-$C_{1-20}$ alkyl group ($C_{3-10}$ alkyl group), a 2-$C_{1-20}$ alkyl group($C_{3-8}$ alkyl group), a 2-$C_{1-10}$ alkyl group($C_{3-20}$ alkyl group), a 2-$C_{1-10}$ alkyl group ($C_{3-10}$ alkyl group), a 2-$C_{1-10}$ alkyl group($C_{3-8}$ alkyl group), a 2-$C_{1-8}$ alkyl group($C_{3-20}$ alkyl group), a 2-$C_{1-8}$ alkyl group ($C_{3-10}$ alkyl group), a 2-$C_{1-8}$ alkyl group($C_{3-8}$ alkyl group), a 2-$C_{1-6}$ alkyl group($C_{3-20}$ alkyl group), a 2-$C_{1-6}$ alkyl group ($C_{3-10}$ alkyl group), or a 2-$C_{1-6}$ alkyl group($C_{3-8}$ alkyl group). In certain embodiments, each $R^1$ independently can be 2-methylpropyl, 2-ethylpropyl, 2-propylpropyl, 2-butylpropyl, 2-pentylpropyl, 2-hexylpropyl, 2-methylbutyl, 2-ethylbutyl, 2-propylbutyl, 2-butylbutyl, 2-pentylbutyl, 2-hexylbutyl, 2-methylpentyl, 2-ethylpentyl, 2-propylpentyl, 2-butylpentyl, 2-pentylpentyl, 2-hexylpentyl, 2-methylhexyl, 2-ethylhexyl, 2-propylhexyl, 2-butylhexyl, 2-pentylhexyl, 2-hexylhexyl, 2-methylheptyl, 2-ethylheptyl, 2-propylheptyl, 2-butylheptyl, 2-pentylheptyl, 2-hexylheptyl, 2-methyloctyl, 2-ethyloctyl, 2-propyloctyl, 2-butyloctyl, 2-pentyloctyl, 2-hexyloctyl, 2-methylnonyl, 2-ethylnonyl, 2-propylnonyl, 2-butylnonyl, 2-pentylnonyl, 2-hexylnonyl, 2-methyldecyl, 2-ethyldecyl, 2-propyldecyl, 2-butyldecyl, 2-pentyldecyl, or 2-hexyldecyl.

In certain embodiments, a compound of the present teachings can have the formula:

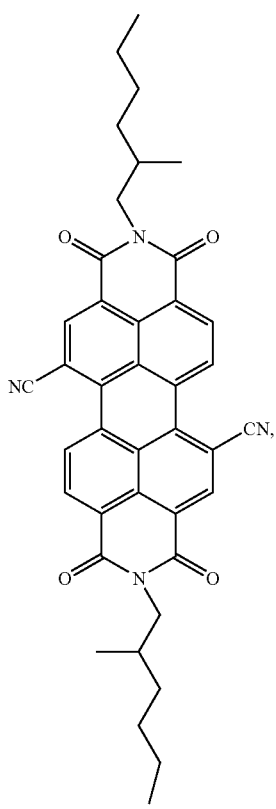

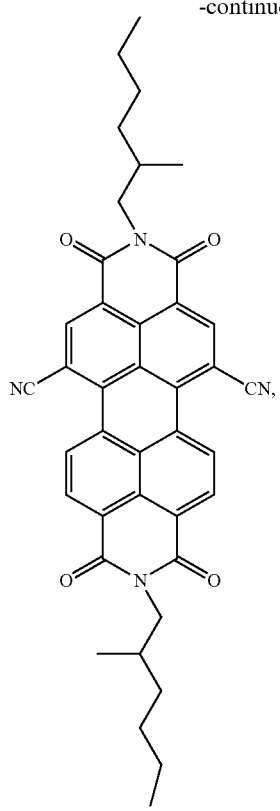

-continued

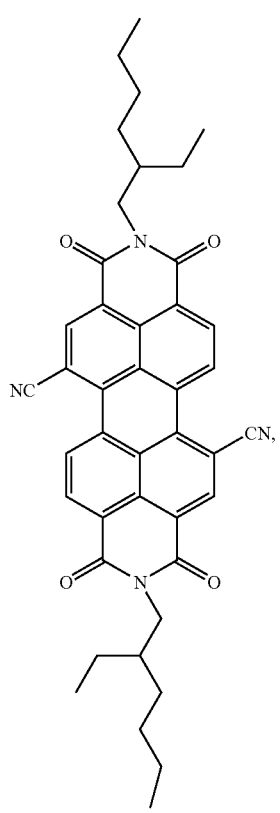

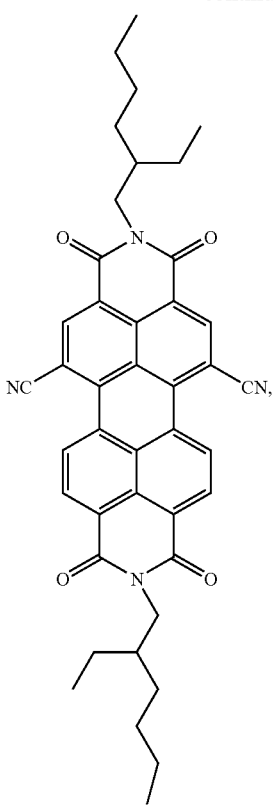

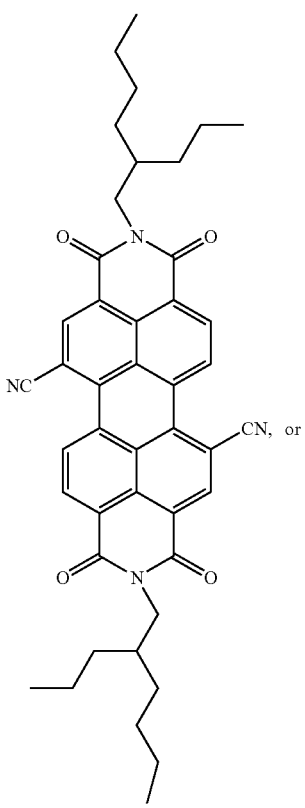

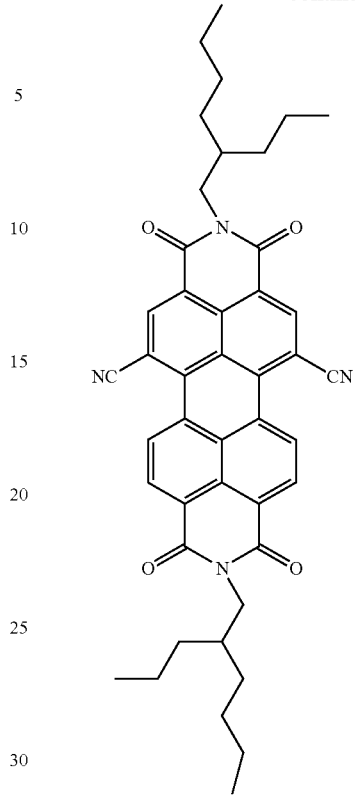

including mixtures thereof, particularly of the cis and trans isomers having the same imide nitrogen substitution.

Without wishing to be bound to any particular theory, it is believed that the intermolecular core-core stacking of the individual rylene imide compounds is important for efficient charge transport. It is further believed that by functionalizing the imide groups with relatively rigid aromatic units (e.g., $Ar^1$, $Ar^2$) connected to the core and/or to each other by relatively flexible linkers (e.g., L and L'), the solubility as well as the microstructural ordering of these rylene imide compounds can be enhanced. Without wishing to be bound to any particular theory, enhanced microstructural order is believed to promote charge mobility.

Accordingly, in some embodiments, each $R^1$ can be -L-$Ar^1$—$R^2$ or -L-$Ar^1$—$Ar^1$—R; where L, $Ar^1$ and $R^2$ are as defined herein. For example, each $R^1$ can be:

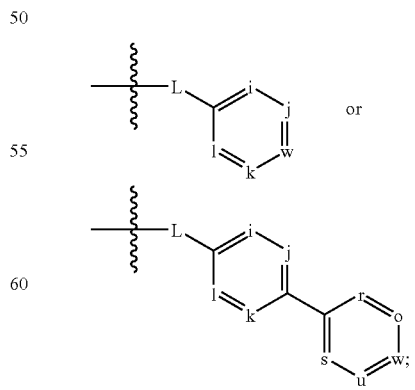

where i, j, k, l, o, r, s and u independently can be CH, $CR^d$, SiH, $SiR^d$, N or P, w can be CH, $CR^2$, SiH, $SiR^2$, N or P; and L, $R^2$ and $R^d$ are as defined herein. In particular embodiments, i, j, k, l, o, r, s and u independently can be CH, CF, or N, and w can be $CR^2$. For example, each $R^1$ can be:

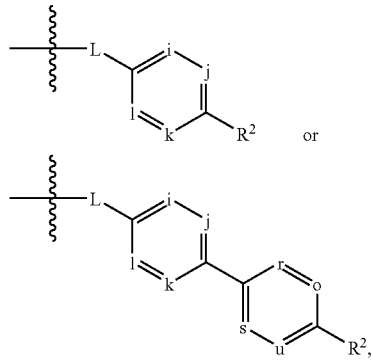

where L and $R^2$ are as defined herein. For example, L can be a divalent $C_{1-10}$ alkyl group, a divalent $C_{1-10}$ haloalkyl group, or a covalent bond.

In some embodiments, $R^2$ can be H, F, a $C_{1-20}$ alkyl group, a $C_{2-20}$ alkenyl group, a $C_{1-20}$ haloalkyl group, or a $C_{1-20}$ alkoxy group. For example, $R^2$ can be a straight chain $C_{1-20}$ alkyl group, a branched $C_{3-20}$ alkyl group, a branched $C_{3-20}$ alkenyl group, a $C_{1-20}$ fluoroalkyl group, or a $C_{1-20}$ alkoxy group. In particular embodiments, each $R^2$ can be an n-butyl group, a sec-butyl group, a hexyl group, an octyl group, a dodecanyl group, a tridecanyl group, a decenyl group, an —O-dodecanyl group, or an —O-tridecanyl group. In certain embodiments, each $R^2$ can be:

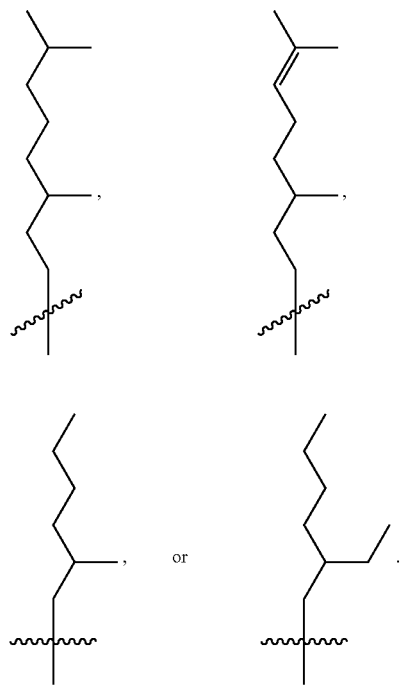

In other embodiments, each $R^2$ can be -L'-$Ar^2$—$R^3$ or -L'-$Ar^2$—$Ar^2$—$R^3$; where L', $Ar^2$ and $R^3$ are as defined herein. For example, each $R^1$ can be:

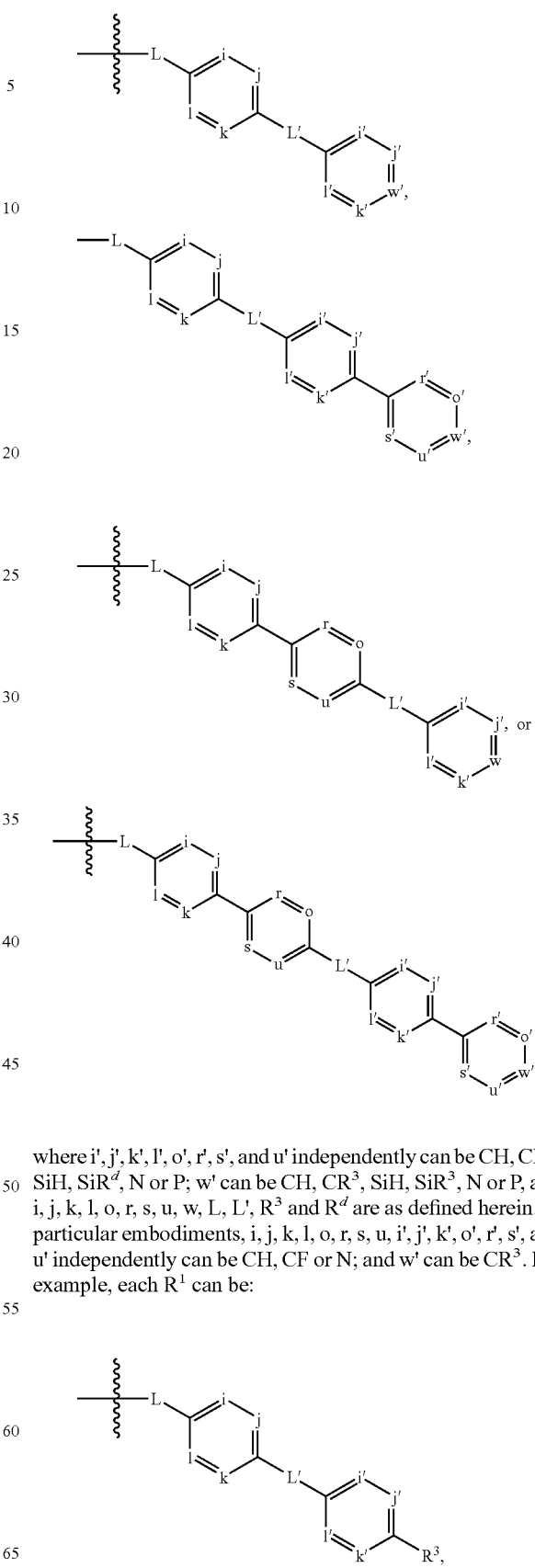

where i', j', k', l', o', r', s', and u' independently can be CH, $CR^d$, SiH, $SiR^d$, N or P; w' can be CH, $CR^3$, SiH, $SiR^3$, N or P, and i, j, k, l, o, r, s, u, w, L, L', $R^3$ and $R^d$ are as defined herein. In particular embodiments, i, j, k, l, o, r, s, u, i', j', k', o', r', s', and u' independently can be CH, CF or N; and w' can be $CR^3$. For example, each $R^1$ can be:

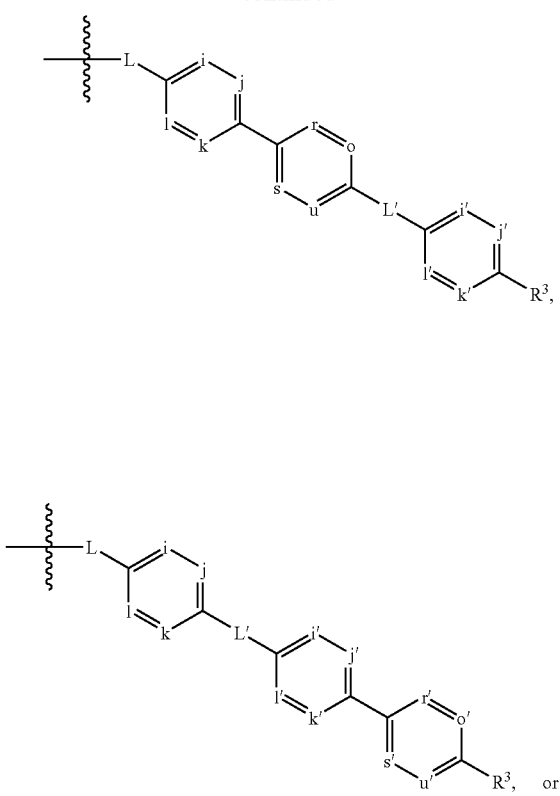

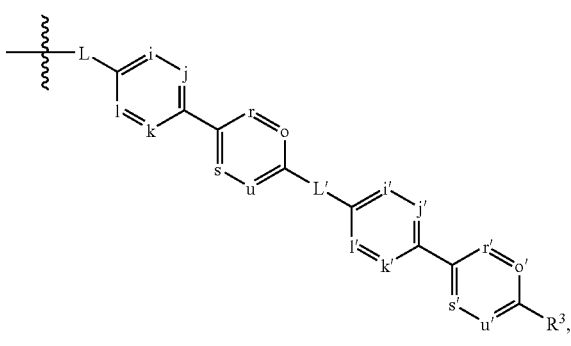

where L, L', and R³ are as defined herein. For example, L can be a divalent $C_{1-10}$ alkyl group, a divalent $C_{1-10}$ haloalkyl group, or a covalent bond; and L' can be —C(O)—, —O—, —S—, or —S(O)—, a divalent $C_{1-10}$ alkyl group, a divalent $C_{1-10}$ haloalkyl group, or a covalent bond.

In some embodiments, R³ can be H, F, a $C_{1-20}$ alkyl group, a $C_{2-20}$ alkenyl group, a $C_{1-20}$ haloalkyl group, or a $C_{1-20}$ alkoxy group. In certain embodiments, R³ can be a straight chain $C_{1-20}$ alkyl group, a branched $C_{3-20}$ alkyl group, a branched $C_{3-20}$ alkenyl group, a $C_{1-20}$ fluoroalkyl group, or a $C_{1-20}$ alkoxy group. In particular embodiments, each R³ can be an n-butyl group, a sec-butyl group, a hexyl group, an octyl group, a dodecanyl group, a tridecanyl group, a decenyl group, an —O-dodecanyl group, or an —O-tridecanyl group. For example, each R³ can be:

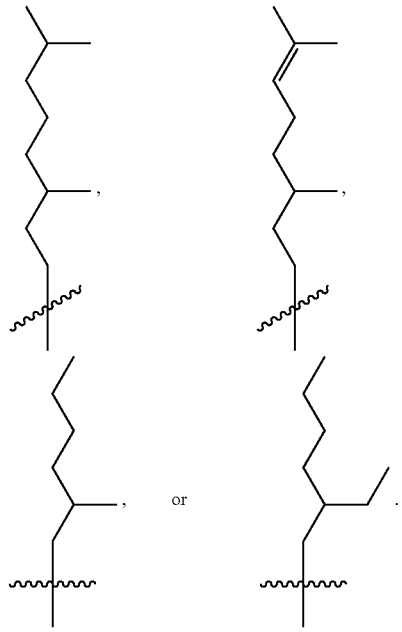

In some embodiments, each R¹ can be an aryl group, a biaryl group, an arylalkyl group, or a biarylalkyl group, where each of the aryl groups can be optionally substituted with 1-4 groups independently selected from $R^d$ and R² group. In certain embodiments, each R¹ can have the formula below:

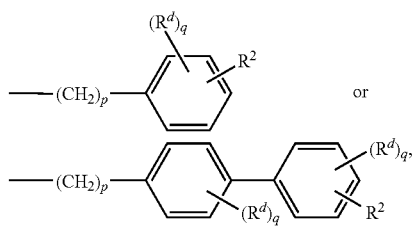

where p is an integer in the range of 0 to 20, q is an integer in the range of 0 to 4, and R² and $R^d$ are as defined herein.

For example, each R¹ can be a benzyl group, a biphenyl group, or a fluoro-substituted biphenyl group as shown below:

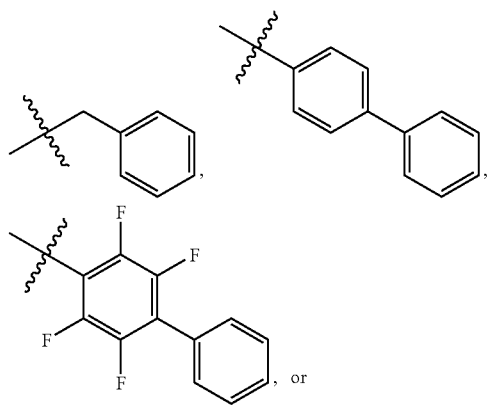

-continued

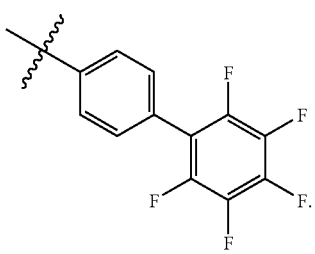

In some embodiments, the benzyl group, the biphenyl group, and the fluoro-substituted biphenyl group can be further substituted with an -L'-aryl group or an -L'-biaryl group, where each of the aryl groups can be optionally substituted with 1-4 $R^d$ groups and an $R^3$ group. In certain embodiments, each $R^1$ can be selected from:

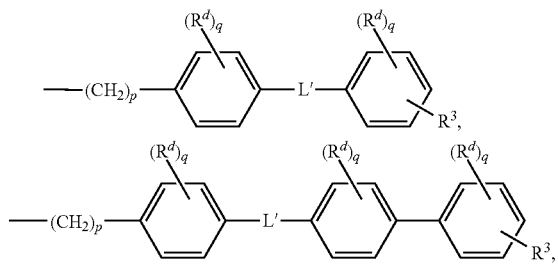

-continued

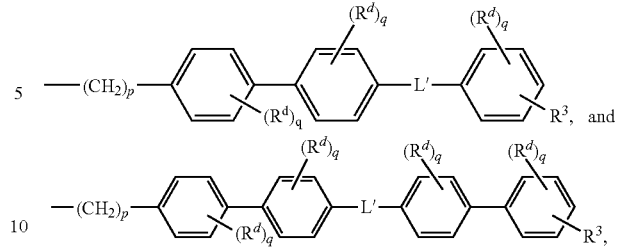

where L', $R^d$, $R^3$, p and q are as defined herein.
In particular embodiments, $R^1$ can be:

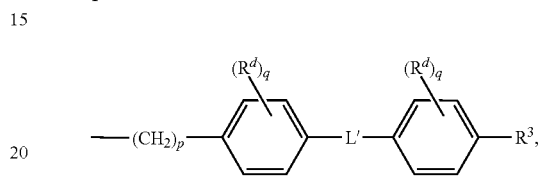

where L', $R^d$, $R^3$, p and q are as defined herein. For example, $R^d$ can be F; p can be 0, 1 or 2; each q independently can be 0 or 4; L' can be —CH$_2$—, —CH$_2$CH$_2$—, —C(O)—, —O—, —S—, or —S(O)—; and $R^3$ can be H, F, or a methyl group.

Although the functional groups substituted at the nitrogen atom of each imide group can be different, in most embodiments, the two imide groups are substituted with $R^1$ groups that are the same.

Compounds of the present teachings include, but are not limited to, the compounds presented in Tables 1 and 2 below.

TABLE 1

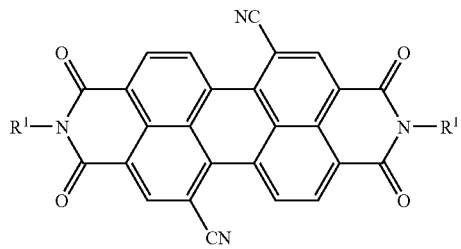

| | | |
|---|---|---|
| 1 | N,N'-bis[(3S)-3,7-dimethyl-6-octenyl]-1,7-dicyanoperylene-3,4:9,10-bis(dicarboxiamide) (PDICitr-CN$_2$) | 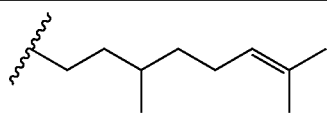 |
| 2 | N,N'-bis(4-n-hexylphenyl)-1,7-dicyanoperylene-3,4:9,10-bis(dicarboxiamide) (PDIPh6-CN$_2$) | 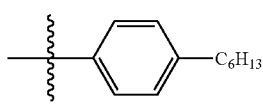 |
| 3 | N,N'-bis(4-n-dodecylphenyl)-1,7-dicyanoperylene-3,4:9,10-bis(dicarboxiamide) (PDIPh12-CN$_2$) | 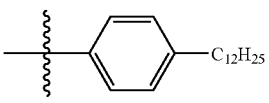 |
| 4 | N,N'-bis{4-[(3S)-3,7-dimethyl-6-octenyl]phenyl}-1,7-dicyanoperylene-3,4:9,10-bis(dicarboxiamide) (PDIPhCitr-CN$_2$) | 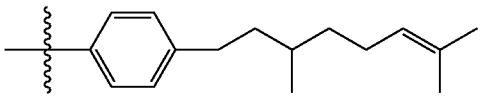 |
| 5 | N,N'-bis(4-heptyloxyphenyl)-1,7-dicyanoperylene-3,4:9,10-bis(dicarboxiamide) (PDIPhO7-CN$_2$) | 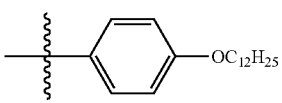 |

TABLE 1-continued

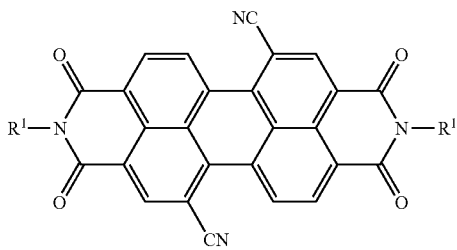

| | | |
|---|---|---|
| 6 | N,N'-bis(4-biphenylyl)-1,7-dicyanoperylene-3,4:9,10-bis(dicarboxiamide) (PDIPhPh-CN$_2$) | |
| 7 | N,N'-bis[4-(4'-n-octylbiphenylyl)]-1,7-dicyanoperylene-3,4:9,10-bis(dicarboxiamide) (PDIPhPh8-CN$_2$) | |
| 8 | N,N'-bis{4-[4'-((3S)-3,7-dimethyl-6-octenyl]biphenylyl}-1,7-dicyanoperylene-3,4:9,10-bis(dicarboxiamide) (PDIPhPhCitr-CN$_2$) | |
| 9 | N,N'-bis[4-(2',3',4',5',6'-pentafluorobiphenyl)]-1,7-dibromoperylene-3,4:9,10-bis(dicarboxiamide) (PDIPhPh$^F$-CN$_2$) | |
| 10 | N,N'-bis[4-(4'-n-octyl-2',3',5',6'-tetrafluorobiphenyl)]-1,7-dicyanoperylene-3,4:9,10-bis(dicarboxiamide) (PDIPhPh$^F$8-CN$_2$) | |
| 11 | N,N'-bis[4-(4'-n-octyl-2,3,5,6-tetrafluorobiphenyl)]-1,7-dicyanoperylene-3,4:9,10-bis(dicarboxiamide) (PDIPh$^F$Ph8-CN$_2$) | |
| 12 | N,N'-bis(benzyl)-1,7-dicyanoperylene-3,4:9,10-bis(dicarboxiamide) (PDI1Ph-CN$_2$) | |
| 13 | N,N'-bis(4-n-butylbenzyl)-1,7-dicyanoperylene-3,4:9,10-bis(dicarboxiamide) (PDI1Ph4-CN$_2$) | |
| 14 | N,N'-bis(4-sec-butylphenyl)-1,7-dicyanoperylene-3,4:9,10-bis(dicarboxiamide) (PDIPhs4-CN$_2$) | |
| 15 | N,N'-bis{4-[(3S)-3,7-dimethyl-6-octenyloxy]benzyl}-1,7-dicyanoperylene-3,4:9,10-bis(dicarboxiamide) (PDI1PhOCitr-CN$_2$) | |
| 16 | N,N'-bis(4-benzylphenyl)-1,7-dicyanoperylene-3,4:9,10-bis(dicarboxiamide) (PDIPh1Ph-CN$_2$) | |

TABLE 1-continued

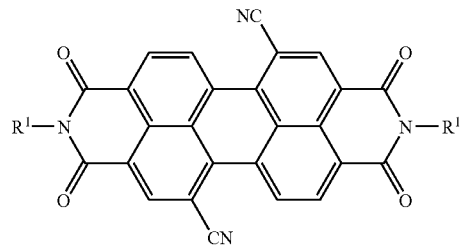

17 N,N'-bis{4-[1-(2-phenylethyl)]phenyl}-1,7-dicyanoperylene-3,4:9,10-bis(dicarboxiamide) (PDIPh2Ph-CN$_2$)

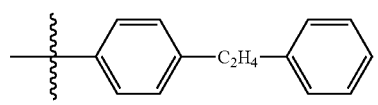

18 N,N'-bis(4-n-benzoylphenyl)-1,7-dicyanoperylene-3,4:9,10-bis(dicarboxiamide) (PDIPhCOPh-CN$_2$)

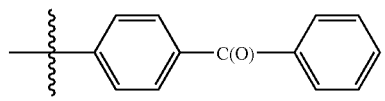

19 N,N'-bis(2-methylhexyl)-1,7-dicyanoperylene-3,4:9,10-bis(dicarboxiamide) (PDI2MH-CN$_2$)

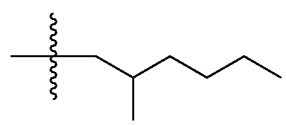

20 N,N'-bis(2-ethylhexyl)-1,7-dicyanoperylene-3,4:9,10-bis(dicarboxiamide) (PDI2EH-CN$_2$)

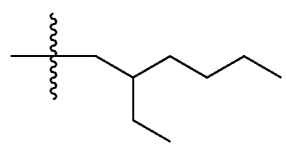

TABLE 2

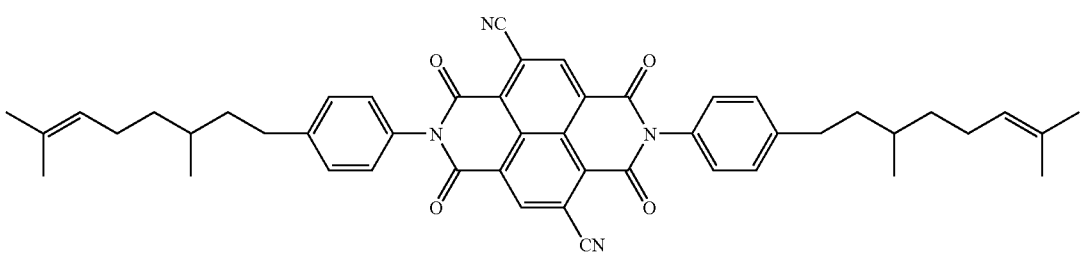

21  N,N'-{4-[(3S)-3,7-dimethyl-6-octenyl]phenyl}-2,6-dicyanonapthalene-1,4:5,8-tetracarboxylicdiimide (NDICitr-CN$_2$)

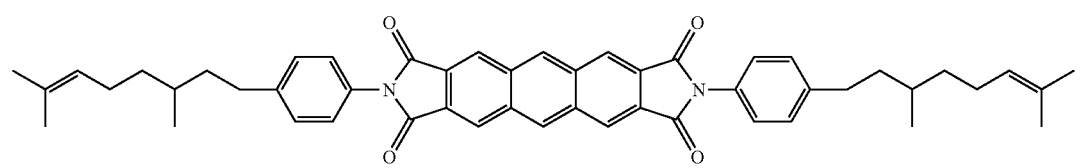

22  N,N-bis{4-[(3S)-3,7-dimethyl-6-octenyl]phenyl}-2,3:6,7-anthracenedicarboximide The present teachings also provide compounds related to those disclosed herein, including those having the formula:

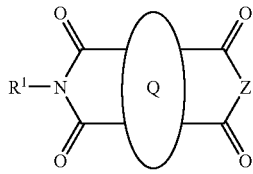

where Z can be O, S, S(O), C(O) or CR$^e$R$^f$; and R$^e$ and R$^f$ are independently a) H, b) a halogen, c) —(CH$_2$CH$_2$O)$_x$H, d) —CH$_2$CH$_2$O)$_x$—CH$_3$, e) a C$_{1-20}$ alkoxy group, f) a C$_{1-20}$ alkyl group, g) a C$_{2-20}$ alkenyl group, h) a C$_{2-20}$ alkynyl group, i) a —Y—C$_{3-10}$ cycloalkyl group, j) a —Y—C$_{6-14}$ aryl group, k) a —Y-3-12 membered cycloheteroalkyl group, or l) a —Y-5-14 membered heteroaryl group, where each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group can be optionally substituted with 1-4 R$^a$ groups; x is an integer in the range of 1 to 20, and Q, R$^1$, R$^a$, and Y are as defined herein.

As certain embodiments of the compounds disclosed herein can be soluble in common solvents, compounds of the present teachings can offer processing advantages when used to fabricate electrical devices, optical devices, and optoelectronic devices such as thin film transistors, field-effect devices, organic light emitting diodes (OLEDs), organic photovoltaics, photodetectors, capacitors, and sensors. As used herein, a compound can be considered soluble in a solvent when at least 1 mg of the compound is soluble in 1 mL of the solvent. Examples of common organic solvents include petroleum ethers; acetonitrile; aromatic hydrocarbons such as benzene, toluene, xylene, and mesitylene; linear and cyclic ketones, such as acetone, methyl ethyl ketone, and cyclopentanone; ethers, such as tetrahydrofuran, dioxane, bis(2-methoxyethyl)ether, diethyl ether, di-isopropyl ether, and t-butyl methyl ether; alcohols, such as methanol, ethanol, butanol, and isopropyl alcohol; aliphatic hydrocarbons, such as hexanes; acetates, such as methyl acetate, ethyl acetate, methyl formate, ethyl formate, isopropyl acetate, and butyl acetate; halogenated aliphatic and aromatic hydrocarbons, such as dichloromethane, chloroform, ethylene chloride, chlorobenzene, dichlorobenzene, trichlorobenzene, and fluorobenzene; and cyclic solvents such as cyclopentanone, cyclohexanone, and 2-methypyrrolidone. Examples of common inorganic solvents include water and ionic liquids.

Accordingly, the present teachings further provide compositions that comprise one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, such compositions can include one or more compounds disclosed herein, for example, one or more different compounds of the present teachings can be dissolved in an organic solvent to prepare a composition for deposition. In certain embodiments, the composition can include two or more regioisomers, for example, compounds having the formulae:

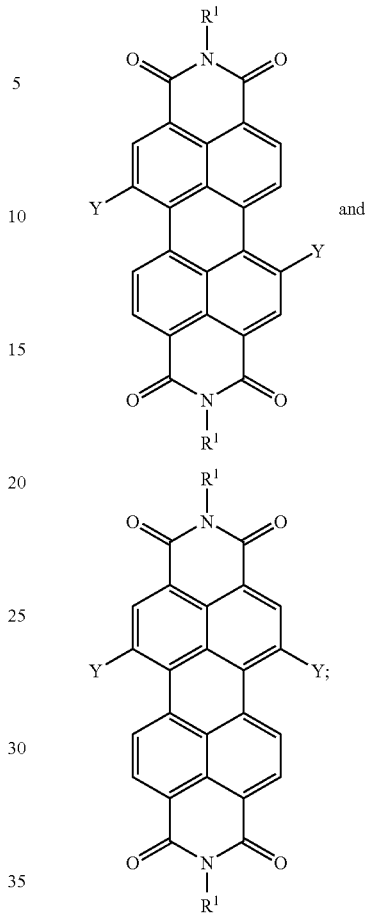

where Y and R$^1$ are as defined herein, for example, each Y independently can be CN or a halogen such as Br. Further, it should be understood that the devices described herein also can comprise more or more compounds of the present teachings, for example, two or more regioisomers as described herein.

In particular embodiments, the composition can include two or more regioisomers having the formulae:

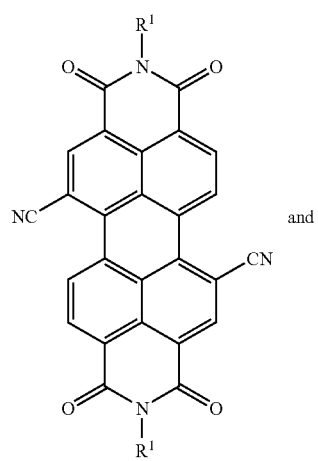

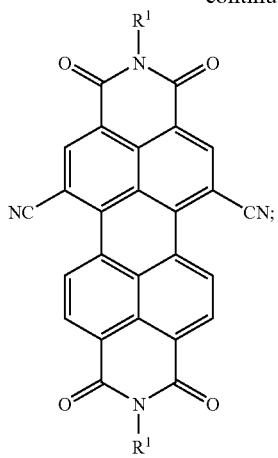

where R[1] is as defined herein. In various embodiments, each R[1] independently is a 2-alkyl substituted alkyl group as discussed and defined above. For example, each R[1] independently can be 2-methylpentyl, 2-ethylpentyl, 2-propylpentyl, 2-butylpentyl, 2-pentylpentyl, 2-hexylpentyl, 2-methylhexyl, 2-ethylhexyl, 2-propylhexyl, 2-butylhexyl, 2-pentylhexyl, 2-hexylhexyl, 2-methylheptyl, 2-ethylheptyl, 2-propylheptyl, 2-butylheptyl, 2-pentylheptyl, or 2-hexylheptyl.

The present teachings further provide methods of preparing a semiconductor such as a thin film semiconductor or a semiconductor material. The methods can include preparing a composition that includes one or more compounds (e.g., a mixture of regioisomers) disclosed herein in a liquid medium such as an organic solvent, an inorganic solvent or a mixture of solvents, and depositing the composition on a substrate to provide a semiconductor that includes one or more compounds disclosed herein.

Various deposition techniques, including various solution processing techniques, have been used with organic electronics. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include, but are not limited to, screen-printing, gravure, offset, pad, and microcontact printing. Other solution processing techniques include, for example, spin coating, drop-casting, zone casting, dip coating, blade coating, or spraying. In addition, the depositing step can be carried out by vacuum vapor deposition.

Various articles of manufacture including electronic devices, optical devices, and optoelectronic devices such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the compounds disclosed herein also are within the scope of the present teachings as are methods of making the same.

The present teachings provide articles of manufacture such as the various devices described herein that include a composite, which has one or more compounds of the present teachings deposited on a substrate. The article of manufacture can include a dielectric component. The substrate can be selected from materials including doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., the crosslinked polymer blends described in U.S. patent application Ser. Nos. 11/315,076, 60/816,952, and 60/861,308, the entire disclosure of each of which is incorporated by reference herein) and a self-assembled superlattice/self-assembled nanodielectric (SAS/SAND) material (described in Yoon, M-H. et al., *PNAS*, 102 (13): 4678-4682 (2005), the entire disclosure of which is incorporated by reference herein), as well as a hybrid organic/inorganic dielectric material (described in U.S. patent application Ser. No. 11/642,504, the entire disclosure of which is incorporated by reference herein). The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, solar cells, capacitors, complementary circuits (e.g., inverter circuits), and the like.

Another article of manufacture in which compounds of the present teachings are useful is photovoltaics or solar cells. Compounds of the present teachings can exhibit relatively broad optical absorption and/or a positively shifted reduction potential making them desirable for such applications. Accordingly, the compounds described herein can be used as a n-type semiconductor in a photovoltaic design, which includes an adjacent p-type semiconducting material that forms a p-n junction. The compounds can be in the form of a thin film semiconductor, which can be a composite of the thin film semiconductor deposited on a substrate. Exploitation of compounds of the present teachings in such devices is within the knowledge of the skilled artisan.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

In certain embodiments, OTFT devices can be fabricated with the present compounds on doped silicon substrates, using $SiO_2$ as the dielectric, in top-contact geometries. In particular embodiments, the active semiconducting layer which incorporates at least a compound of the present teachings can be deposited by vacuum vapor deposition at room temperature or at an elevated temperature. In other embodiments, the active semiconducting layer which incorporates at least a compound of the present teachings can be applied by spin-coating or jet printing. For top-contact devices, metallic contacts can be patterned on top of the films using shadow masks.

The following examples are provided to illustrate further and to facilitate the understanding of the present teachings and are not in any way intended to limit the invention.

Unless otherwise noted, all reagents were purchased from commercial sources and used without further purification. Some reagents were synthesized according to known procedures. Anhydrous tetrahydrofuran (THF) was distilled from sodium/benzophenone. Conventional Schlenk techniques were used, and reactions were carried out under nitrogen unless otherwise noted. UV-vis spectra were recorded on a Cary Model 1 UV-vis spectrophotometer. NMR spectra were recorded on a Varian Unity Plus 500 spectrometer ($^1$H, 500 MHz; $^{13}$C, 125 MHz). Electrospray mass spectrometry was performed with a Thermo Finnegan model LCQ Advantage mass spectrometer.

Example 1

Preparation of N,N'-bis[(3S)-3,7-dimethyl-6-octenyl]-1,7-dicyanoperylene-3,4:9,10-bis(dicarboxiamide) (PDICitr-CN$_2$)

Part A: Preparation of N,N'-bis[(3S)-3,7-dimethyl-6-octenyl]-1,7-dibromoperylene-3,4:9,10-bis(dicarboxiamide) (PDICitr-Br$_2$ Citronellylamine (5.00 g, 31.8 mmol) was added to a suspension of 1,7-dibromoperylene-3,4:9,10-dianhydride (PDABr$_2$) (4.37 g, 7.95 mmol) in propionic acid (50 mL). The reaction mixture was heated under reflux for 12 hours. After cooling to room temperature, the resulting solid was collected by filtration, washed with propionic acid and several times with methanol (MeOH), and finally dried overnight. The crude product (4.71 g) was purified by chromatography on silica gel (dichloromethane, CH$_2$Cl$_2$) to give N,N'-bis[(3S)-3,7-dimethyl-6-octenyl]-1,7-dibromoperylene-3,4:9,10-bis(dicarboxiamide) as a red solid (0.70 g, 0.85 mmol, 10.7% yield).

M.p.=270-272° C. (DMF); $^1$H NMR (CHCl$_3$, 400 MHz): δ 9.50 (d, 2H, J=7.5 Hz), 8.94 (s, 2H), 8.72 (d, 2H, J=6.5 Hz), 5.13 (t, 2H, J=7.0 Hz), 4.33-4.20 (m, 4H), 2.15-1.96 (m, 4H), 1.80-1.70 (m, 4H), 1.68 (s, 6H), 1.62 (s, 6H), 1.52-1.40 (m, 4H), 1.36-1.20 (m, 4H), 1.05 (t, 6H, J=6.5 Hz); Elemental Analysis (calculated for C$_{44}$H$_{44}$Br$_2$N$_2$O$_4$: C, 64.09; H, 5.38; N, 3.40): C, 63.06; H, 5.21; N, 2.79.

Part B: Preparation of N,N'-bis[(3S)-3,7-dimethyl-6-octenyl]-1,7-dicyanoperylene-3,4:9,10-bis(dicarboxiamide) (PDICitr-CN$_2$)

A mixture of N,N'-bis(citronellyl)-1,7-dibromoperylene-3,4:9,10-bis(dicarboxiamide) (0.70 g, 0.85 mmol) and copper (I) cyanide (CuCN, 0.38 g, 15.4 mmol) in dimethylformamide (DMF, 35 mL) was deaerated and placed under nitrogen. The reaction mixture was heated at 150° C. for 6 hours. After cooling to room temperature, the precipitate was collected by filtration, washed several times with MeOH, and dried overnight. The crude solid was purified by chromatography on silica gel (CH$_2$Cl$_2$:acetone—95:5) to give N,N'-bis[(3S)-3,7-dimethyl-6-octenyl]-1,7-dibromoperylene-3,4:9, 10-bis(dicarboxiamide) as a red powder (0.34 g, 0.47 mmol, 55.3% yield).

M.p.=277-279° C. (DMF); $^1$H NMR(CHCl$_3$, 500 MHz): δ 9.69 (d, 2H, J=8.0 Hz), 8.97 (s, 2H), 8.92 (d, 2H, J=8.0 Hz), 5.12 (t, 2H, J=7.0 Hz), 4.28-4.21 (m, 4H), 2.10-1.96 (m, 4H), 1.80-1.70 (m, 4H), 1.68 (s, 6H), 1.62 (s, 6H), 1.50-1.43 (m, 4H), 1.34-1.24 (m, 4H), 1.06 (d, 6H, J=6.5 Hz); Elemental Analysis (calculated for C$_{46}$H$_{44}$N$_4$O$_4$: C, 77.07; H, 6.19; N, 7.82): C, 77.39; H, 6.18; N, 7.99.

Example 2

Preparation of N,N'-bis(4-n-hexylphenyl)-1,7-dicyanoperylene-3,4:9,10-bis(dicarboxiamide) (PDIPh6-CN$_2$)

Part A: Preparation of N,N'-bis(4-n-hexylphenyl)-1,7-dibromoperylene-3,4:9,10-bis(dicarboxiamide) (PDIPh6-Br$_2$)

4-n-Hexylaniline (3.39 g, 19.12 mmol) was added to a suspension of 1,7-dibromoperylene-3,4:9,10-dianhydride (4.00 g, 4.78 mmol) in propionic acid (40 mL). The reaction mixture was heated under reflux for 12 hours. After cooling to room temperature, the resulting solid was collected by filtration, washed with propionic acid and several times with MeOH, and finally dried overnight. The crude product (4.38 g) was purified by chromatography on silica gel (chloroform:acetone—50:50) to give N,N'-bis(4-n-hexylphenyl)-1,7-dibromoperylene-3,4:9,10-bis(dicarboxiamide) as a red solid (1.49 g, 1.72 mmol, 36.0% yield).

M.p.>250° C. (DMF); $^1$H NMR (CHCl$_3$, 400 MHz): δ 9.54 (d, 2H, J=8.0 Hz), 8.96 (s, 2H), 8.76 (d, 2H, J=8.0 Hz), 7.40 (d, 4H, J=8.0 Hz), 7.24 (d, 4H, J=8.0 Hz), 2.72 (t, 4H, J=8.0 Hz), 1.75-1.67 (m, 4H), 1.48-1.40 (m, 4H), 1.40-1.26 (m, 8H), 0.93 (t, 6H, J=7.6 Hz); Elemental Analysis (calculated for C$_{48}$H$_{40}$Br$_2$N$_2$O$_4$; C, 66.37; H, 4.64; N, 3.22): C, 65.87; H, 4.44; N, 2.91.

Part B: Preparation of N,N'-bis(4-n-hexylphenyl)-1,7-dicyanoperylene-3,4:9,10-bis(dicarboxiamide) (PDIPh6-CN$_2$)

A mixture of N,N'-bis(4-n-hexylphenyl)-1,7-dibromoperylene-3,4:9,10-bis(dicarboxiamide) (1.39 g, 1.60 mmol) and CuCN (2.68 g, 30.0 mmol) in DMF (65 mL) was deaerated and placed under nitrogen. The reaction mixture was heated at 150° C. for 6 hours. After cooling to room temperature, the precipitate was collected by filtration, washed several times with MeOH, and dried overnight. The crude solid (1.03 g) was recrystallized from DMF to give N,N'-bis(4-n-hexylphenyl)-1,7-dicyanopyrelene-3,4:9,10-bis(dicarboxiamide) as a red powder (0.35 g, 0.46 mmol, 28.8% yield).

M.p.>250° C. (DMF); $^1$H NMR (CHCl$_3$, 400 MHz): δ 9.76 (d, 2H, J=8.0 Hz), 9.04 (s, 2H), 9.00 (d, 2H, J=8.4 Hz), 7.42 (d, 4H, J=8.0 Hz), 7.26 (d, 4H, J=8.0 Hz), 2.73 (t, 4H, J=8.0 Hz), 1.73-1.68 (m, 4H), 1.44-1.40 (m, 4H), 1.39-1.32 (m, 4H), 1.30-1.19 (m, 4H), 0.93 (t, 6H, J=7.6 Hz); Elemental Analysis (calculated for: C$_{50}$H$_{40}$N$_4$O$_4$: C, 78.93; H, 5.30; N, 7.36): C, 79.11; H, 5.81; N, 5.55.

Example 3

Preparation of N,N'-bis(4-n-dodecylphenyl)-1,7-dicyanoperylene-3,4:9,10-bis(dicarboxiamide) (PDIPh12-CN$_2$)

Part A: Preparation of N,N'-bis(4-n-dodecylphenyl)-1,7-dibromoperylene-3,4:9,10-bis(dicarboxiamide) (PDIPh12-Br$_2$)

4-Dodecylaniline (5.00 g, 19.12 mmol) was added to a suspension of 1,7-dibromoperylene-3,4:9,10-dianhydride (2.63 g, 4.78 mmol) in propionic acid (52.5 mL). The reaction mixture was heated under reflux for 12 hours. After cooling to room temperature, the resulting solid was collected by filtration, washed with propionic acid and several times with MeOH, and finally dried overnight. The crude product (3.25 g) was extracted using a Soxhlet extractor with chloroform (CHCl$_3$, 500 mL) over 2 days and the resulting solid was purified by chromatography on silica gel (CH$_2$Cl$_2$) to afford N,N'-bis(4-n-dodecylphenyl)-1,7-dibromoperylene-3,4:9,10-bis(dicarboxiamide) as a red solid (1.20 g, 1.11 mmol, 24.2% yield).

M.p. >300° C. (DMF); $^1$H NMR (CHCl$_3$, 500 MHz): δ 9.58 (d, 2H, J=7.9 Hz), 9.00 (s, 2H), 8.80 (d, 2H, J=7.9 Hz), 7.41 (d, 4H, J=7.7 Hz), 7.26 (d, 4H, J=7.7 Hz), 2.73 (t, 4H, J=6.7 Hz), 1.70 (m, 4H), 1.62-1.1 (m, 36H), 0.95 (t, 6H, J=6.5 Hz); Elemental Analysis (calculated C, 69.50; H, 6.22; N, 2.70): C, 69.57; H, 6.29; N, 2.76.

Part B: Preparation of N,N'-bis(4-n-dodecylphenyl)-1,7-dicyanoperylene-3,4:9,10-bis(dicarboxiamide) (PDIPh12-CN$_2$)

A mixture of N,N'-bis(4-n-dodecylphenyl)-1,7-dibromoperylene-3,4:9,10-bis(dicarboxiamide) (1.00 g, 0.964 mmol) and CuCN (1.57 g, 17.5 mmol) in DMF (37 mL) was deaerated and placed under nitrogen. The reaction mixture was heated at 150° C. for 6 hours. After cooling to room temperature, the precipitate was collected by filtration, washed several times with MeOH, and dried overnight. The crude solid (0.85 g) was purified by chromatography on silica gel (CH$_2$Cl$_2$:acetone—98:2) to give N,N'-bis(4-n-dodecylphenyl)-1,7-dicyanoperylene-3,4:9,10-bis(dicarboxiamide) as a red powder (0.40 g, 0.43 mmol, 44.5% yield).

M.p. >300° C. (DMF); $^1$H NMR (CHCl$_3$, 500 MHz): δ 9.78 (d, 2H, J=7.9 Hz), 9.05 (s, 2H), 9.01 (d, 2H, J=7.9 Hz), 7.44 (d, 4H, J=6.9 Hz), 7.26 (d, 4H, J=6.9 Hz), 2.73 (t, 4H, J=6.7 Hz), 1.70 (m, 4H), 1.62-1.1 (m, 36H), 0.95 (t, 6H, J=6.5 Hz); Elemental Analysis (calculated C, 80.14; H, 6.94; N, 6.03): C, 79.79; H, 6.98; N, 6.12.

FIG. 1 provides the UV-vis absorption spectra in chloroform of N,N'-bis(4-n-dodecylphenyl)-1,7-dicyanoperylene-3,4:9,10-bis(dicarboxiamide) (PDIPh12-CN$_2$).

Example 4

Preparation of N,N'-bis{4-[(3S)-3,7-dimethyl-6-octenyl]phenyl}-1,7-dicyanoperylene-3,4:9,10-bis(dicarboxiamide) (PDIPhCitr-CN$_2$)

Part A: Preparation of 4-[(3S)-3,7-dimethyl-6-octenyl]aniline

Citronellylmagnesium bromide [from S-citronellylbromide (14.46 g, 66 mmol) and magnesium (3.20 g, 132 mmol)] in THF (80 mL) was added to a suspension of 4-iodoaniline (4.38 g, 20 mmol) and [1,1'-bis(diphenylphosphino)ferrocene] dichloropalladium(II) (PdCl$_2$(dppf), 0.150 g, 0.2 mmol) in THF (25 mL) maintained at −78° C. under a nitrogen atmosphere. After stirring for 10 minutes at −78° C., the reaction mixture was heated under reflux for 16 hours and then quenched with 5% hydrochloric acid (HCl). The aqueous solution was then extracted with ether (3×30 mL) and the combined fractions were washed with water, dried over magnesium sulfate (MgSO$_4$), and the solvent was evaporated to give 4-[(3S)-3,7-dimethyl-6-octenyl]aniline as a dark oil (41.9 g) which was used in the next step without additional purification.

HRMS (calculated for C$_{16}$H$_{25}$N, 231.1987): 231.1976.

Part B: Preparation of N,N'-bis{4-[(3S)-3,7-dimethyl-6-octenyl]phenyl}-1,7-dibromoperylene-3,4:9,10-bis(dicarboxiamide) (PDIPhCitr-Br$_2$)

4-[(3S)-3,7-Dimethyl-6-octenyl]aniline (4.53 g, 19.62 mmol) was added in three portions to a suspension of 1,7-dibromoperylene-3,4:9,10-dianhydride (3.00 g, 5.45 mmol) in propionic acid (60 mL). The reaction mixture was heated under reflux for 12 hours. After cooling to room temperature, the resulting solid was collected by filtration, washed with propionic acid and several times with MeOH, and finally dried overnight. The crude product (6.68 g) was purified by chromatography on silica gel (CH$_2$Cl$_2$) to give N,N'-bis{4-[(3S)-3,7-dimethyl-6-octenyl]phenyl}-1,7-dibromoperylene-3,4:9,10-bis(dicarboxiamide) as a red solid (1.41 g, 1.44 mmol, 26.4% yield).

M.p. >250° C. (DMF); $^1$H NMR (CDCl$_3$, 500 MHz): δ 9.52 (d, 2H, J=7.8 Hz), 8.96 (s, 2H), 8.74 (d, 2H, J=7.8 Hz), 7.41 (d, 4H, J=8.0 Hz), 7.21 (d, 4H, J=8.0 Hz), 5.18 (t, 2H, J=7.1 Hz), 2.72 (t, 4H, J=7.8 Hz), 2.15-1.96 (m, 4H), 1.80-1.40 (m, 6H), 1.66 (s, 6H), 1.64 (s, 6H), 1.40-1.20 (m, 4H), 1.04 (d, 6H, J=6.5 Hz); Elemental Analysis (calculated for C$_{56}$H$_{52}$Br$_2$N$_2$O$_4$: C, 68.86; H, 5.37; N, 2.87): C, 68.94; H, 5.22; N, 2.77.

Part C: Preparation of N,N'-bis{4-[(3S)-3,7-dimethyl-6-octenyl]phenyl}-1,7-dicyanoperylene-3,4:9,10-bis(dicarboxiamide) (PDIPhCitr-CN$_2$)

A mixture of N,N'-bis{4-[(3S)-3,7-dimethyl-6-octenyl]phenyl}-1,7-dibromoperylene-3,4:9,10-bis(dicarboxiamide) (1.00 g, 1.14 mmol) and CuCN (1.97 g, 22 mmol) in DMF (50 mL) was deaerated and placed under nitrogen. The reaction mixture was heated at 150° C. for 7 hours. After cooling to room temperature, the precipitate was collected by filtration, washed several times with MeOH, and dried overnight. The crude solid (0.67 g) was recrystallized from DMF-xylene to afford N,N'-bis{4-[(3S)-3,7-dimethyl-6-octenyl]phenyl}-1,7-dicyanoperylene-3,4:9,10-bis(dicarboxiamide) as a red powder (0.53 g, 0.61 mmol, 53.5% yield).

M.p. >250° C. (DMF); $^1$H NMR (CDCl$_3$, 500 MHz): δ 9.74 (d, 2H, J=7.7 Hz), 9.06 (s, 2H), 9.00 (d, 2H, J=7.7 Hz), 7.43 (d, 4H, J=7.8 Hz), 7.30 (d, 4H, J=7.8 Hz), 5.16 (t, 2H, J=7.2 Hz), 2.73 (t, 4H, J=7.8 Hz), 2.16-1.96 (m, 4H), 1.80-1.40 (m, 6H), 1.66 (s, 6H), 1.63 (s, 6H), 1.40-1.20 (m, 4H), 1.05 (d, 6H, J=6.6 Hz); Elemental Analysis (calculated for C$_{58}$H$_{52}$N$_4$O$_4$: C, 80.16; H, 6.03; N, 6.45): C, 80.53; H, 5.99; N, 6.43.

Example 5

Preparation of N,N'-bis(4-heptyloxyphenyl)-1,7-dicyanoperylene-3,4:9,10-bis(dicarboxiamide) (PDIPhO7-CN$_2$)

Part A: Preparation of N,N'-bis(4-heptyloxyphenyl)-1,7-dibromoperylene-3,4:9,10-bis(dicarboxiamide) (PDIPhO7-Br$_2$)

4-Heptyloxyaniline (4.08 g, 19.62 mmol) was added in three portions to a suspension of 1,7-dibromoperylene-3,4:9,10-dianhydride (3.00 g, 5.45 mmol) in propionic acid (56 mL). The reaction mixture was heated under reflux for 12 hours. After cooling to room temperature, the resulting solid was collected by filtration, washed with propionic acid and several times with MeOH, and finally dried overnight. The crude product (3.45 g) was purified by chromatography on silica gel ($CH_2Cl_2$) to give N,N'-bis(4-heptyloxyphenyl)-1,7-dibromoperylene-3,4:9,10-bis(dicarboxiamide) as a red solid (0.28 g, 0.31 mmol, 5.7% yield).

M.p. >250° C. (DMF): $^1$H NMR ($CHCl_3$, 400 MHz): δ 9.54 (d, 2H, J=7.6 Hz), 8.96 (s, 2H), 8.76 (d, 2H, J=7.6 Hz), 7.24 (d, 4H, J=8.8 Hz), 7.09 (d, 4H, J=8.4 Hz), 4.04 (t, 4H, J=6.4 Hz), 1.88-1.62 (m, 4H), 1.55-1.45 (m, 4H), 1.45-1.30 (m, 12H), 0.93 (t, 6H, J=6.8 Hz); Elemental Analysis (calculated for $C_{50}H_{44}Br_2N_2O_6$; C, 64.66; H, 4.78; N, 3.02): C, 64.18; H, 4.29; N, 3.88.

Part B: Preparation of N,N'-bis(4-heptyloxyphenyl)-1,7-dicyanoperylene-3,4:9,10-bis(dicarboxiamide) (PDIPhO7-$CN_2$)

A mixture of N,N'-bis(4-heptyloxyphenyl)-1,7-dibromoperylene-3,4:9,10-bis(dicarboxiamide) (0.25 g, 0.27 mmol) and CuCN (0.44 g, 4.90 mmol) in DMF (11 mL) was deaerated and placed under nitrogen. The reaction mixture was heated at 150° C. for 6 hours. After cooling to room temperature, the precipitate was collected by filtration, washed several times with MeOH, and dried overnight. The crude solid (0.22 g) was crystallized from trichlorobenzene (TCB, 0.11 g, 0.13 mmol, 59.1% yield).

M.p. >250° C. (DMF); $^1$H NMR ($C_2D_2Cl_4$, 500 MHz): δ 9.82 (d, 2H, J=8.0 Hz), 9.11 (s, 2H), 9.07 (d, 2H, J=8.0 Hz), 7.38 (d, 4H, J=8.7 Hz), 7.23 (d, 4H, J=8.7 Hz), 4.18 (t, 4H, J=6.5 Hz), 1.86-1.60 (m, 4H), 1.55-1.44 (m, 4H), 1.45-1.32 (m, 12H), 1.02 (t, 6H, J=6.8 Hz); HRMS (calculated for $C_{52}H_{44}O_4N_4$: 820.3255): 820.3234.

Example 6

Preparation of N,N'-bis(4-biphenylyl)-1,7-dicyanoperylene-3,4:9,10-bis(dicarboxiamide) (PDIPhPh-$CN_2$)

Part A: Preparation of N,N'-bis(4-biphenylyl)-1,7-dibromoperylene-3,4:9,10-bis(dicarboxiamide) (PDIPhPh-$Br_2$)

4-Aminobiphenyl (3.69 g, 21.81 mmol) was added to a suspension of 1,7-dibromoperylene-3,4:9,10-dianhydride (4.00 g, 7.27 mmol) in propionic acid (40 mL). The reaction mixture was heated under reflux for 12 hours. After cooling to room temperature, the resulting solid was collected by filtration, washed with propionic acid and several times with MeOH, and finally dried overnight. The crude product (3.00 g) was used in the next step without additional purification.

HRMS (calculated for $C_{48}H_{24}O_4N_2Br_2$: 850.0097): 850.0072.

Part B: Preparation of N,N'-bis(4-biphenylyl)-1,7-dicyanoperylene-3,4:9,10-bis(dicarboxiamide) (PDIPhPh-$CN_2$)

A mixture of crude N,N'-bis(4-biphenylyl)-1,7-dibromoperylene-3,4:9,10-bis(dicarboxiamide) (3.00 g, 3.52 mmol) and CuCN (5.91 g, 66.0 mmol) in DMF (140 mL) was deaerated and placed under nitrogen. The reaction mixture was heated at 150° C. for 6 hours. After cooling to room temperature, the precipitate was collected by filtration, washed several times with MeOH, and dried overnight. The crude solid (1.73 g) was crystallized several times from TCB-DMF.

M.p. >300° C. (DMF); HRMS (calculated for: $C_{50}H_{24}N_4O_4$: 744.1792): 744.1782.

Example 7

Preparation of N,N'-bis[4-(4'-n-octylbiphenylyl)]-1,7-dicyanoperylene-3,4:9,10-bis(dicarboxiamide) (PDIPhPh8-$CN_2$)

Part A: Preparation of p-n-octylphenylboronic acid n-Butyllithium (BuLi, 1.6 M in hexanes, 2.4 mL, 3.8 mmol) was added dropwise to a stirred solution of p-n-octyl-iodobenzene (1.0 g, 3.2 mmol) in dry THF (15 mL) at −78° C. under nitrogen. After stirring for 30 minutes and maintaining the temperature at −78° C., trimethylborate (0.4 g, 3.8 mmol) was added dropwise. The system was allowed to return to room temperature after 1 hour and was left stirring under nitrogen overnight. Concentrated HCl (8 mL) and water (15 mL) were then added and stirring was continued for 2 hours. The mixture was extracted with ether (15 3 mL). The ethereal phase was combined and was washed with brine and water (20 2 mL), dried with $MgSO_4$, and the solvent removed in vacuo to give p-n-octylphenylboronic acid as a white solid (0.63 g, 84% yield).

$^1$H NMR ($CDCl_3$) δ, 0.89 (3H, t), 1.21-1.43 (10H, m), 1.66 (2H, quint), 2.70 (2H, t), 7.32 (2H, d, J=7.5 Hz), 8.16 (2H, d, J=7.5 Hz); GC MS m/z=234 ($M^+$).

Part B: Preparation of 4'-nitro-4-n-octyl-biphenyl

Tetrakis(triphenylphosphine)palladium (0) (0.30 g, 0.26 mmol) and p-n-octylphenylboronic acid (1.0 g, 4.3 mmol) were sequentially added to a stirred solution of 4-nitroiodobenzene (0.87 g, 3.5 mmol) in 1,2-dimethoxyethane (13 mL) and aqueous sodium carbonate (2 M, 13 mL) under dry nitrogen. The stirred mixture was heated under reflux overnight and cooled. Water was added and the product was extracted into ether (30 3 mL) and the combined ethereal extracts were washed with brine and dried with $MgSO_4$. The solvent was removed in vacuo and the residue was purified by chromatography using a short silica gel column (hexane:ethyl acetate—5:1 to 2:1] to provide 4'-nitro-4-n-octyl-biphenyl as a yellow oil, which solidified upon standing (1.04 g, 95% yield). The solid was used without further purification.

$^1$H NMR ($CDCl_3$) δ 0.90 (3H, t), 1.19-1.58 (10H, m), 1.67 (2H, quint), 2.68 (2H, t), 7.31 (2H, d, J=8.5 Hz), 7.56 (2H, d, J=8.5 Hz), 7.73 (2H, d, J=9.0 Hz), 8.29 (2H, d, J=9.0 Hz); GC MS m/z=311 ($M^+$).

Part C: Preparation of 4'-amino-4-n-octyl-biphenyl

4'-Nitro-4-n-octyl-biphenyl (1.2 g, 3.9 mmol) was added to a suspension of palladium on carbon (Pd/C, 1.0 g) in a mixed solvent of THF (60 mL) and ethanol (24 mL). The preparation was hydrogenized under constant hydrogen flow for 3 hours. The catalyst was filtered out, and the volatiles were removed in vacuo to give a pale yellow oil. Chromatography on silica gel gave 4-n-octyl-4'-amino-biphenyl as a colorless oil, which solidified upon standing (0.75 g, 67% yield).

$^1$H NMR ($CDCl_3$) δ 0.89 (3H, t), 1.10-1.56 (10H, m), 1.63 (2H, m), 2.61 (2H, t), 3.71 (1H, b), 6.75 (2H, d, J=10.0 Hz), 7.21 (2H, d, J=10.0 Hz), 7.41 (2H, d, J=9.0 Hz), 7.45 (2H, d, J=9.0 Hz); GC MS m/z=281 ($M^+$).

Part D: Preparation of N,N'-bis[4-(4'-n-octylbiphenylyl)]-1,7-dibromoperylene-3,4:9,10-bis(dicarboxiamide) (PDIPhPh8-Br₂)

A mixture of 4-amino-4'-n-octylbiphenyl (5.00 g, 17.77 mmol) and 1,7-dibromoperylene-3,4:9,10-dianhydride (3.26 g, 9.92 mmol) in propionic acid (100 mL) was heated under reflux for 26 hours. After cooling to room temperature, the resulting solid was collected by filtration, washed with propionic acid and several times with hexane and MeOH, and finally dried overnight. The crude product (5.3 g) was purified by chromatography on silica gel ($CH_2Cl_2$) to afford N,N'-bis[4-(4'-n-octylbiphenylyl)]-1,7-dibromoperylene-3,4:9,10-bis(dicarboxiamide) as a red solid (1.10 g, 1.11 mmol, 24.2% yield).

M.p. >300° C. (TCB-DMF); $^1$H NMR ($CHCl_3$, 500 MHz): δ 9.54 (d, 2H, J=8.0 Hz), 8.96 (s, 2H), 8.76 (d, 2H, J=8.0 Hz), 7.76 (d, 4H, J=7.3 Hz), 7.56 (d, 4H, J=7.3 Hz), 7.37 (d, 4H, J=7.3 Hz), 7.26 (d, 4H, J=7.3 Hz), 2.65 (t, 4H, J=6.7 Hz), 1.71 (m, 4H), 1.44-1.20 (m, 20H), 0.95 (t, 6H, J=6.5 Hz); Elemental Analysis (calculated C, 71.38; H, 5.24; N, 2.60): C, 71.52; H, 5.09; N, 2.68.

Part E: Preparation of N,N'-bis[4-(4'-n-octylbiphenylyl)]-1,7-dicyanoperylene-3,4:9,10-bis(dicarboxiamide) (PDIPhPh8-CN₂)

A mixture of N,N'-bis[4-(4'-n-octylbiphenylyl)]-1,7-dibromoperylene-3,4:9,10-bis(dicarboxiamide) (0.70 g, 0.65 mmol) and CuCN (1.06 g, 11.8 mmol) in DMF (30 mL) was deaerated and placed under nitrogen. The reaction mixture was heated at 150° C. for 6 hours. After cooling to room temperature, the precipitate was collected by filtration, washed several times with MeOH, and dried overnight. The crude solid (0.59 g) was purified by chromatography on silica gel ($CH_2Cl_2$:acetone—98:2) to give N,N'-bis[4-(4'-n-octylbiphenylyl)]-1,7-dicyanoperylene-3,4:9,10-bis(dicarboxiamide) as a red powder (0.25 g, 0.26 mmol, 40.0% yield).

M.p. >300° C. (TCB-DMF); $^1$H NMR ($CHCl_3$, 500 MHz): δ 9.80 (d, 2H, J=8.0 Hz), 9.08 (s, 2H), 9.05 (d, 2H, J=8.0 Hz), 7.80 (d, 4H, J=7.3 Hz), 7.60 (d, 4H, J=7.3 Hz), 7.44 (d, 4H, J=7.3 Hz), 7.33 (d, 4H, J=7.3 Hz), 2.72 (t, 4H, J=6.7 Hz), 1.72 (m, 4H), 1.50-1.20 (m, 36 H), 0.95 (t, 6H, J=6.5 Hz); Elemental Analysis (calculated C, 81.79; H, 5.82; N, 5.78): C, 81.15; H, 5.61; N, 5.48.

Figure 2:
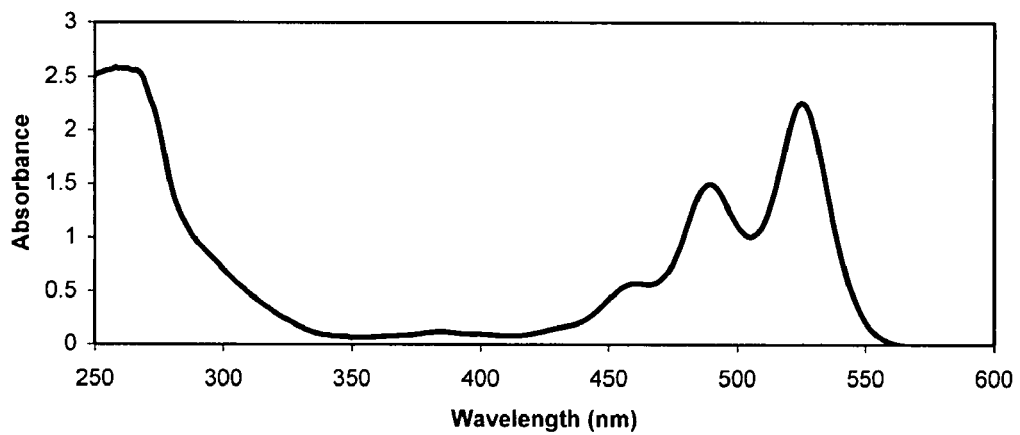
FIG. 2 is a UV-vis absorption spectrum of a compound of the present teachings (PDIPhPh8-$CN_2$) in chloroform.

FIG. 2 provides the UV-vis absorption spectra in chloroform of N,N'-bis[4-(4'-n-octylbiphenylyl)]-1,7-dicyanoperylene-3,4:9,10-bis(dicarboxiamide) (PDIPhPh8-CN₂).

Example 8

Preparation of N,N'-bis{4-[4'-((3S)-3,7-dimethyl-6-octenyl]biphenylyl}-1,7-dicyanoperylene-3,4:9,10-bis(dicarboxiamide) (PDIPhPhCitr-CN₂)

Part A: Preparation of 1-iodo-4-[(3S)-3,7-dimethyl-6-octenyl]benzene

A suspension of 4-[(3S)-3,7-dimethyl-6-octenyl]aniline (10.0 g, 43.2 mmol, Example 4) in concentrated HCl (9 mL) and water (100 mL) was cooled to 0° C. and then a solution of sodium nitrate ($NaNO_2$, 2.96 g, 43.2 mmol) in water (22 mL) was added dropwise. To the resulting arenediazonium salt a solution of potassium iodide (7.11 g, 43.2 mmol) in water (22 mL) was added dropwise and the mixture was heated at 40° C. for 2 hours. Sodium thiosulfate was added and the suspension was extracted with ether (3×50 mL) and the combined organic phase was washed with brine, dried over anhydrous sodium sulfate, and concentrated in vacuo to give a dark oil. The crude material was dissolved in ether and filtered through a plug of silica gel to give 1-iodo-4-[(3S)-3,7-dimethyl-6-octenyl]benzene as a colorless oil (9.27 g, 27.1 mmol, 62.5% yield).

$^1$H NMR ($CDCl_3$): δ 7.59 (2H, d, J=8.0), 6.94 (2H, d, J=8.0), 5.39 (t, 2H, J=7.2 Hz), 2.58 (t, 4H, J=7.9 Hz), 2.05-1.40 (m, 10H), 1.65 (s, 6H), 1.63 (s, 6H), 1.40-1.20 (m, 4H), 1.05 (d, 6H, J=6.6 Hz); MS m/z=342.1 (M⁺).

Part B: Preparation of 4-[(3S)-3,7-dimethyl-6-octenyl]phenylboronic acid n-BuLi (19.5 mL, 31.23 mmol, 1.6 M in hexanes) was added over 10 minutes to a solution of 1-iodo-4-octylbenzene (9.00 g, 26.3 mmol) in dry THF (120 mL) maintained at −78° C. After stirring for 30 minutes at −78° C. trimethylborate (3.29 g, 31.23 mmol) was added dropwise and the mixture left to reach room temperature overnight. The reaction mixture was poured into an HCl solution (65 mL of concentrated HCl in 120 mL of water) and the resulting suspension stirred for 2 hours. The product was extracted with diethyl ether (3×60 mL) and the combined organic phases were washed with brine, dried over $MgSO_4$, and filtered, and the solvent was evaporated in vacuo to afford 5.07 g of a crude product (19.5 mmol, 74.1% yield), which was used in the next step without further purification.

$^1$H NMR ($CDCl_3$): δ ppm 0.89 (3H, t), 1.28-1.31 (10H, m), 1.36 (12H, s), 1.62 (2H, m), 2.63 (2H, t), 7.20 (2H, d, J=7.5), 7.74 (2H, d, J=7.5).

Part C: Preparation of 4-[(3S)-3,7-dimethyl-6-octenyl]-4'-nitrobiphenyl

A mixture of boronic acid (5.00 g, 19.2 mmol), 4-nitroiodobenzene (3.88 g, 15.6 mmol), and tetrakis(triphenylphosphine)palladium(0) (1.34 g, 1.16 mmol) in 1,2-dimethoxyethane (60 mL) and an aqueous solution of sodium bicarbonate (2 M, 60 mL) was heated under reflux overnight under nitrogen. After cooling, water was added and the product was extracted with ether (60 3 mL) and the combined ethereal extracts were washed with brine and dried over $MgSO_4$. The solvent was removed in vacuo and the residue was purified by chromatography on silica gel (hexane-ethyl acetate) to give 4-[(3S)-3,7-dimethyl-6-octenyl]-4'-nitrobiphenyl as a yellow oil (4.55 g, 13.49 mmol, 86.5% yield).

$^1$H NMR ($CDCl_3$) δ 8.29 (2H, d, J=9.0 Hz), 7.73 (2H, d, J=9.0 Hz), 7.56 (2H, d, J=8.5 Hz), 7.31 (2H, d, J=8.5 Hz), 5.29 (t, 2H, J=7.3 Hz), 2.56 (t, 4H, J=7.8 Hz), 2.04-1.38 (m, 10H), 1.65 (s, 6H), 1.62 (s, 6H), 1.40-1.20 (m, 4H), 1.05 (d, 6H, J=6.6 Hz); HRMS (calculated for $C_{22}H_{27}NO_2$: 337.2042):: 337.2048.

Part D: Preparation of 4-[(3S)-3,7-dimethyl-6-octenyl]-4'-aminobiphenyl

A mixture of 4-[(3S)-3,7-dimethyl-6-octenyl]phenylboronic acid (5.00 g, 19.2 mmol), 4-iodoaniline (2.79 g, 12.75 mmol), and a quaternary ammonium salt (Aliquat 336, 1.3 g) was degased three times with nitrogen before 100 mL of dry toluene was added. This step was followed by addition of tetrakis(triphenylphosphine)palladium (1.46 g) and aqueous sodium carbonate (1 M, 60 mL, deaerated for 2 hours) under nitrogen. The mixture was stirred vigorously and heated under reflux for 20 hours. The organic phase of the resulting reaction mixture was filtered through a thin layer of Celite® and evaporated to dryness to give 3.09 g of crude material. The crude material was purified by chromatography on silica gel (ethyl acetate:hexanes) to yield 4-[(3S)-3,7-dimethyl-6-octenyl]-4'-aminobiphenyl as a yellow oil (2.64 g, 8.59 mmol, 67.4% yield).

HRMS (calculated for $C_{22}H_{29}N$, 307.2300): 307.2312.

Part E: Preparation of N,N'-bis{4-[4'-((3S)-3,7-dimethyl-6-octenyl]biphenylyl}-1,7-dibromoperylene-3,4:9,10-bis(dicarboxiamide) (PDIPhPhCitr-Br$_2$)

4-[(3S)-3,7-Dimethyl-6-octenyl]-4'-aminobiphenyl (1.68 g, 5.45 mmol) was added in three portions to a suspension of 1,7-dibromoperylene-3,4:9,10-dianhydride (1.00 g, 1.82 mmol) in propionic acid (20 mL). The reaction mixture was heated under reflux for 12 hours. After cooling to room temperature, the resulting solid was collected by filtration, washed with propionic acid and several times with MeOH, and dried overnight. The crude product (2.2 g) was purified by chromatography on silica gel ($CH_2Cl_2$) to give N,N'-bis{4-[4'-((3S)-3,7-dimethyl-6-octenyl]biphenylyl}-1,7-dibromoperylene-3,4:9,10-bis(dicarboxiamide) as a red solid (0.373 g, 0.33 mmol, 18.2% yield).

M.p. >250° C. (DMF); $^1$H NMR (CDCl$_3$, 500 MHz): δ 9.53 (d, 2H, J=8.1 Hz), 8.96 (s, 2H), 8.76 (d, 2H, J=8.1 Hz), 7.76 (d, 4H, J=7.2 Hz), 7.56 (d, 4H, J=7.2 Hz), 7.37 (d, 4H, J=7.2 Hz), 7.26 (d, 4H, J=7.2 Hz), 5.17 (t, 2H, J=7.1 Hz), 2.72 (t, 4H, J=7.8 Hz), 2.15-1.96 (m, 4H), 1.80-1.40 (m, 6H), 1.66 (s, 6H), 1.64 (s, 6H), 1.40-1.21 (m, 4H), 1.05 (d, 6H, J=6.5 Hz); Elemental Analysis (calculated for $C_{68}H_{60}Br_2N_2O_4$: C, 72.34; H, 5.36; N, 2.48): C, 71.67; H, 5.03; N, 2.19.

Part F: Preparation of N,N'-bis{4-[4'-((3S)-3,7-dimethyl-6-octenyl]biphenylyl}-1,7-dicyanoperylene-3,4:9,10-bis(dicarboxiamide) (PDIPhPhCitr-CN$_2$)

A mixture of N,N'-bis{4-[4'-((3S)-3,7-dimethyl-6-octenyl]biphenylyl}-1,7-dibromoperylene-3,4:9,10-bis(dicarboxiamide) (0.35 g, 0.27 mmol) and CuCN (0.47 g, 5.13 mmol) in DMF (13 mL) was deaerated and placed under nitrogen. The reaction mixture was heated at 150° C. for 6 hours. After cooling to room temperature, the precipitate was collected by filtration, washed several times with MeOH, and dried overnight. The crude solid (0.67 g) was recrystallized from DMF-xylene to give N,N'-bis{4-[4'-((3S)-3,7-dimethyl-6-octenyl]biphenylyl}-1,7-dicyanoperylene-3,4:9,10-bis(dicarboxiamide) as a red powder (0.22 g, 0.22 mmol, 81.5% yield).

M.p. >250° C. (DMF-dichlorobenzene); $^1$H NMR (CDCl$_3$, 500 MHz): δ 9.74 (d, 2H, J=7.7 Hz), 9.06 (s, 2H), 9.00 (d, 2H, J=7.7 Hz), 7.43 (d, 4H, J=7.8 Hz), 7.30 (d, 4H, J=7.8 Hz), 5.16 (t, 2H, J=7.2 Hz), 2.73 (t, 4H, J=7.8 Hz), 2.16-1.96 (m, 4H), 1.80-1.40 (m, 6H), 1.66 (s, 6H), 1.63 (s, 6H), 1.40-1.20 (m, 4H), 1.05 (d, 6H, J=6.6 Hz); Elemental Analysis (calculated for $C_{70}H_{60}N_4O_4$: C, 82.33; H, 5.92; N, 5.49): C, 81.77; H, 5.69; N, 5.82.

Example 9

Preparation of N,N'-bis[4-(2',3',4',5',6'-pentafluorobiphenyl)]-1,7-dibromoperylene-3,4:9,10-bis(dicarboxiamide) (PDIPhPh$^F$-CN$_2$)

Part A: Preparation of 4-nitro-2',3',4',5',6'-pentafluorobiphenyl

A mixture of 4-iodonitrobenzene (15 g, 0.060 mol), bromopentafluorobenzene (14.9 g, 2.56 mL, 0.060 mol) and copper powder (30 g) was placed into a 50-mL J-Young glass tube and heated at 190° C. for 24 hours. The tube was cooled and the mixture was extracted exhaustively with dichloromethane. The solvent was removed and the residue was extracted with boiling hexane and filtered while hot. The solvent was removed and the resulting viscous solid was sublimed to obtain 4-nitro-2',3',4',5',6'-pentafluorobiphenyl as a yellow solid (11.0 g, 63% yield).

$^1$H NMR (400 MHz, CDCl$_3$): δ 8.38, (d, 2H), 7.65 (d, 2H). $^{19}$F NMR (376 MHz, CDCl$_3$): δ 142.9, (d, 2F), 152.8 (t, 1F), 161.1 (t, 2F).

Part B: Preparation of 4-amino-2',3',4',5',6'-pentafluorobiphenyl

4-Nitro-2',3',4',5',6'-pentafluorobiphenyl (10 g, 0.0345 mol) was dissolved in absolute ethanol (750 mL) and stirred under a hydrogen atmosphere (1 atm.) over Pd/C (0.3 g) until absorption of hydrogen ceased. The solution was filtered and the solvent was removed. The crude product was purified by column chromatography to give 4-amino-2',3',4',5',6'-pentafluorobiphenyl as a white powder (8.0 g, 89% yield).

$^1$H NMR (400 MHz, CDCl$_3$): δ 7.23, (d, 2H), 6.78 (d, 2H), 3.85 (d, 2H). $^{19}$F NMR (376 MHz, CDCl$_3$): δ 142.9, (d, 2F), 152.8 (t, 1F), 161.1 (t, 2F); Elemental Analysis ($C_{12}H_6F_5N$): C, 55.61%; H, 2.33%; F, 36.65%; N, 5.40%.

Part C: Preparation of N,N'-bis[4-(2',3',4',5',6'-pentafluorobiphenyl)]-1,7-dibromoperylene-3,4:9,10-bis(dicarboxiamide) (PDIPhPh$^F$—Br$_2$)

A mixture of 4-amino-2',3',4',5',6'-pentafluorobiphenyl (1.40 g, 5.40 mmol) and 1,7-dibromoperylene-3,4:9,10-dianhydride (1.00 g, 1.80 mmol) in propionic acid (25 mL) was heated under reflux for 50 hours. After cooling to room temperature, the resulting solid was collected by filtration, washed with propionic acid and several times with hexane and MeOH, and dried overnight. The crude product (1.62 g) was used in the next step without additional purification.

M.p. >300° C.; HRMS (calculated for $C_{48}H_{14}Br_2F_{10}N_2O_4$: 1029.9161): 1029.9158.

Part D: Preparation of N,N'-bis[4-(2',3',4',5',6'-pentafluorobiphenyl)]-1,7-dibromoperylene-3,4:9,10-bis(dicarboxiamide) (PDIPhPh$^F$-CN$_2$)

A mixture of N,N'-bis[4-(2',3',4',5',6'-pentafluorobiphenyl)]-1,7-dibromoperylene-3,4:9,10-bis(dicarboxiamide) (0.21 g, 0.203 mmol) and CuCN (0.33 g, 3.69 mmol) in DMF (10 mL) was deaerated and placed under nitrogen. The reaction mixture was heated at 150° C. for 9 hours. After cooling to room temperature, the precipitate was collected by filtration, washed several times with MeOH, and dried overnight. The product (0.11 g, 0.12 mmol, 59.1% yield) was insoluble in common organic solvents and it was gradient-sublimed.

M.p. >300° C.; Elemental Analysis (calculated for $C_{50}H_{14}F_{10}N_4O_4$: C, 64.95; H, 1.53; N, 6.06): C, 65.06; H, 1.78; N, 6.41.

Example 10

Preparation of N,N'-bis[4-(4'-n-octyl-2',3',5',6'-tetrafluorobiphenyl)]-1,7-dicyanoperylene-3,4:9,10-bis(dicarboxiamide) (PDIPhPh$^F$8-CN$_2$)

Part A: Preparation of n-octyllithium

Lithium (2.86 g, 0.412 mol) ribbons were rinsed with hexane and then with diethyl ether and finally cut into small pieces (~5 mm in length) and placed into a 250-mL three-necked air-free flask equipped with an additional funnel under nitrogen atmosphere. Anhydrous diethyl ether (40 mL) was added using a syringe into the flask. Approximately 3 mL of a solution of n-C$_8$H$_{17}$Br (32.04 g, 0.166 mol) in anhydrous diethyl ether (37.5 mL) were added from a second funnel. The reaction mixture was stirred at room temperature until the lithium particles assumed a bright shiny appearance. The mixture was then cooled to approximately −10° C. using a dry ice-acetone bath. The remainder of the n-C$_8$H$_{17}$Br solution was added dropwise over a period of 1.5 hours while the temperature was maintained at −10° C. After stirring for 30 minutes at −10° C., the reaction mixture was allowed to warm up to 10° C. and stirred for an additional hour. The supernatant was removed by a cold cannula and used in the next step.

Part B: Preparation of 4-amino-4'-n-octyl-2',3',5',6'-tetrafluorobiphenyl n-Octyllithium in dry ether (9.5 mL) was added slowly to a solution of 4-amino-2',3',4',5',6'-pentafluorobiphenyl (1.5 g, 5.79 mmol, Example 9) in dry ether (100 mL) at −78° C. The solution was stirred at this temperature for 2 hours and then allowed to warm to room temperature over a period of 5 hours. Hydrochloric acid (3M, 100 mL) was added and a white solid was precipitated from the solution. The solid was filtered and dried. After sublimation, 4-amino-4'-n-octyl-2',3',5',6'-tetrafluorobiphenyl was obtained as a white solid (1.2 g, 63% yield).

$^1$H NMR (400 MHz, DMSO): δ 7.40, (d, 2H), 7.05 (d, 2H), 2.75 (t, 2H), 2.05 (t, 2H), 1.55 (t, 2H), 1.20-1.00 (m, 10H), 0.88 (t, 3H); $^{19}$F NMR (376 MHz, DMSO): δ-145.7; Elemental Analysis (C$_{20}$H$_{23}$F$_4$N): C, 67.97%; H, 6.56%; F, 21.50%; N, 3.96%.

Part C: Preparation of N,N'-bis[4-(4'-n-octyl-2',3',5',6'-tetrafluorobiphenyl)]-1,7-dibromoperylene-3,4:9,10-bis(dicarboxiamide) (PDIPhPh$^F$8-Br$_2$)

A mixture of 4-amino-4'-n-octyl-2',3',5',6'-tetrafluorobiphenyl (1.70 g, 4.00 mmol) and 1,7-dibromoperylene-3,4:9,10-dianhydride (0.50 g, 9.91 mmol) in propionic acid (40 mL) was heated under reflux for 48 hours. After cooling to room temperature, the resulting solid was collected by filtration, washed with propionic acid and several times with hexane and MeOH, and finally dried overnight. The crude product (0.73 g) was used in the next step without additional purification.

M.p. >300° C.; $^1$H NMR (CHCl$_3$, 300 MHz): δ 9.56 (d, 2H, J=8.1 Hz), 8.96 (s, 2H), 8.77 (d, 2H, J=8.1 Hz), 7.83 (d, 4H, J=7.6 Hz), 7.61 (d, 4H, J=7.6 Hz), 2.91 (t, 4H, broad), 1.71 (m, 4H), 1.60-1.25 (m, 20H), 0.99 (t, 6H, broad).

Part D: Preparation of N,N'-bis[4-(4'-n-octyl-2',3',5',6'-tetrafluorobiphenyl)]-1,7-dicyanoperylene-3,4:9,10-bis(dicarboxiamide) (PDIPhPh$^F$8-CN$_2$)

A mixture of N,N'-bis[4-(4'-n-octyl-2',3',5',6'-tetrafluorobiphenyl)]-1,7-dibromoperylene-3,4:9,10-bis(dicarboxiamide) (0.40 g, 0.325 mmol) and CuCN (0.53 g, 5.9 mmol) in DMF (15 mL) was deaerated and placed under nitrogen. The reaction mixture was heated at 150° C. for 6 hours. After cooling to room temperature, the precipitate was collected by filtration, washed several times with MeOH, and dried overnight. The crude solid (0.31 g) was crystallized from TCB to give N,N'-bis[4-(4'-n-octyl-2',3',5',6'-tetrafluorobiphenyl)]-1,7-dicyanoperylene-3,4:9,10-bis(dicarboxiamide) as a red powder (0.152 g, 0.136 mmol, 42.0% yield).

M.p. >300° C.; HRMS (calculated for C$_{66}$H$_{48}$F$_8$N$_4$O$_4$: 1112.3548): 1112.3543.

Example 11

Preparation of N,N'-bis[4-(4'-n-octyl-2,3,5,6-tetrafluorobiphenyl)]-1,7-dicyanoperylene-3,4:9,10-bis(dicarboxiamide) (PDIPhPh$^F$8-CN$_2$)

Part A: Preparation of 1-iodo-4-octylbenzene

To a suspension of 4-octylaniline (80.0 g, 389.6 mmol) in water (780 mL) was added aqueous HCl (40 mL) at room temperature. After the mixture was cooled to 0° C., more aqueous HCl (43 mL) was added, followed by dropwise addition of a solution of NaNO$_2$ (26.9 g, 389.6 mmol) in water (195 mL). To the resulting arenediazonium salt solution was added dropwise a solution of potassium iodide (64.67 g, 389.6 mmol) in water (195 mL). The resulting mixture was heated with stirring at 40° C. After two hours, sodium thiosulfate was added to decolorize and the product was extracted with ether. The ethereal extract was washed with brine, dried over anhydrous sodium sulfate, and concentrated in vacuo to give a crude oil. The crude material was dissolved in ether and filtered through a plug of silica gel three times and dried in vacuo to give 1-iodo-4-octylbenzene as a colorless oil. The product was used in the next step without further purification.

$^1$H NMR (CDCl$_3$): δ 0.90 (3H, t), 1.27-1.31 (10H, m), 1.59 (2H, m), 2.56 (2H, t), 6.94 (2H, d, J=8.0), 7.59 (2H, d, J=8.0) ppm.

Part B: Preparation of 4,4,5,5-tetramethyl-2-(4-octylphenyl)-1,3,2-dioxaborolane n-BuLi (16.6 mL, 1.6 M in hexanes) was added over 10 minutes to a solution of 1-iodo-4-octylbenzene from Part A (6.9 g, 21.8 mmol) in dry THF (100 mL) at −78° C. under a nitrogen atmosphere. The mixture was stirred for another 10 minutes at −78° C. 2-Isopropoxy-4,4,5,5-tetramethyl[1,3,2]dioxaborolane (6.21 mL, 30.4 mmol) was subsequently added dropwise to the mixture and stirring was continued at room temperature overnight. The reaction was then quenched with distilled water, and THF was removed under vacuum. The product was then extracted into diethyl ether and the organic layer was washed with brine, dried over MgSO$_4$, filtered and evaporated in vacuo to give 6.38 g of 4,4,5,5-tetramethyl-2-(4-octylphenyl)-1,3,2-dioxaborolane as a colorless oil. The product was used in the next step without further purification.

$^1$H NMR (CDCl$_3$): δ 0.89 (3H, t), 1.28-1.31 (10H, m), 1.36 (12H, s), 1.62 (2H, m), 2.63 (2H, t), 7.20 (2H, d, J=7.5), 7.74 (2H, d, J=7.5) ppm.

Part C: Preparation of 2,3,5,6-tetrafluoro-4'-octylbiphenyl-4-amine

A mixture of 4,4,5,5-tetramethyl-2-(4-octylphenyl)-1,3,2-dioxaborolane (415.0 mg, 1.31 mmol), 4-bromo-2,3,5,6-tetrafluorobenzenamine (213.0 mg, 0.87 mmol), and a quaternary ammonium salt (Aliquat 336, 0.090 g) was degassed three times with nitrogen before dry toluene (7.0 mL) was added. This step was followed by addition of tetrakis(triphenylphosphine) palladium (100.0 mg) and sodium carbonate (aq. 1 M, 4.0 mL), which had been deaerated for 2 hour, under nitrogen. The mixture was stirred vigorously, and heated at reflux for 20 hours. The organic phase of the resulting reaction mixture was filtered through a thin layer of Celite® and evaporated to dryness to give 0.6 g of a crude product. The crude material was purified by chromatography on silica gel (by using ethyl acetate:hexanes (1:9) as the eluent) to yield 2,3,5,6-tetrafluoro-4'-octylbiphenyl-4-amine as an off-white solid (0.280 g, 91% yield).

Elemental Analysis (calculated for $C_{20}H_{23}F_4N$: C, 67.97; H, 6.56; F, 21.50): C, 68.03; H, 6.47; F, 21.20; $^1H$ NMR (CDCl$_3$): δ 0.90 (3H, t), 1.28-1.37 (10H, m), 1.66 (2H, m), 2.67 (2H, t), 4.02 (2H, s), 7.27 (2H, d, J=7.5), 7.34 (2H, d, J=7.5) ppm; $^{19}F$ NMR (CDCl$_3$): −147.13 (m), δ −162.71 (m).

Part D: Preparation of N,N'-bis[4-(4'-n-octyl-2,3,5,6-tetrafluorobiphenyl)]-1,7-dicyanoperylene-3,4:9,10-bis(dicarboxiamide) (PDIPhPh$^F$8-CN$_2$)

N,N'-Bis[4-(4'-n-octyl-2,3,5,6-tetrafluorobiphenyl)]-1,7-dicyanoperylene-3,4:9,10-bis(dicarboxiamide) (PDIPh-Ph$^F$8-CN$_2$) can be prepared following procedures analogous to those described in Example 10, Parts C and D.

Example 12

Preparation of N,N'-bis(benzyl)-1,7-dicyanoperylene-3,4:9,10-bis(dicarboxiamide) (PDI1Ph-CN$_2$)

Part A: Preparation of N,N'-bis(benzyl)-1,7-dibromoperylene-3,4:9,10-bis(dicarboxiamide) (PDI1Ph-Br$_2$)

Benzylamine (2.10 g, 19.62 mmol) was added in three portions to a suspension of 1,7-dibromoperylene-3,4:9,10-dianhydride (3.00 g, 5.45 mmol) in propionic acid (60 mL). The reaction mixture was heated under reflux for 16 hours. After cooling to room temperature, the resulting solid was collected by filtration, washed with propionic acid and several times with MeOH, and dried overnight. The crude product (4.17 g) was purified by chromatography on silica gel (CH$_2$Cl$_2$) to give N,N'-bis(benzyl)-1,7-dibromoperylene-3,4:9,10-bis(dicarboxiamide) as a red solid (0.857 g, 1.18 mmol, 21.6% yield).

M.p. >250° C. (sublimation); $^1H$ NMR (CHCl$_3$, 400 MHz): δ 9.54 (d, 2H, J=7.9 Hz), 8.95 (s, 2H), 8.78 (d, 2H, J=7.9 Hz), 7.43-7.21 (m, 10H), 4.78 (s, 4H); Elemental Analysis (calculated for $C_{38}H_{20}Br_2N_2O_4C$, 62.66; H, 2.77; N, 3.85): C, 63.02; H, 2.78; N, 3.12.

Part B: Preparation of N,N'-bis(benzyl)-1,7-dicyanoperylene-3,4:9,10-bis(dicarboxiamide) (PDI1Ph-CN$_2$)

A mixture of N,N'-bis(benzyl)-1,7-dibromoperylene-3,4:9,10-bis(dicarboxiamide) (0.983 g, 0.85 mmol) and CuCN (2.2 g, 24.5.0 mmol) in DMF (50 mL) was deaerated and placed under nitrogen. The reaction mixture was heated at 150° C. for 7 hours. After cooling to room temperature, the precipitate was collected by filtration, washed several times with MeOH, and dried overnight. The crude solid was purified by multiple crystallizations from DMF-toluene to give N,N'-bis(benzyl)-1,7-dicyanoperylene-3,4:9,10-bis(dicarboxiamide) (PDI1Ph-CN$_2$) as a red solid (0.46 g, 0.733 mmol, 86.3% yield).

$^1H$ NMR (CHCl$_3$, 500 MHz): δ 9.78 (d, 2H, J=8.0 Hz), 9.04 (s, 2H), 9.02 (d, 2H, J=8.0 Hz), 7.45-7.23 (m, 10H), 4.78 (s, 4H); Elemental Analysis (calculated for $C_{40}H_{20}N_4O_4$; C, 77.41; H, 3.25; N, 9.03): C, 77.74; H, 3.48; N, 8.95.

Figure 3:
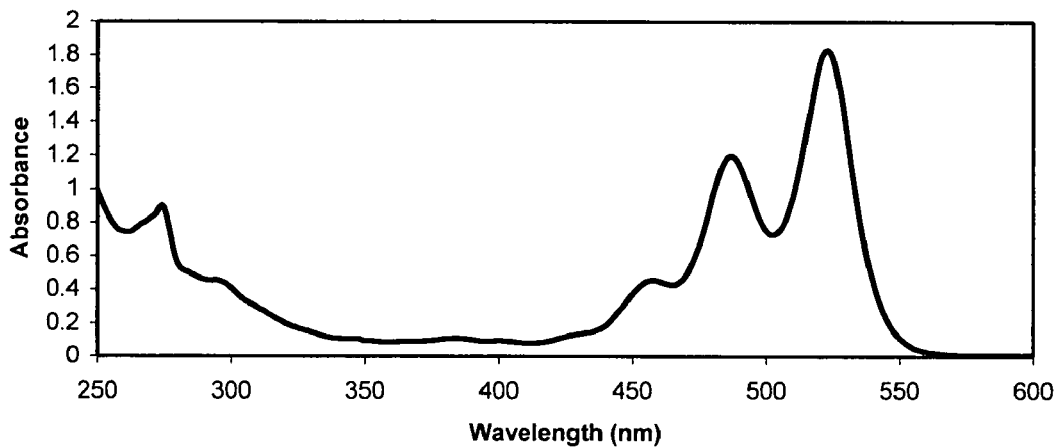
FIG. 3 is a UV-vis absorption spectrum of a compound of the present teachings (PDI1Ph-$CN_2$) in chloroform.

FIG. 3 provides the UV-vis absorption spectra in chloroform of N,N'-bis(benzyl)-1,7-dicyanoperylene-3,4:9,10-bis(dicarboxiamide) (PDI1Ph-CN$_2$).

Example 13

Preparation of N,N'-bis(4-n-butylbenzyl)-1,7-dicyanoperylene-3,4:9,10-bis(dicarboximide) (PDI1Ph4-CN$_2$)

Part A: Preparation of N,N'-bis(4-n-butylbenzyl)-1,7-dibromoperylene-3,4:9,10-bis(dicarboximide) (PDI1Ph4-Br$_2$)

To a 500 mL round-bottom flask was added dibromoperylene dianhydride (2.022 g, 3.66 mmol), propionic acid (100 mL) and 4-n-butylbenzylamine (2.50 mL, 14.8 mmol). The reaction mixture was heated under reflux under nitrogen for 4 hours and allowed to cool overnight. The precipitate was filtered, washed with MeOH (3×15 mL), and dried. The crude mixture was purified by chromatography with dichloromethane:acetone (98%:2%) and the second band was collected to yield N,N'-bis(4-n-butylbenzyl)-1,7-dibromoperylene-3,4:9,10-bis(dicarboximide) (1.313 g, 1.56 mmol, 43% yield).

$^1H$ NMR (CDCl$_3$) δ=9.373 (d, 2H, J=8.0 Hz), 8.843 (s, 2H), 8.617 (d, 2H, J=8.0 Hz), 7.401 (d, 4H, J=7.2 Hz), 7.059 (d, 4H, J=7.2 Hz), 5.292 (s, 4H), 2.486 (t, 4H, J=7.6 Hz), 1.496-1.183 (m, 8H), 0.815 (t, 6H, J=7.4 Hz). MALDI-MS (calculated: 840.6): 840.1.

Part B: Preparation of N,N'-bis(4-n-butylbenzyl)-1,7-dicyanoperylene-3,4:9,10-bis(dicarboximide) (PDI1Ph4-CN$_2$)

To a 100 mL round-bottom flask was added N,N'-bis(4-n-butylbenzyl)-1,7-dibromo-perylene-3,4:9,10-bis(dicarboximide) (0.557 g, 0.663 mmol), CuCN (1.14 g, 12.7 mmol), and DMF (75 mL). The reaction mixture was heated to 150° C. under nitrogen for 5 hours and then allowed to cool. The crude product was continuously extracted with CHCl$_3$ overnight, dried, and purified by chromatography on silica gel with CH$_2$Cl$_2$:acetone (98%:2%) to yield N,N'-bis(4-n-butylbenzyl)-1,7-dicyanoperylene-3,4:9,10-bis(dicarboximide) in quantitative yield (0.480 g, 0.655 mmol).

$^1H$ NMR (CDCl$_3$) δ=9.600 (d, 2H, J=8.0 Hz), 8.908 (s, 2H), 8.852 (d, 2H, J=8.0 Hz), 7.415 (d, 4H, J=8.0 Hz), 7.072 (d, 4H, J=8.0 Hz), 5.305 (s, 4H), 2.491 (t, 4H, J=7.4 Hz), 1.501-1.183 (m, 8H), 0.816 (t, 6H, J=7.4 Hz); MALDI-MS (calculated: 732.8): 732.4.

Example 14

Preparation of N,N'-bis(4-sec-butylphenyl)-1,7-dicyanoperylene-3,4:9,10-bis(dicarboxiamide) (PDIPhs4-CN$_2$)

Part A: Preparation of N,N'-bis(4-sec-butyl)phenyl)-1,7-dibromoperylene-3, 4:9,10-bis(dicarboxiamide) (PDIPhs4-Br$_2$)

4-sec-Butylaniline (4.75 g, 31.8 mmol) was added to a suspension of 1,7-dibromoperylene-3,4:9,10-dianhydride (4.37 g, 7.95 mmol) in propionic acid (50 mL). The reaction mixture was heated under reflux for 12 hours. After cooling to room temperature, the resulting solid was collected by filtration, washed with propionic acid and several times with MeOH, and dried overnight. The crude product (1.97 g) was purified by chromatography on silica gel (CH$_2$Cl$_2$) to give N,N'-bis(4-sec-butyl)phenyl)-1,7-dibromoperylene-3,4:9,10-bis(dicarboxiamide) as a red solid (0.20 g, 0.25 mmol, 3.1% yield).

M.p. >250° C. (DMF); $^1$H NMR (CHCl$_3$, 400 MHz): δ 9.56 (d, 2H, J=8.0 Hz), 8.98 (s, 2H), 8.78 (d, 2H, J=8.0 Hz), 7.40 (d, 4H, J=8.0 Hz), 7.26 (d, 4H, J=8.0 Hz), 2.74-2.70 (m, 2H), 1.76-1.60 (m, 4H), 1.33 (d, 6H, J=6.4 Hz), 0.92 (t, 6H, J=7.2 Hz); Elemental Analysis (calculated for: C$_{32}$H$_{24}$Br$_2$N$_2$O$_4$: C, 58.20; H, 3.66; N, 4.24): C, 58.05; H, 4.01; N, 3.89.

Part B: Preparation of N,N'-bis(4-sec-butylphenyl)-1,7-dicyanoperylene-3,4:9,10-bis(dicarboxiamide) (PDIPhs4-CN$_2$)

A mixture of N,N'-bis[4-(sec-butyl)phenyl]-1,7-dibromoperylene-3,4:9,10-bis(dicarboxiamide) (0.20 g, 0.25 mmol) and CuCN (0.41 g, 4.53 mmol) in DMF (10 mL) was deaerated and placed under nitrogen. The reaction mixture was heated at 150° C. for 6 hours. After cooling to room temperature, the precipitate was collected by filtration, washed several times with MeOH, and dried overnight. The crude solid was purified by chromatography on silica gel (CH$_2$Cl$_2$:acetone—98:2) to give N,N'-bis(4-sec-butylphenyl)-1,7-dicyanoperylene-3,4:9,10-bis(dicarboxiamide) as a red powder (0.12 g, 0.17 mmol, 68.0% yield).

M.p. >250° C. (DMF); $^1$H NMR (CHCl$_3$, 400 MHz): δ 9.76 (d, 2H, J=7.6 Hz), 9.03 (s, 2H), 9.00 (d, 2H, J=8.0 Hz), 7.42 (d, 4H, J=6.8 Hz), 7.26 (d, 4H, J=6.8 Hz), 2.78-2.70 (m, 2H), 1.75-1.60 (m, 4H), 1.33 (d, 6H, J=7.6 Hz), 0.93 (t, 6H, J=7.5 Hz); Elemental Analysis (calculated C, 78.06; H, 4.56; N, 7.29): C, 77.90; H, 4.74; N, 7.60.

Example 15

Preparation of N,N'-bis{4-[(3S)-3,7-dimethyl-6-octenyloxy]benzyl}-1,7-dicyanoperylene-3,4:9,10-bis(dicarboxiamide) (PDI1PhOCitr-CN$_2$)

Part A: Preparation of 4-[(3S)-3,7-dimethyl-6-octenyloxy]cyanobenzene

A mixture of 4-cyanophenol (6.0 g, 50.0 mmol), potassium carbonate (27.6 g, 200 mmol) and citronellylbromide (13.15 g, 60.0 mmol) in acetone (200 mL) was heated under reflux for 24 hours. The solvent was evaporated and the residue was taken up with CH$_2$Cl$_2$ (60 mL×2) and the solution filtered. The solvent was evaporated and the resulting oil was purified by flash column chromatography over silica gel (EtOAc/hexanes 1:1) as eluant to give 4-[(3S)-3,7-dimethyl-6-octenyloxy]cyanobenzene (11.76 g, 45.7 mmol, 91.4% yield) as a white oil.

$^1$H NMR (CDCl$_3$) δ 7.48 (d, 2H, J=8.2 Hz, Ar), 6.93 (d, 2H, J=8.3 Hz, Ar), 5.16 (t, 1H, J=7.2 Hz), 3.82 (t, 2H, J=7.6 Hz), 2.14-1.97 (m, 2H), 1.75-1.30 (m, 3H), 1.68 (s, 3H), 1.64 (s, 3H), 1.25-1.10 (m, 2H), 1.06 (d, 3H, J=6.6 Hz); MS (EI) 257.18 (100%).

Part B: Preparation of 4-[(3S)-3,7-dimethyl-6-octenyloxy]benzylamine

Sodium borohydride (NaBH$_4$, 29.4 mmol) was added to a mixture of 4-[(3S)-3,7-dimethyl-6-octenyloxy]cyanobenzene (2.52 g, 9.80 mmol) and anhydrous nickel chloride (NiCl$_2$, 9.8 mmol) in dry ethanol (20 mL). After 2 hours the reaction mixture was filtered over Celite® and the Celite® bed was rinsed with ethanol (2×10 mL). The solution was diluted with water (150 mL) and extracted with ether (3×25 mL). The combined ethereal phase was washed with water, dried over MgSO$_4$, and the solvent was evaporated to afford an oil which was purified by column chromatography (EtOAc-hexane) to give 4-[(3S)-3,7-dimethyl-6-octenyloxy]benzylamine as a colorless oil (1.82 g, 6.97 mmol, 71.1% yield).

$^1$H NMR (CDCl$_3$) δ 6.92 (d, 2H, J=7.9 Hz), 6.61 (d, 2H, J=7.9 Hz), 6.81 (s, 2H, broad), 5.17 (t, 2H, J=7.2 Hz), 4.00-3.80 (m, 6H, J=7.6 Hz), 2.14-1.97 (m, 2H), 1.76-1.32 (m, 3H), 1.66 (s, 3H), 1.64 (s, 3H), 1.25-1.11 (m, 2H), 1.05 (d, 3H, J=6.6 Hz); HRMS (calculated for: C$_{17}$H$_{27}$NO, 261.2093): 261.2099.

Part C: Preparation of N,N'-bis{-4-[(3S)-3,7-dimethyl-6-octenyloxy]benzyl}-1,7-dibromoperylene-3,4:9,10-bis(dicarboxiamide) (PDI1PhOCitr-Br$_2$)

4-[(3S)-3,7-Dimethyl-6-octenyloxy]benzylamine (5.13 g, 19.62 mmol) was added in three portions to a suspension of 1,7-dibromoperylene-3,4:9,10-dianhydride (3.00 g, 5.45 mmol) in propionic acid (60 mL). The reaction mixture was heated under reflux for 14 hours. After cooling to room temperature, the resulting solid was collected by filtration, washed with propionic acid and several times with MeOH, and finally dried overnight. The crude product (4.02 g) was purified by chromatography on silica gel (CH$_2$Cl$_2$) to give N,N'-bis{4-[(3S)-3,7-dimethyl-6-octenyloxy]benzyl}-1,7-dibromoperylene-3,4:9,10-bis(dicarboxiamide) as a red solid (1.46 g, 1.41 mmol, 25.9% yield).

M.p. >250° C. (DMF-xylene); $^1$H NMR (CHCl$_3$, 500 MHz): δ 9.53 (d, 2H, J=7.8 Hz), 8.95 (s, 2H), 8.77 (d, 2H, J=7.8 Hz), 7.23 (d, 4H, J=8.7 Hz), 7.07 (d, 4H, J=8.7 Hz), 5.20 (t, 4H, J=7.3 Hz), 4.00-3.80 (m, 12H, J=7.6 Hz), 2.14-1.97 (m, 4H), 1.76-1.32 (m, 6H), 1.66 (s, 6H), 1.62 (s, 6H), 1.25-1.11 (m, 4H), 1.05 (d, 6H, J=6.6 Hz); Elemental Analysis (calculated for C$_{58}$H$_{56}$Br$_2$N$_2$O$_6$: C, 67.18; H, 5.44; N, 2.70): C, 66.99; H, 5.21; N, 2.42.

Part D: Preparation of N,N'-bis{4-[(3S)-3,7-dimethyl-6-octenyloxy]benzyl}-1,7-dicyanoperylene-3,4:9,10-bis(dicarboxiamide) (PDI1PhOCitr-CN$_2$)

A mixture of N,N'-bis{4-[(3S)-3,7-dimethyl-6-octenyloxy]benzyl}-1,7-dibromoperylene-3,4:9,10-bis(dicarboxiamide) (2.80 g, 2.70 mmol) and CuCN (4.4 g, 49.0 mmol) in DMF (110 mL) was deaerated and placed under nitrogen. The reaction mixture was heated at 150° C. for 7 hours. After cooling to room temperature, the precipitate was collected by filtration, washed several times with MeOH, and dried overnight. The crude solid was purified by multiple crystallization from DMF-toluene to give N,N'-bis{4-[(3S)-3,7-dimethyl-6-octenyloxy]benzyl}-1,7-dicyanoperylene-3,4:9,10-bis(dicarboxiamide) as a red solid (2.21 g, 2.38 mmol, 88.0% yield).

$^1$H NMR (CHCl$_3$, 500 MHz): δ 9.77 (d, 2H, J=8.0 Hz), 9.04 (s, 2H), 9.01 (d, 2H, J=8.0 Hz), 7.37 (d, 4H, J=8.6 Hz), 7.12 (d, 4H, J=8.6 Hz), 5.22 (t, 4H, J=7.5 Hz), 4.02-3.78 (m, 12H, J=7.6 Hz), 2.14-1.97 (m, 4H), 1.75-1.32 (m, 6H), 1.66 (s, 6H), 1.62 (s, 6H), 1.25-1.11 (m, 4H), 1.06 (d, 6H, J=6.8 Hz); Elemental Analysis (calculated for C$_{60}$H$_{56}$N$_4$O$_6$C, 77.56; H, 6.08; N, 6.03): C, 76.98; H, 6.72; N, 5.63.

Example 16

Preparation of N,N'-bis(4-benzylphenyl)-1,7-dicyanoperylene-3,4:9,10-bis(dicarboxiamide) (PDIPh1Ph-CN$_2$)

Part A: Preparation of N,N'-bis(4-benzylphenyl)-1,7-dibromoperylene-3,4:9,10-bis(dicarboxiamide) (PDIPh1Ph-Br$_2$)

4-Benzylaniline (3.60 g, 19.62 mmol) was added in three portions to a suspension of 1,7-dibromoperylene-3,4:9,10-dianhydride (3.00 g, 5.45 mmol) in propionic acid (56 mL). The reaction mixture was heated under reflux for 12 hours. After cooling to room temperature, the resulting solid was collected by filtration, washed with propionic acid and several times with MeOH, and dried overnight. The crude product (3.29 g) was used in the next step without further purification.

M.p.>300° C. (DMF); $^1$H NMR (CHCl$_3$, 300 MHz): δ 9.56 (d, 2H, J=8.1 Hz), 9.01 (s, 2H), 8.81 (d, 2H, J=8.1 Hz), 7.54-7.30 (m, 18H), 4.24 (s, 4H); HRMS (calculated for: C$_{50}$H$_{28}$Br$_2$N$_2$O$_6$ 878.0416): 878.0408.

Part B: Preparation of N,N'-bis(4-benzylphenyl)-1,7-dicyanoperylene-3,4:9,10-bis(dicarboxiamide) (PDIPh1Ph-CN$_2$)

A mixture of crude N,N'-bis(4-benzylphenyl)-1,7-dibromoperylene-3,4:9,10-bis(dicarboxiamide) (3.00 g, 3.41 mmol) and CuCN (5.91 g, 66 mmol) in DMF (140 mL) was deaerated and placed under nitrogen. The reaction mixture was heated at 150° C. for 6 hours. After cooling to room temperature, the precipitate was collected by filtration, washed several times with MeOH, and dried overnight. The crude solid (0.38 g) was recrystallized from DMF to give N,N'-bis(4-benzylphenyl)-1,7-dicyanoperylene-3,4:9,10-bis(dicarboxiamide) as a red powder (0.15 g, 0.19 mmol, 5.6% yield).

M.p.>300° C.; $^1$H NMR (CHCl$_3$, 400 MHz): δ 9.76 (d, 2H, J=7.6 Hz), 9.04 (s, 2H), 8.99 (d, 2H, J=8.4 Hz), 7.42 (d, 4H, J=7.6 Hz), 7.35 (d, 4H, J=5.6 Hz), 7.30-7.20 (m, 8H), 4.12 (s, 4H); Elemental Analysis (calculated for C$_{52}$H$_{28}$N$_4$O$_4$: 80.82; H, 3.65; N, 7.25): C, 81.07; H, 3.97; N, 7.11.

Example 17

Preparation of N,N'-bis{4-[1-(2-phenylethyl)]phenyl}-1,7-dicyanoperylene-3,4:9,10-bis(dicarboxiamide) (PDIPh2Ph-CN$_2$)

Part A: Preparation of N,N'-bis{-4-[1-(2-phenylethyl)]phenyl}-1,7-dibromoperylene-3,4:9,10-bis(dicarboxiamide) (PDIPh2Ph-Br$_2$)

4-[1-(2-Phenylethyl)]aniline (3.77 g, 19.12 mmol) was added to a suspension of 1,7-dibromoperylene-3,4:9,10-dianhydride (4.00 g, 4.78 mmol) in propionic acid (50 mL). The reaction mixture was heated under reflux for 24 hours. After cooling to room temperature, the resulting solid was collected by filtration, washed with propionic acid and several times with MeOH, and dried overnight. The crude product (6.08 g) was purified by chromatography on silica gel (CHCl$_3$:acetone—50:50) to give N,N'-bis{4-[1-(2-phenylethyl)]phenyl}-1,7-dibromoperylene-3,4:9,10-bis(dicarboxiamide) as a red solid (0.725 g, 0.80 mmol, 16.7% yield).

M.p.>250° C. (DMF); $^1$H NMR (CHCl$_3$, 300 MHz): δ 9.54 (d, 2H, J=8.0 Hz), 8.97 (s, 2H), 8.75 (d, 2H, J=8.0 Hz), 7.40-7.10 (m, 16H), 2.80-2.72 (m, 8H); Elemental Analysis (calculated for: C$_{52}$H$_{32}$Br$_2$N$_2$O$_4$C, 68.74; H, 3.55; N, 3.08): C, 69.08; H, 3.70; N, 3.29.

Part B: Preparation of N,N'-bis{4-[1-(2-phenylethyl)]phenyl}-1,7-dicyanoperylene-3,4:9,10-bis(dicarboxiamide) (PDIPh2Ph-CN$_2$)

A mixture of N,N'-bis{4-[1-(2-phenylethyl)]phenyl}-1,7-dibromoperylene-3,4:9,10-bis(dicarboxiamide) (3.49 g, 3.84 mmol) and CuCN (6.43 g, 72.0 mmol) in DMF (150 mL) was deaerated and placed under nitrogen. The reaction mixture was heated at 150° C. for 6 hours. After cooling to room temperature, the precipitate was collected by filtration, washed several times with MeOH, and dried overnight. The crude solid was recrystallized from DMF to give N,N'-bis{4-[1-(2-phenylethyl)]phenyl}-1,7-dicyanoperylene-3,4:9,10-bis(dicarboxiamide) as a red powder (2.02 g, 2.52 mmol, 65.7% yield).

M.p.>300° C. (DMF); $^1$H NMR (CHCl$_3$, 400 MHz): δ 9.78 (d, 2H, J=8.0 Hz), 9.06 (s, 2H), 9.01 (d, 2H, J=8.4 Hz), 7.42-7.10 (m, 16H), 2.80-2.72 (m, 8H); Elemental Analysis (calculated for: C$_{54}$H$_{32}$N$_4$O$_4$C, 80.99; H, 4.03; N, 7.00): C, 81.43; H, 4.38; N, 6.76.

Example 18

Preparation of N,N'-bis(4-n-benzoylphenyl)-1,7-dicyanoperylene-3,4:9,10-bis(dicarboxiamide) (PDIPhCOPh-CN$_2$)

Part A: Preparation of N,N'-bis(4-benzoylphenyl)-1,7-dibromoperylene-3,4:9,10-bis(dicarboxiamide) (PDIPhCOPh-Br$_2$)

4-Aminobenzophenone (3.87 g, 19.62 mmol) was added in three portions to a suspension of 1,7-dibromoperylene-3,4:9,10-dianhydride (3.00 g, 5.45 mmol) in propionic acid (56 mL). The reaction mixture was heated under reflux for 12 hours. After cooling to room temperature, the resulting solid was collected by filtration, washed with propionic acid and several times with MeOH, and dried overnight. The crude product (3.48 g) was purified by chromatography on silica gel (CH$_2$Cl$_2$) to give N,N'-bis(4-benzoylphenyl)-1,7-dibromoperylene-3,4:9,10-bis(dicarboxiamide) as a red solid (0.67 g, 0.74 mmol, 13.6% yield).

M.p.>300° C. (DMF); $^1$H NMR (CHCl$_3$, 400 MHz): δ 9.58 (d, 2H, J=8.0 Hz), 9.01 (s, 2H), 8.80 (d, 2H, J=8.4 Hz), 8.05 (d, 4H, J=8.4 Hz), 7.91 (d, 4H, J=7.6 Hz), 7.65 (t, 2H, J=6.8 Hz), 7.56-7.48 (m, 8H); HRMS (calculated for: C$_{50}$H$_{24}$Br$_2$N$_2$O$_6$ 906.0001): 906.0008; Elemental Analysis (calculated for C$_{50}$H$_{24}$Br$_2$N$_2$O$_6$: C, 66.10; H, 2.66; N, 3.08): C, 66.58; H, 2.53; N, 3.27.

Part B: Preparation of N,N'-bis(4-n-benzoylphenyl)-1,7-dicyanoperylene-3,4:9,10-bis(dicarboxiamide) (PDIPhCOPh-CN$_2$)

A mixture of N,N'-bis(4-benzoylphenyl)-1,7-dibromoperylene-3,4:9,10-bis(dicarboxiamide) (0.60 g, 0.66 mmol) and CuCN (1.07 g, 12.0 mmol) in DMF (27 mL) was deaerated and placed under nitrogen. The reaction mixture was heated at 150° C. for 6 hours. After cooling to room temperature, the precipitate was collected by filtration, washed several times with MeOH, and dried overnight. The crude solid (0.42 g) was insoluble in common organic solvents.

HRMS (calculated for C$_{52}$H$_{24}$O$_6$N$_4$: 800.1690): 800.1687.

Example 19

Preparation of N,N'-{4-[(3S)-3,7-dimethyl-6-octenyl]phenyl}-2,6-dicyanonapthalene-1,4:5,8-tetracarboxylicdiimide (NDICitr-CN$_2$)

Part A: Preparation of 2,6-dibromonapthalene-1,4:5,8-tetracarboxylicdianhydride (NDA-Br$_2$)

To a 500 mL round bottom flask was added naphthalene 1,2:5,6-tetracarboxylic dianhydride (19.8 g, 73.8 mmol) and oleum (400 mL). The suspension was stirred for 3 hours, followed by addition of iodine (0.812 g, 3.20 mmol). Stirring was continued for an additional hour. To the reaction mixture, bromine (8 mL, 156 mmol) was added dropwise over 15 minutes. The reaction mixture was then heated to 95° C. under nitrogen for 72 hours and allowed to cool to room temperature. Next, 300 mL of ice water was added to a 600 mL beaker, and the reaction mixture was slowly poured into the ice water. The resulting yellow precipitate was collected by filtration, washed with MeOH (3×15 mL), and dried to yield 24.1 g of crude product. The product was used crude for subsequent steps.

MALDI-TOF-MS (calculated: 426.97): 426.91.

Part B: Preparation of N,N'-{4-[(3S)-3,7-dimethyl-6-octenyl]phenyl}-2,6-dibromonapthalene-1,4:5,8-tetracarboxylicdiimide (NDICitr-Br$_2$)

A mixture of 2,6-dibromonapthalene-1,4:5,8-tetracarboxylicdianhydride (2.00 g, 4.70 mmol) and 4-[(3S)-3,7-dimethyl-6-octenyl]aniline (10.87 g, 47 mmol) in N-methyl pyrollidinone (70 mL) and glacial acetic acid (40 mL) was stirred at 85° C. under nitrogen for 8 hours. After cooling to room temperature, the reaction mixture was poured into 200 mL of MeOH and placed in a freezer overnight. The resulting precipitate was collected by filtration, washed with MeOH, and dried. The crude orange product was then purified by chromatography on silica gel (CH$_2$Cl$_2$) to give N,N'-{4-[(3S)-3,7-dimethyl-6-octenyl]phenyl}-2,6-dibromonapthalene-1,4:5,8-tetracarboxylicdiimide as a bright yellow solid (1.57 g, 1.84 mmol, 39.1% yield).

$^1$H NMR (CDCl$_3$): δ 8.98 (s, 2H), 7.44 (d, 4H, J=8.1 Hz), 7.23 (d, 4H, J=8.1 Hz), 5.17 (t, 2H, J=7.1 Hz), 2.72 (t, 4H, J=7.8 Hz), 2.16-1.96 (m, 4H), 1.80-1.40 (m, 6H), 1.66 (s, 6 H), 1.64 (s, 6H), 1.40-1.20 (m, 4H), 1.04 (d, 6H, J=6.5 Hz); HRMS (calculated for C$_{46}$H$_{48}$Br$_2$N$_2$O$_4$: 850.1981): 850.1987.

Part C: Preparation of N,N'-{4-[(3S)-3,7-dimethyl-6-octenyl]phenyl}-2,6-dicyanonapthalene-1,4:5,8-tetracarboxylicdiimide (NDICitr-CN$_2$)

A mixture of N,N'-{4-[(3S)-3,7-dimethyl-6-octenyl]phenyl}-2,6-dibromonapthalene-1,4:5,8-tetracarboxylicdiimide (1.53 g, 1.80 mmol) and CuCN (1.72 g, 19.2 mmol) in DMF (60 mL) was stirred under nitrogen for 5 hours at 150° C. The reaction mixture was cooled with an ice bath and a precipitate formed. The precipitate was filtered and washed several times with MeOH. The crude solid was purified by chromatography on silica gel (CH$_2$Cl$_2$) to give N,N'-{4-[(3S)-3,7-dimethyl-6-octenyl]phenyl}-2,6-dicyanonapthalene-1,4:5,8-tetracarboxylicdiimide which was additionally crystallized with DMF (0.21 mg, 0.29 mmol, 16% yield).

$^1$H NMR (CDCl$_3$): δ 9.12 (s, 2H), 7.45 (d, 4H, J=8.1 Hz), 7.22 (d, 4H, J=8.1 Hz), 5.18 (t, 2H, J=7.1 Hz), 2.72 (t, 4H, J=7.8 Hz), 2.16-1.96 (m, 4H), 1.82-1.40 (m, 6H), 1.66 (s, 6 H), 1.64 (s, 6H), 1.40-1.20 (m, 4H), 1.01 (d, 6H, J=6.6 Hz); Elemental Analysis (calculated for C$_{48}$H$_{48}$N$_4$O$_4$: C, 77.39; H, 6.49; N, 7.52): C, 77.81; H, 6.12; N, 7.09.

Example 20

Preparation of N,N'-bis{4-[(3S)-3,7-dimethyl-6-octenyl]phenyl}-2,3:6,7-anthracenedicarboximide Sodium iodide (3.7 g) was added to a solution of 1,2,4,5-tetrakis(dibromomethyl)benzene (1.92 g, 2.50 mmol) and N-{4-[(3S)-3,7-dimethyl-6-octenyl]}phenylmaleimide (1.56 g, 5.00 mmol) in N,N-dimethylacetamide (15 mL). The reaction mixture was heated at 85° C. for 16 hours during which time a precipitate formed. The solid was collected by filtration, washed with water and MeOH, and finally dried to give N,N'-bis{4-[(3S)-3,7-dimethyl-6-octenyl]phenyl}-2,3:6,7-anthracenedicarboximide as a bright yellow solid (0.51 g, 0.68 mmol, 27% yield). Additional purification can be achieved by recrystallization from DMF-TCB.

$^1$H NMR (400 MHz, CDCl$_3$): δ 8.83 (s, 2H), 8.61 (s, 4H), 7.39 (d, 4H, J=8.0 Hz), 7.21 (d, 4H, J=8.0 Hz), 5.20 (t, 2H, J=7.2 Hz), 2.71 (t, 4H, J=7.6 Hz), 2.16-1.96 (m, 4H), 1.82-1.40 (m, 6H), 1.67 (s, 6H), 1.63 (s, 6H), 1.40-1.20 (m, 4H), 1.02 (d, 6H, J=6.6 Hz); Elemental Analysis (calculated for C$_{50}$H$_{52}$O$_4$N$_2$: C, 80.61; H, 7.04; N, 3.76); C, 80.55; H, 7.38; N, 4.04.

Example 21

Preparation of N,N'-bis(2-ethylhexyl)-1,7-dicyanoperylene-3,4:9,10-bis(dicarboxiamide) (PDI2EH-CN$_2$)

Part A: Preparation of N,N'-bis(2-ethylhexyl)-1,7-dibromoperylene-3,4:9,10-bis(dicarboxiamide) (PDI2EH—Br$_2$)

1,7-Dibromoperylene-3,4:9,10-dianhydride (PDABr$_2$) (5.10 g, 9.35 mmol) was mixed with 2-ethylhexylamine (5.60 mL, 34.2 mmol) in propionic acid (80 mL). The reaction mixture was heated under reflux for 16 hours. After cooling to room temperature, the resulting solid was collected by filtration, washed with propionic acid and several times with MeOH, and dried overnight. Filtration afforded 7.57 g of crude product, which was purified by column chromatography (CHCl$_3$) to give PDI2EH—Br$_2$ as a red solid (5.12 g, 6.63 mmol, yield 65.2%).

M.p. >200° C.; $^1$H NMR (CDCl$_3$, 500 MHz): δ 9.48 (d, 2H, J=8.0 Hz), 8.92 (s, 2H), 8.69 (d, 2H, J=8.0 Hz), 4.20-4.11 (m, 4H), 2.00-1.92 (m, 2H), 1.50-1.35 (m, 8H), 1.35-1.24 (m, 8H), 0.96 (d, 6H, J=7.5 Hz), 0.91 (t, 6H, J=7.0 Hz); Elemental Analysis (calculated: C, 62.19; H, 5.22; N, 3.63): C, 62.20; H, 5.43; N, 3.33.

Part B: Preparation of N,N'-bis(2-ethylhexyl)-1,7-dicyanoperylene-3,4:9,10-bis(dicarboxiamide) (PDI2EH-CN$_2$)

Under nitrogen, CuCN (2.28 g, 25.3 mmol) was added to the mixture of PDI2EH—Br$_2$ (1.08 g, 1.40 mmol) and DMF (54 mL). The mixture was heated to 150° C. and stirred overnight. After cooling to room temperature, the solid was filtered and washed several times with MeOH. The crude product (1.03 g) was purified by column chromatography (CHCl$_3$/acetone; 96:4) to afford about 0.8 g of a red solid.

After one recrystallization from 20 mL DMF, PDI2EH-CN$_2$ was obtained as a red solid (560 mg, yield 60%).

M.p. 319-321° C.; $^1$H NMR (CDCl$_3$, 500 MHz): δ 9.52 (d, 2H, J=8.0 Hz), 8.91 (s, 2H), 8.70 (d, 2H, J=8.0 Hz), 4.20-4.10 (m, 4H), 2.00-1.91 (m, 2H), 1.50-1.35 (m, 8H), 1.35-1.25 (m, 8H), 0.98 (d, 6H, J=7.5 Hz), 0.90 (t, 6H, J=7.0 Hz); Elemental Analysis (calculated: C, 75.88; H, 6.06; N, 8.43): C, 75.85; H, 5.93; N, 8.33.

Example 22

Preparation of N,N'-bis(2-methylhexyl)-1,7-dicyanoperylene-3,4:9,10-bis(dicarboxiamide) (PDI2MH—CN$_2$)

Part A: Preparation of 2-methylhexanenitrile

To a solution of i-PrNH$_2$ (9.11 g, 12.7 mL, 90 mmol) in dry THF (80 mL) cooled to −78° C. was added a solution of n-BuLi (57 mL, 1.59 M, 90 mmol) in hexane dropwise over a period of 5 minutes. After 15 minutes at bath temperature, 4.63 g (6.0 mL, 84 mmol) of propionitrile was added dropwise over a period of 15 minutes. The pale yellow reaction mixture was stirred at −78° C. for 1 hour and then a solution of n-BuBr (12.33 g, 9.7 mL, 90 mmol) in dry THF (10 mL) was added dropwise. The bath was allowed to warm to room temperature and the mixture was stirred overnight. Hydrochloric acid (40 mL, 1N) then was added. The mixture was concentrated in vacuo to approximately 100 mL, and partitioned in ether (150 mL) and water (30 mL). The organic phase was dried over Na$_2$SO$_4$ and concentrated as a yellow oil. Distillation under vacuum at 72° C. gave 2-methylhexanenitrile as a colorless liquid (3.76 g, 34 mmol, yield 40.5%).

Part B: Synthesis of 2-methylhexylamine

To an ice-bath cooled solution of lithium aluminum hydride (1.29 g, 34 mmol) in dry ether (68 mL) was slowly added 2-methylhexanenitrile (3.76 g, 34 mmol) dissolved in dry ether (7 mL). The reaction mixture was allowed to stir for 2 hours. With continued cooling and vigorous stirring, water (1.4 mL), aqueous NaOH solution (1.1 mL, 20%), and water (5.0 mL) were added in succession. The ether solution was decanted from the white, granular inorganic residue. This residue was washed twice with ether and all the ether portions were combined. The ether was distilled off to give the crude 2-methylhexylamine as a colorless liquid (3.09 g, 27 mmol, yield 78.8%).

Part C: Preparation of N,N'-bis(2-methylhexyl)-1,7-dibromoperylene-3,4:9,10-bis(dicarboxiamide) (PDI2MH—Br$_2$)

PDABr$_2$ (1.00 g, 1.82 mmol) and 2-methylhexylamine (503 mg, 0.52 mL, 4.37 mmol) in propionic acid (20 mL) was stirred at 140° C. for 6 hours. After cooling to room temperature, the solvent was removed to give a residue (1.09 g). The residue was purified by column chromatography (CHCl$_3$) to afford PDI2MH—Br$_2$ as a red solid (500 mg, 0.67 mmol, yield 36.9%).

M.p. >200° C.; $^1$H NMR (CDCl$_3$, 500 MHz): δ 9.49 (d, 2H, J=7.0 Hz), 8.93 (s, 2H), 8.70 (d, 2H, J=7.5 Hz), 4.11 (d, 4H, J=7.5 Hz), 2.16-2.05 (m, 2H), 1.47-1.39 (m, 4H), 1.37-1.24 (m, 4H), 0.95 (d, 6H, J=7.0 Hz), 0.90 (t, 6H, J=6.5 Hz); Elemental analysis (calculated: C, 61.30; H, 4.87; N, 3.76): C, 61.65; H, 4.57; N, 3.91.

Part D: Preparation of N,N'-bis(2-methylhexyl)-1,7-dicyanoperylene-3,4:9,10-bis(dicarboxiamide) (PDI2MH—CN$_2$)

Under nitrogen, CuCN (1.48 g, 16.4 mmol) was added to a mixture of PDI2MH—Br$_2$ (670 mg, 0.90 mmol) and DMF (32 mL). The mixture was heated to 150° C. and stirred overnight. After cooling to room temperature, the solid was collected by filtration and washed several times with MeOH. The crude product (480 mg) was purified by column chromatography (CHCl$_3$/acetone; 96:4) to give about a red solid (330 mg). After one recrystallization from DMF (10 mL), PDI2MH—CN$_2$ was obtained as a red solid (320 mg, 0.50 mmol, yield 56%).

M.p. >240° C.; $^1$H NMR (CDCl$_3$, 500 MHz): δ 9.71 (d, 2H, J=7.5 Hz), 9.00 (s, 2H), 8.94 (d, 2H, J=9.0 Hz), 4.13 (d, 4H, J=7.5 Hz), 2.16-2.08 (m, 2H), 1.50-1.40 (m, 4H), 1.39-1.25 (m, 4H), 0.96 (d, 6H, J=7.5 Hz), 0.91 (t, 6H, J=7.5 Hz); Elemental analysis (calculated: C, 75.45; H, 5.70; N, 8.80): C, 75.43; H, 5.68; N, 8.82.

Example 23

Solubility Data

Solubility data were obtained for compounds of the present teachings in various organic common solvents (Table 3). N,N'-bis(4-n-octyl)-1,7-dicyanoperylene-3,4:9,10-bis(dicarboxiamide) (PDI8-CN$_2$) was included as a comparative compound. In particular, it should be noted that rylene compound having 3-alkyl substituted alkenyl group functionalization of the imide nitrogens (PDICitr-CN$_2$) showed an unexpected increase in solubility compared to a similar compound having a common known linear alkyl group substitution (PDI8-CN$_2$) as well as compared to the other representative compounds of the present teachings found in Table 3.

TABLE 3

| Compound | Temperature Range (° C.) | Solubility (mg/mL) | |
|---|---|---|---|
| | | Chloroform | Xylene |
| PDI8-CN$_2$ | 25-80 | 4-5 | 2-3 |
| PDICitr-CN$_2$ | 25-100 | 40-60 | 40-65 |
| PDIPh6-CN$_2$ | 25-100 | 2-5 | 7-8 |
| PDIPh12-CN$_2$ | 25-800 | 2-3 | 8-9 |
| PDIPhCitr-CN$_2$ | 25-100 | 10-20 | 15-25 |
| PDIPhO7-CN$_2$ | 25-100 | 1-2 | 2-3 |
| PDIPhPh-CN$_2$ | 25-100 | <1 | <1 |
| PDIPhPh8-CN$_2$ | 25-100 | 1-2 | 2-3 |
| PDIPhPhCitr-CN$_2$ | 25-100 | 8-12 | 10-12 |
| PDI1Ph-CN$_2$ | 25-100 | <1 | <1 |
| PDI1Ph4-CN$_2$ | 25-800 | 2-3 | 5-6 |
| PDIPhs4-CN$_2$ | 25-80 | <1 | <1 |
| PDI1PhOCitr-CN$_2$ | 25-100 | 12-20 | 15-25 |
| PDIPh2Ph-CN$_2$ | 25-60 | 2-4 | 3-7 |

Example 24

Thin Film Semiconductor Fabrication

Organic semiconductor thin films were fabricated by vapor deposition and solution phase deposition. Evaporated films were prepared in a Denton DV-502 vacuum deposition apparatus ($10^{-6}$-$10^{-7}$ Torr) on substrates kept at 25-120° C.

Organic semiconductor films were deposited on the following substrates: n$^+$-Si-(300 nm)SiO$_2$ (Process Specialties Inc.), ITO, ITO-(100-600 nm) CPB dielectric (Polyera Corporation), PET-Al-(100-600 nm) CPB dielectric (Polyera Corporation). These were rinsed with water, methanol, and acetone before CPB or organic semiconductor film deposition. Silane functionalization of the Si/SiO$_2$ surface was carried out by exposing the silicon-oxide wafers to hexamethyldisilazane (HMDS) and octadecyltrichlorosilane (OTS) vapor at room temperature in a closed container under nitrogen.

The growth rate of the films (0.1-0.4 Å/s) was controlled by adjusting the crucible temperature. A calibrated quartz-crystal microbalance was used to control the growth rate and film thickness. Solution-deposited films were fabricated by drop-casting (semiconductor concentration=0.1-2 mg/mL), spin-coating (semiconductor concentration=1-10 mg/mL, spin rate=500-5000 rpm), gravure/flexo printing (semiconductor concentration=10-130 mg/mL, anilox/printing force=10-500 N, printing speed=0.2-1.5 m/s), and inkjet printing (semiconductor concentration=1-10 mg/mL).

Figure 4:
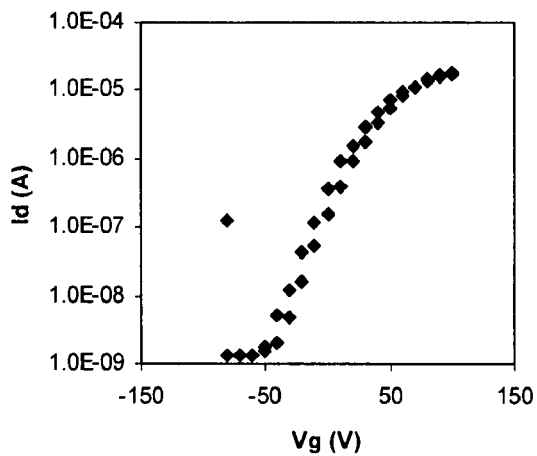
FIG. 4 is a representative transfer plot of a compound of the present teachings (PDIPhPh-$CN_2$). The semiconductor material was deposited from solution.
Figure 5:
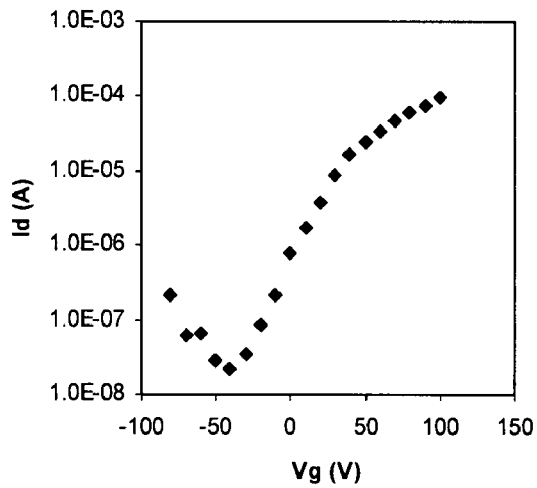
FIG. 5 is a representative transfer plot of a compound of the present teachings (PDIPhPh8-$CN_2$). The semiconductor material was deposited from solution.
Figure 6:
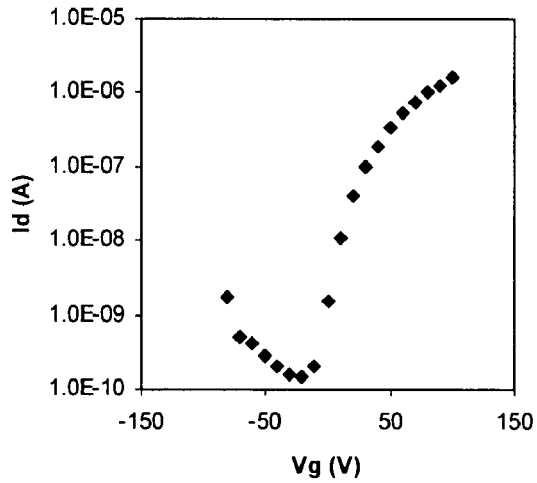
FIG. 6 is a representative transfer plot of a compound of the present teachings (PDIPh6-$CN_2$). The semiconductor material was deposited from solution.
Figure 7:
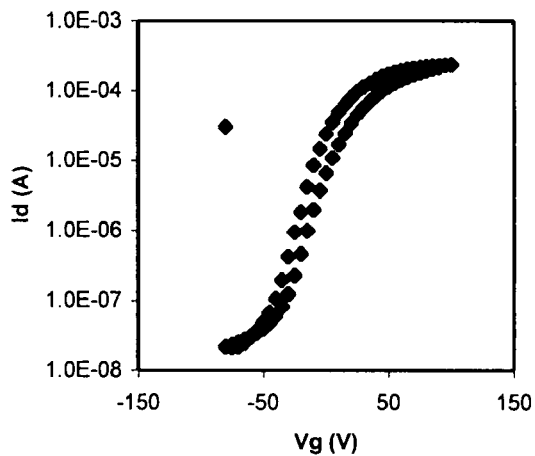
FIG. 7 is a representative transfer plot of a compound of the present teachings (PDIPhPhCitr-$CN_2$). The semiconductor material was deposited from solution.
Figure 8:
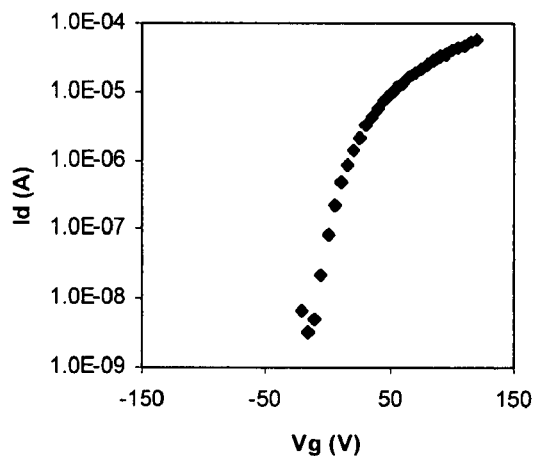
FIG. 8 is a representative transfer plot of a compound of the present teachings (PDIPhCitr-$CN_2$). The semiconductor material was deposited from solution.

Transfer plots were obtained for the following thin film semiconductors deposited from solution phase: PDIPhPh-CN$_2$ (FIG. 4), PDIPhPh8-CN$_2$ (FIG. 5), PDIPh6-CN$_2$ (FIG. 6), PDIPhPhCitr-CN$_2$ (FIG. 7), and PDIPhCitr-CN$_2$ (FIG. 8).

Figure 9:
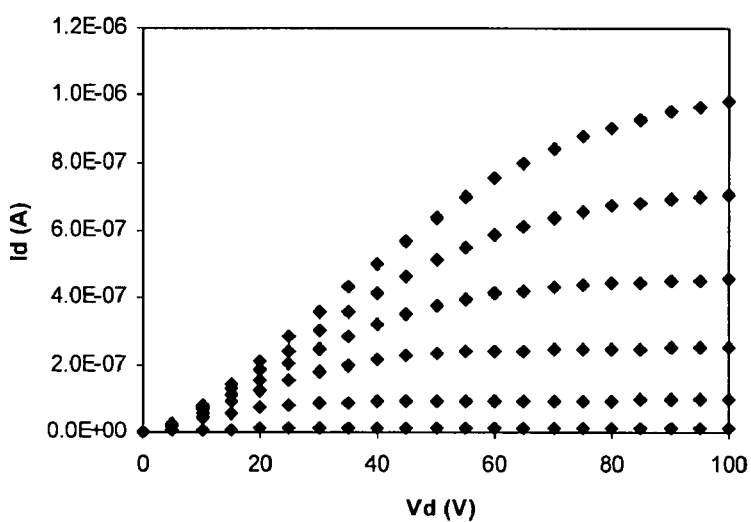
FIG. 9 is a representative output plot of a compound of the present teachings (PDIPhCitr-$CN_2$). The semiconductor material was deposited from solution.
Figure 10:
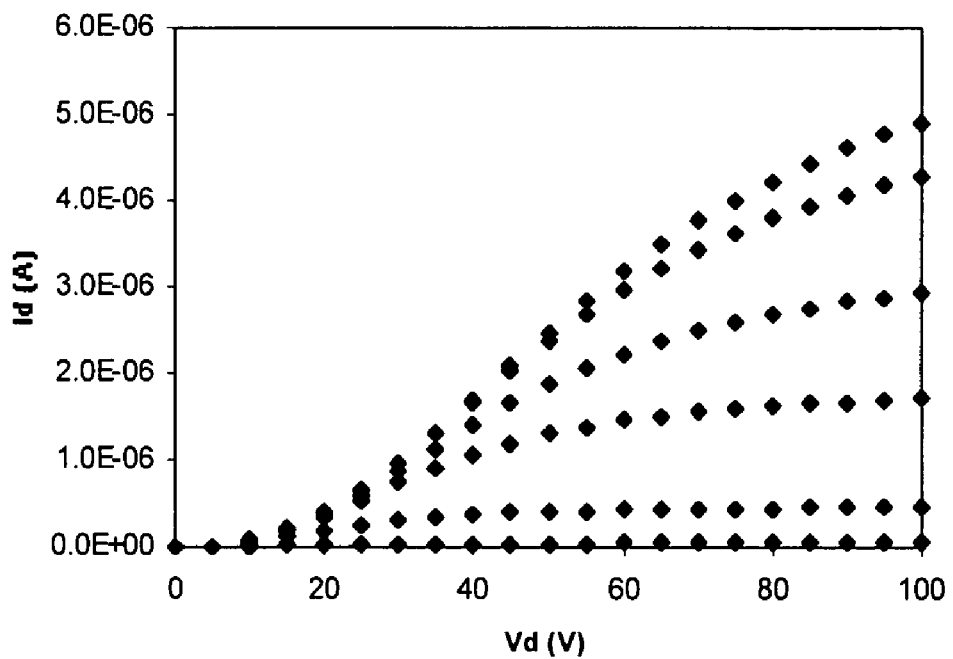
FIG. 10 is a representative output plot of a compound of the present teachings (PDIPhPh-$CN_2$). The semiconductor material was deposited from solution.
Figure 11:
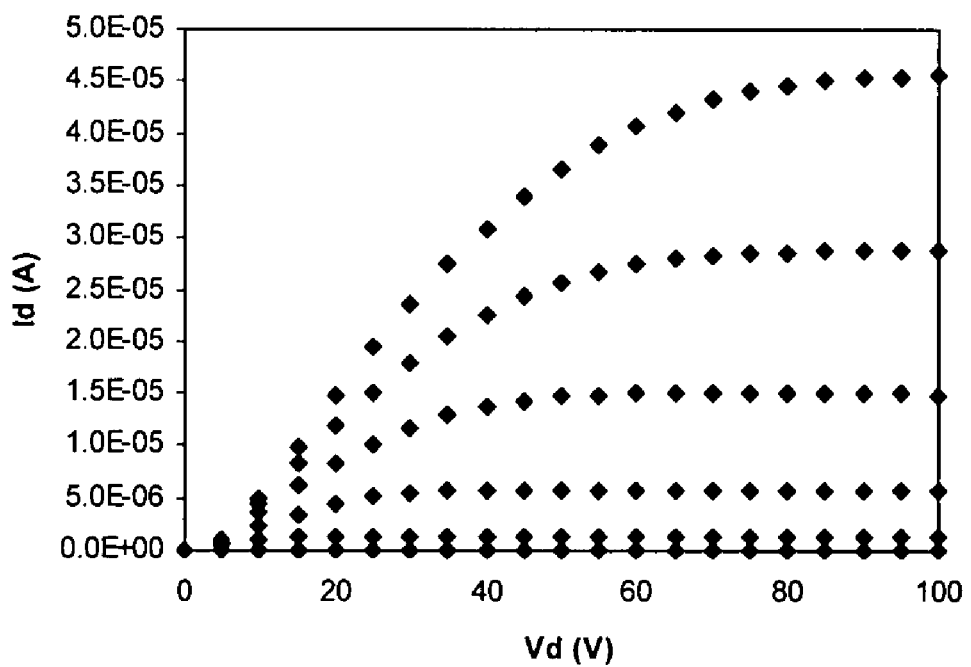
FIG. 11 is a representative output plot of a compound of the present teachings (PDIPh12-$CN_2$). The semiconductor material was deposited from solution.
Figure 12:
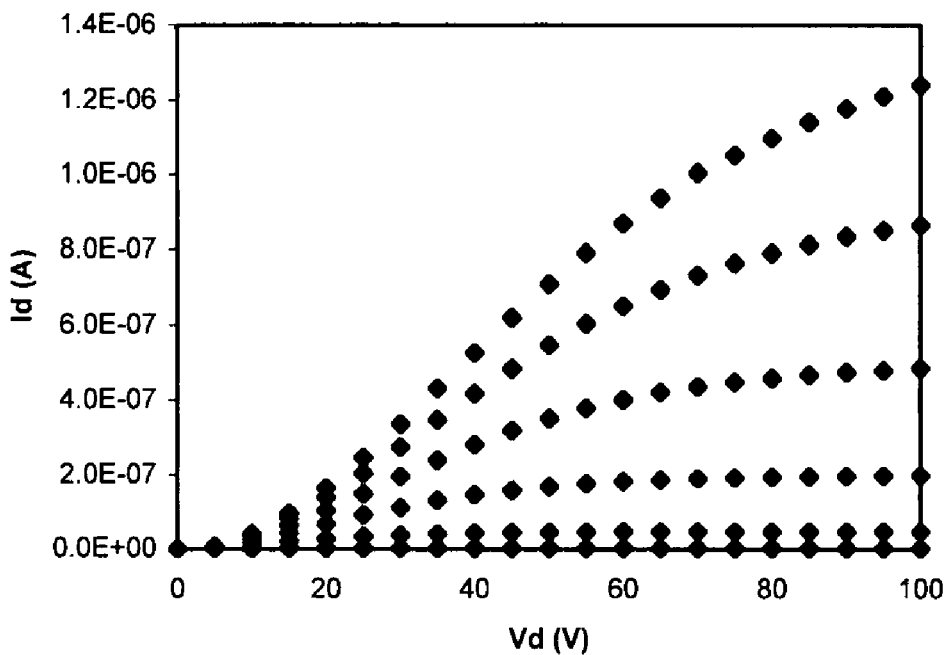
FIG. 12 is a representative output plot of a compound of the present teachings (PDIPhPhCitr-$CN_2$). The semiconductor material was deposited from solution.
Figure 13:
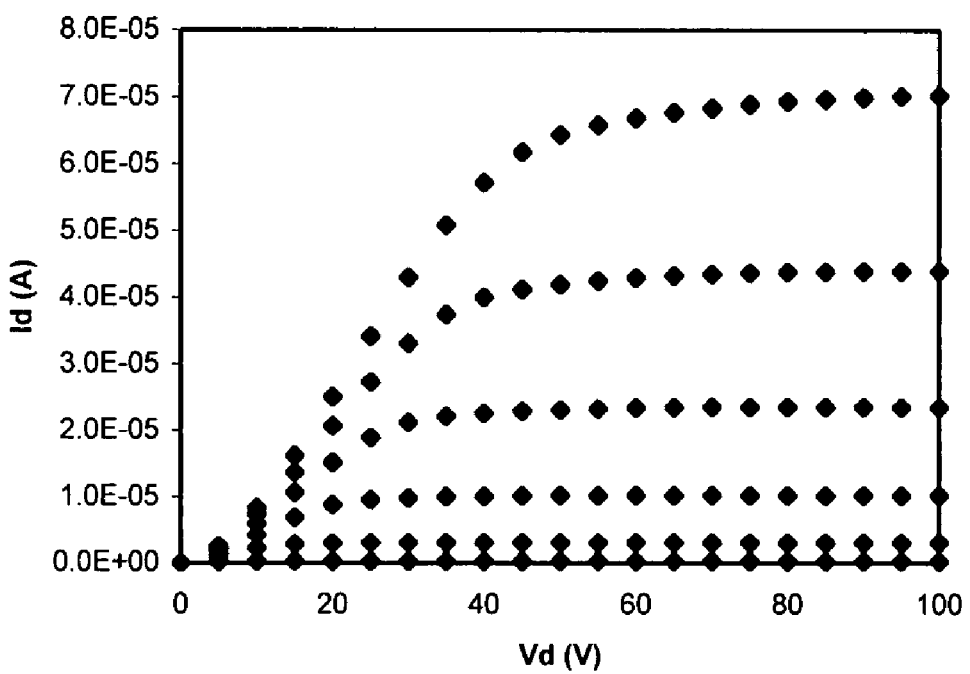
FIG. 13 is a representative output plot of a compound of the present teachings (PDIPh12-$CN_2$). The semiconductor material was deposited from the vapor phase.

Output plots were obtained for the following thin film semiconductors deposited from solution phase and vapor phase: PDIPhCitr-CN$_2$— solution (FIG. 9), PDIPhPh-CN$_2$— solution (FIG. 10), PDIPh12-CN$_2$— solution (FIG. 11), PDIPhPhCitr-CN$_2$— solution (FIG. 12), and PDIPh12-CN$_2$— vapor (FIG. 13).

Example 25

Characterization of the Organic Semiconductor Thin Films

Figure 14:
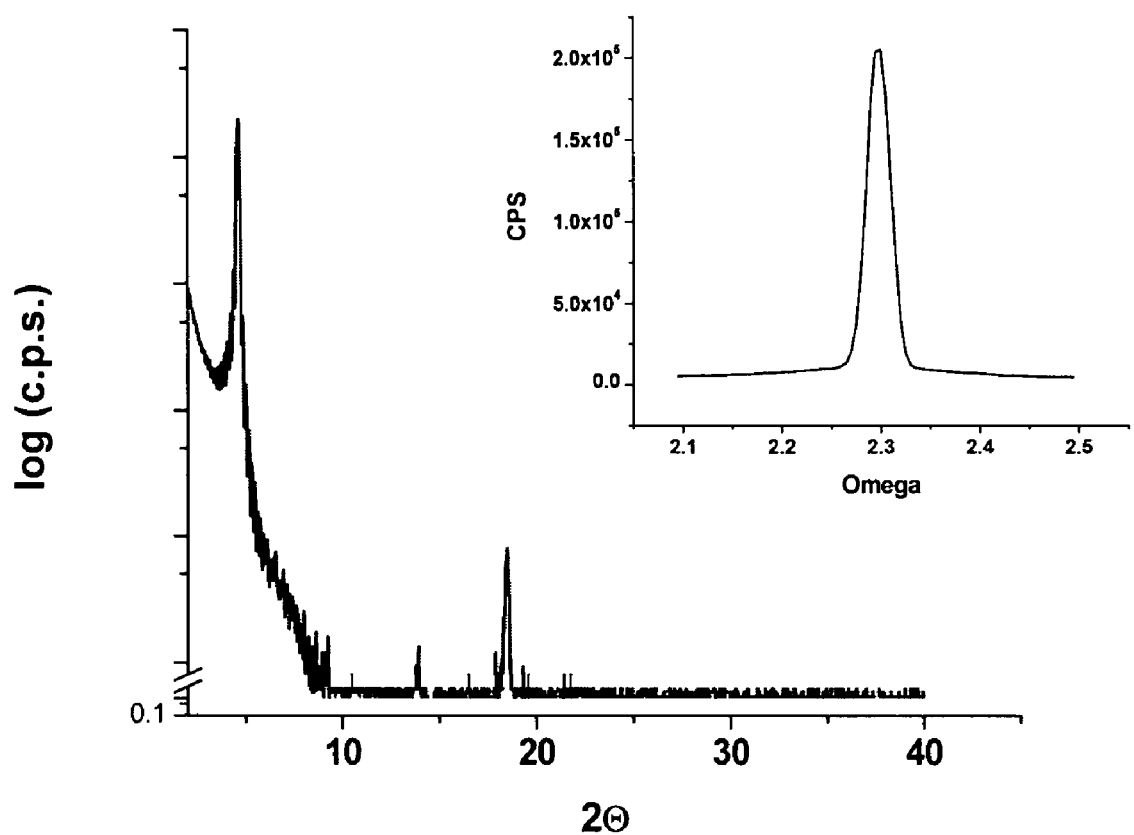
FIG. 14 is the Wide Angle X-Ray Diffraction (WAXRD) Θ/2Θ scan (and rocking curve of the 001 reflection) of a 50 nm-thick film of a compound of the present teachings (PDI1Ph4-$CN_2$).

Thin films (500 Å) were analyzed by X-ray film diffractometry (XRD), using standard θ-2θ techniques, with Cu Kα radiation and a monochromator. All θ-2θ scans were calibrated with the reflection of the Si (100) substrates. FIG. 14 provides the WAXRD Θ/2Θ scan (and rocking curve of the 001 reflection) of a 50 nm-thick film prepared from PDI1Ph4-CN$_2$, which show high degrees of film texture. FIGS. 15A and 15B provide comparative WAXRD Θ/2Θ scans for a solution-phase deposited film versus a vapor-phase deposited film prepared from PDIPhPh-CN$_2$. As demonstrated, regardless of the deposition method, both films are highly crystalline.

Example 26

Thin-Film Transistor Fabrication and Characterization Using Organic Semiconductor Thin Films For thin-film transistor device fabrication, top-contact electrodes (500 Å) were deposited by evaporating gold (pressure <10$^{-5}$ Torr) on top of the gate (Si, ITO, Al)-dielectric (SiO2, CPB)-organic semiconductor samples. TFT device channel dimensions are 50-500 μm (L) by 0.5-4.0 mm (W). The capacitance of the employed insulators are 4-11 nF/cm$^2$. Electrical measurements were performed using a home-built coaxial probe station employing a Keithley 6430 subfemtoammeter and Keithley 2400 source meter, operated by a local Labview program and GPIB communication. Triaxial and/or coaxial shielding was incorporated into the Signaton probe station to minimize noise.

To allow comparison with other organic FETs, mobilities (μ) were calculated by standard field effect transistor equations. In traditional metal-insulator-semiconductor FETs (MISFETs), there is typically a linear and saturated regime in the $I_{DS}$ vs $V_{DS}$ curves at different $V_G$ (where $I_{DS}$ is the source-drain saturation current; $V_{DS}$ is the potential between the source and drain, and $V_G$ is the gate voltage). At large $V_{DS}$, the current saturates and is given by:

$$(I_{DS})_{sat} = (WC_i/2L)\mu(V_G - V_t) \qquad (1)$$

where L and W are the device channel length and width, respectively, $C_i$ is the capacitance of the oxide insulator (1×10$^{-8}$ F/cm$^2$ for 300 nm SiO$_2$), and $V_t$ is the threshold voltage.

Mobilities (μ) were calculated in the saturation regime by rearranging equation 1:

$$\mu_{sat} = (2I_{DS}L)/[WC_i(V_G - V_t)^2] \qquad (2)$$

where $C_i$, in this case, was 6·10$^{-8}$ F. The threshold voltage ($V_t$) can be estimated as the x intercept of the linear section of the plot of $V_G$ versus $(I_{DS})^{1/2}$ (at $V_{SD}$=−100 V).

Table 4 summarizes electron mobilities and current $I_{on}$:$I_{off}$ ratios for representative compounds of the present teachings having been drop-casted and/or vapor-phase deposited to form thin film semiconductors. In particular, it should be noted that rylene compounds having 2-alkyl substituted alkyl group functionalization of the imide nitrogens (PDI2MH—CN$_2$ and PDI2EH-CN$_2$) showed an unexpected increase in current $I_{on}$:$I_{off}$ ratio compared to similar compounds having a common known linear alkyl group substitution (PDI8-CN$_2$) and a branched alkenyl group having a methyl group at its 3-position (PDICitr-CN$_2$).

TABLE 4

| Semiconductor Compound | Dielectric | Semiconductor Deposition | | | |
|---|---|---|---|---|---|
| | | Drop-casting | | Vapor-phase | |
| | | μ (cm$^2$/Vs) | log($I_{on}$:$I_{off}$) | μ (cm$^2$/Vs) | log($I_{on}$:$I_{off}$) |
| PDI8-CN$_2$ | SiO$_2$, SiO$_2$-HMDS, SiO$_2$-OTS, CPB | 0.01-0.2 | 4-5 | 0.1-0.2 | 4-5 |
| PDICitr-CN$_2$ | SiO$_2$, SiO$_2$-HMDS, SiO$_2$-OTS | 0.001-0.1 | 3-5 | 0.01-0.1 | 3-5 |
| PDI2EH-CN$_2$ | SiO$_2$, SiO$_2$-HMDS | 0.01-0.2 | 5-7 | 0.1-0.3 | 6-8 |
| PDI2MH-CN$_2$ | SiO$_2$-OTS | 0.05-0.1 | 6-7 | 0.1-0.2 | 6-7 |
| PDIPh6-CN$_2$ | SiO$_2$-HMDS, SiO$_2$-OTS | 0.05-0.1 | 4-5 | 0.2-0.4 | 4-5 |

TABLE 4-continued

| Semiconductor Compound | Dielectric | Drop-casting μ (cm²/Vs) | Drop-casting log($I_{on}$:$I_{off}$) | Vapor-phase μ (cm²/Vs) | Vapor-phase log($I_{on}$:$I_{off}$) |
|---|---|---|---|---|---|
| PDIPh12-$CN_2$ | $SiO_2$, $SiO_2$-HMDS, $SiO_2$-OTS | 0.01-0.1 | 4-5 | 0.2 | 5-6 |
| PDIPhCitr-$CN_2$ | $SiO_2$, $SiO_2$-HMDS, $SiO_2$-OTS, CPB | 0.05-0.2 | 4-5 | — | — |
| PDIPhs4-$CN_2$ | $SiO_2$, $SiO_2$-HMDS, $SiO_2$-OTS | — | — | 0.001-0.1 | 3-5 |
| PDIPhO7-$CN_2$ | $SiO_2$, $SiO_2$-HMDS, $SiO_2$-OTS | 0.01-0.2 | 2-5 | 0.08-0.2 | 4-5 |
| PDIPhPh-$CN_2$ | $SiO_2$-HMDS, $SiO_2$-OTS | 0.01-0.08 | 3-5 | 0.01-0.1 | 3-5 |
| PDIPhPh8-$CN_2$ | $SiO_2$-HMDS, $SiO_2$-OTS | 0.0001-0.01 | 2-3 | — | — |
| PDIPhPhCitr-$CN_2$ | $SiO_2$, $SiO_2$-HMDS, $SiO_2$-OTS, CPB | 0.05-0.4 | 4-5 | — | — |
| PDIPh1Ph-$CN_2$ | $SiO_2$-HMDS, $SiO_2$-OTS | — | — | — | — |
| PDI1Ph-$CN_2$ | $SiO_2$-HMDS, $SiO_2$-OTS | — | — | 0.1-0.3 | 3-5 |
| PDI1Ph4-$CN_2$ | $SiO_2$-HMDS, $SiO_2$-OTS | 0.01-0.05 | 3-4 | 0.01-0.1 | 3-5 |
| PDI1PhOCitr-$CN_2$ | $SiO_2$, $SiO_2$-HMDS, $SiO_2$-OTS | 0.05-0.3 | 4-5 | — | — |
| PDIPh2Ph-$CN_2$ | $SiO_2$-HMDS, $SiO_2$-OTS | 0.005-0.01 | 3-4 | — | — |

Example 27

Field Effect Transistor (FET) Fabrication by Spin-Coating

The representative compound (which may be a mixture of regioisomers) (4-8 mg) was dissolved in $CHCl_3$ (0.5-2 mL) and the solution was spin-coated (1500 rpm) on an OTS-treated Si—$SiO_2$ substrate. The film was then annealed at 80-120° C. in a vacuum-oven for 30 min-5 h. The FET device structure was completed by evaporation of the Au source/drain contacts.

FIG. 16A is a representative transfer plot measured in air for a spin-coated film from chloroform of a compound of the present teachings (PDI8-$CN_2$). FIG. 16B is a representative transfer plot measured in air for a spin-coated film from chloroform of a compound of the present teachings (PDI2EH-$CN_2$).

Table 5 summarizes electron mobilities and current $I_{on}$:$I_{off}$ ratios spin-coated films of representative PDI—$CN_2$ core compounds of the present teachings. In particular, it should be noted that the compounds having 2-alkyl substituted alkyl group functionalization of the imide nitrogens (PDI2MH—$CN_2$ and PDI2EH—$CN_2$) showed an unexpected increase in electron mobility and current $I_{on}$:$I_{off}$ ratio compared to a similar compound having a common known linear alkyl group substitution (PDI8-$CN_2$).

TABLE 5

| Semiconductor Compound | Dielectric | Spin-coating μ (cm²/Vs) | Spin-coating log($I_{on}$:$I_{off}$) | Vapor-phase μ (cm²/Vs) | Vapor-phase log($I_{on}$:$I_{off}$) |
|---|---|---|---|---|---|
| PDI8-$CN_2$ | $SiO_2$-OTS | $10^{-5}$-$10^{-3}$ | 2-4 | 0.1-0.2 | 4-5 |
| PDI2EH-$CN_2$ | $SiO_2$-OTS | 0.2-0.3 | 6-7 | 0.1-0.3 | 6-8 |
| PDI2MH-$CN_2$ | $SiO_2$-OTS | 0.1-0.2 | 6-7 | 0.1-0.2 | 6-7 |

The present teachings encompass embodiments in other specific forms without departing from the spirit or essential characteristics thereof. The foregoing embodiments are therefore to be considered in all respects illustrative rather than limiting on the present teachings described herein. Scope of the present teachings is thus indicated by the appended claims rather than by the foregoing description, and all changes that come within the meaning and range of equivalency of the claims are intended to be embraced therein.

What is claimed is:
1. A compound having the formula:

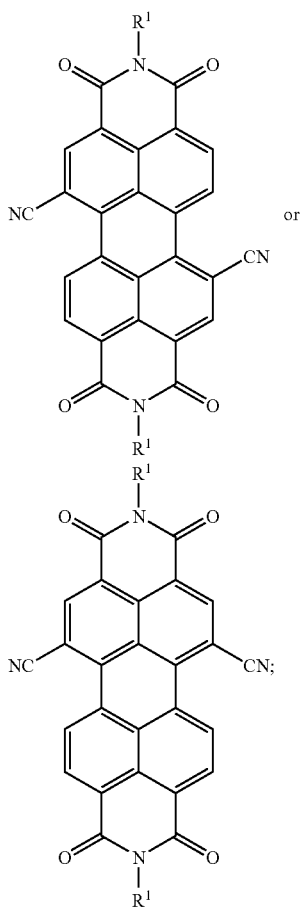

wherein each $R^1$ is an organic group comprising a 2-alkyl substituted alkyl group, a 3-alkyl substituted alkyl group, or a 3-alkyl substituted alkenyl group.

2. The compound of claim 1, wherein $R^1$ independently is a 2-alkyl substituted butyl group, a 2-alkyl substituted pentyl group, a 2-alkyl substituted hexyl group, a 2-alkyl substituted heptyl group, a 3-alkyl substituted butyl group, a 3-alkyl substituted pentyl group, a 3-alkyl substituted hexyl group, a 3-alkyl substituted heptyl group, a 3-alkyl substituted octyl group, or a 3,7-dialkyl substituted octyl group.

3. The compound of claim 1, wherein each $R^1$ independently is

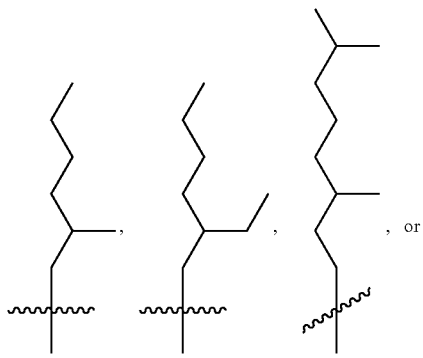

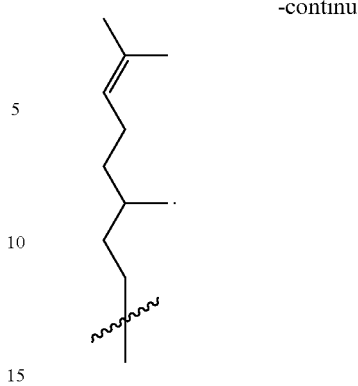

4. The compound of claim 1, wherein each $R^1$ is:

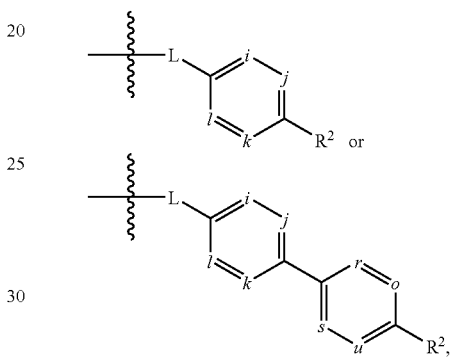

wherein i, j, k, l, o, r, s and u are independently CH, CF, or N; L is a divalent $C_{1-10}$ alkyl group, a divalent $C_{1-10}$ haloalkyl group, or a covalent bond; and $R^2$ is a 2-alkyl substituted alkyl group, a 3-alkyl substituted alkyl group, or a 3-alkyl substituted alkenyl group.

5. The compound of claim 4, wherein each $R^2$ is:

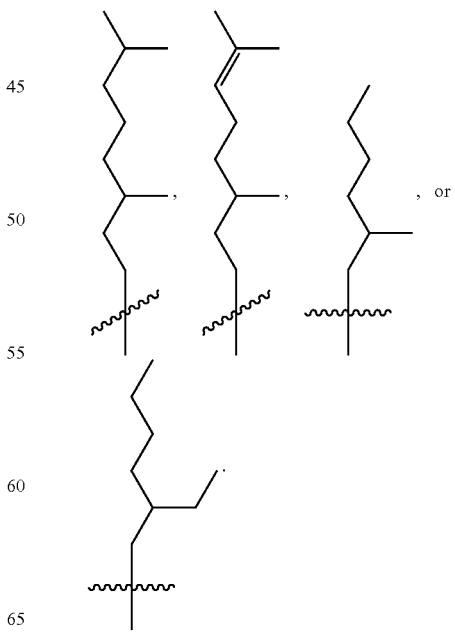

6. The compound of claim 1, wherein R¹ is:

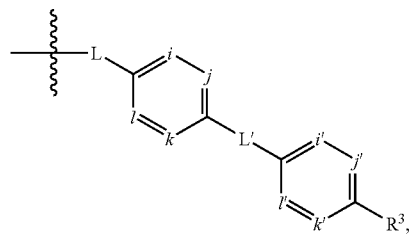

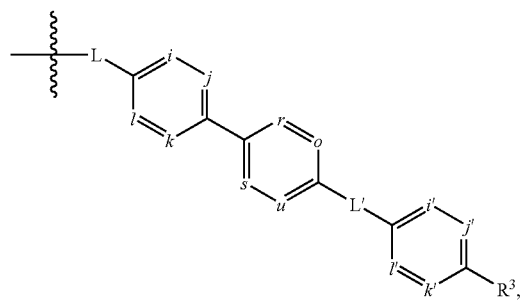

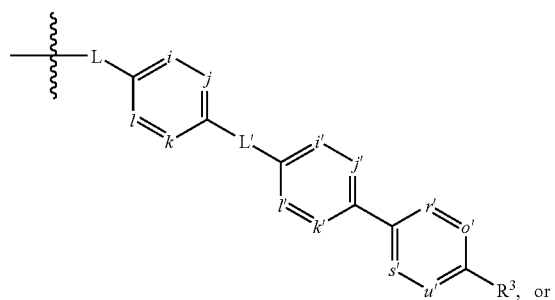

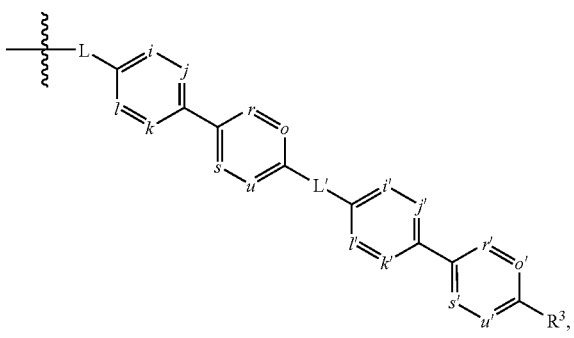

wherein:

i, j, k, l, o, r, s, u, i', j', k', l', o', r', s', and u' are independently CH, CF, or N;

L is a divalent $C_{1-10}$ alkyl group, a divalent $C_{1-10}$ haloalkyl group, or a covalent bond;

L' is —C(O)—, —O—, —S—, or —S(O)—, a divalent $C_{1-10}$ alkyl group, a divalent $C_{1-10}$ haloalkyl group, or a covalent bond; and R³ is a 2-alkyl substituted alkyl group, a 3-alkyl substituted alkyl group, or a 3-alkyl substituted alkenyl group.

7. The compound of claim 6, wherein R³ is:

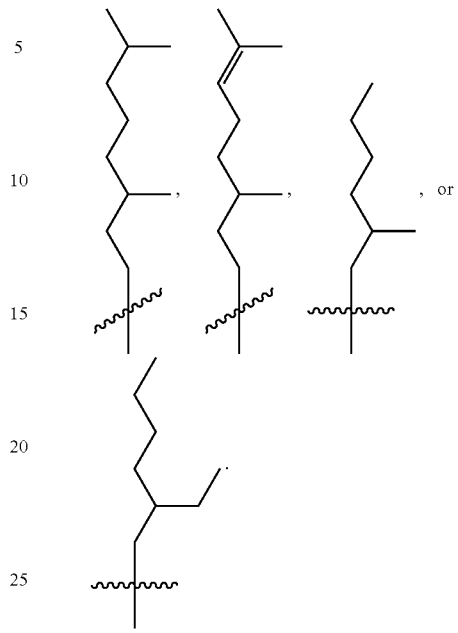

8. The compound of claim 1, wherein each R¹ is:

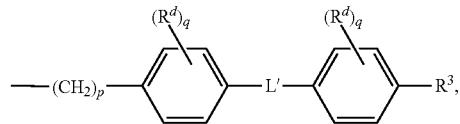

wherein $R^d$ is F; p is 0, 1 or 2; each q independently is 0 or 4; L' is —CH₂—, —CH₂CH₂—, —C(O)—, —O—, —S—, —S(O)—, or a covalent bond; and R³ is a 2-alkyl substituted alkyl group, a 3-alkyl substituted alkyl group, or a 3-alkyl substituted alkenyl group.

9. A compound selected from:

N,N'-bis[(3S)-3,7-dimethyl-6-octenyl]-1,7-dicyanoperylene-3,4:9,10-bis(dicarboxiamide);

N,N'-bis(2-methylhexyl)-1,7-dicyanoperylene-3,4:9,10-bis(dicarboxiamide);

N,N'-bis(2-ethylhexyl)-1,7-dicyanoperylene-3,4:9,10-bis(dicarboxiamide);

N,N'-bis{4-[(3S)-3,7-dimethyl-6-octenyl]phenyl}-1-1,7-dicyanoperylene-3,4:9,10-bis(dicarboxiamide);

N,N'-bis{4-[4'-((3S)-3,7-dimethyl-6-octenyl]biphenylyl}-1,7-dicyanoperylene-3,4:9,10-bis(dicarboxiamide);

N,N'-bis{4-[(3S)-3,7-dimethyl-6-octenyloxy]benzyl}-1,7-dicyanoperylene-3,4:9,10-bis(dicarboxiamide);

N,N'-bis[(3S)-3,7-dimethyl-6-octenyl]-1,6-dicyanoperylene-3,4:9,10-bis(dicarboxiamide);

N,N'-bis(2-methylhexyl)-1,6-dicyanoperylene-3,4:9,10-bis(dicarboxiamide);

N,N'-bis(2-ethylhexyl)-1,6-dicyanoperylene-3,4:9,10-bis(dicarboxiamide);

N,N'-bis{4-[(3S)-3,7-dimethyl-6-octenyl]phenyl}-1,6-dicyanoperylene-3,4:9,10-bis(dicarboxiamide);

N,N'-bis{4-[4'-((3S)-3,7-dimethyl-6-octenyl]biphenylyl}-1,6-dicyanoperylene-3,4:9,10-bis(dicarboxiamide); and N,N'-bis{4-[(3S)-3,7-dimethyl-6-octenyloxy]benzyl}-1,6-dicyanoperylene-3,4:9,10-bis(dicarboxiamide).

10. A composition comprising one or more compounds of claim 1 dissolved or dispersed in a liquid medium.

11. An article of manufacture comprising one or more compounds of claim 1, wherein the article of manufacture is a field effect transistor device, a photovoltaic device, or an organic light emitting diode device.

12. A thin film semiconductor comprising one or more compounds of claim 1.

13. A method of making an article of manufacture, the method comprising depositing a composition of claim 10 onto a substrate.

14. A method of making a compound of claim 1, the method comprising reacting a secondary imide nitrogen of a core structure of the compound to substitute a $R^1$ group thereon, wherein $R^1$ is as defined in claim 4.

15. A thin film semiconductor prepared from spin-coating a composition comprising one or more compounds of claim 1 onto a substrate.

16. An article of manufacture comprising the thin film semiconductor of claim 15, wherein the article of manufacture is a field effect transistor device, a photovoltaic device, or an organic light emitting diode device.

17. The article of manufacture of claim 16, wherein the article of manufacture is a field effect transistor device.

18. The article of manufacture of claim 11, wherein the article of manufacture is a field effect transistor device.

19. The method of claim 13, wherein depositing a composition comprises at least one of printing, spin coating, drop-casting, zone casting, dip coating, blade coating, spraying, and vapor deposition.

20. A field effect transistor device comprising a thin film semiconductor, wherein the thin film semiconductor comprises a compound of claim 9.

* * * * *